US012378193B2

(12) United States Patent
Chen et al.

(10) Patent No.: US 12,378,193 B2
(45) Date of Patent: Aug. 5, 2025

(54) ANTI-ARRHYTHMICITY AGENTS

(71) Applicant: The Regents of the University of California, Oakland, CA (US)

(72) Inventors: Jau-Nian Chen, Los Angeles, CA (US); Ohyun Kwon, Los Angeles, CA (US); Jie Huang, Los Angeles, CA (US); Hirohito Shimizu, Los Angeles, CA (US); Kui Lu, Los Angeles, CA (US); Johann Schredelseker, Los Angeles, CA (US); Yi Chiao Fan, Los Angeles, CA (US)

(73) Assignee: The Regents of The University of California, Oakland, CA (US)

( * ) Notice: Subject to any disclaimer, the term of this patent is extended or adjusted under 35 U.S.C. 154(b) by 635 days.

(21) Appl. No.: 17/573,442

(22) Filed: Jan. 11, 2022

(65) Prior Publication Data

US 2022/0127226 A1    Apr. 28, 2022

Related U.S. Application Data

(62) Division of application No. 15/536,314, filed as application No. PCT/US2015/065876 on Dec. 15, 2015, now abandoned.

(60) Provisional application No. 62/092,185, filed on Dec. 15, 2014.

(51) Int. Cl.
| | |
|---|---|
| *C07D 207/48* | (2006.01) |
| *A61K 31/40* | (2006.01) |
| *A61K 31/7088* | (2006.01) |
| *A61K 38/17* | (2006.01) |
| *A61K 48/00* | (2006.01) |
| *C12N 15/113* | (2010.01) |

(52) U.S. Cl.
CPC ............ *C07D 207/48* (2013.01); *A61K 31/40* (2013.01); *A61K 31/7088* (2013.01); *A61K 38/1709* (2013.01); *A61K 48/005* (2013.01); *C12N 15/113* (2013.01); *C12N 2310/11* (2013.01); *C12N 2320/31* (2013.01)

(58) Field of Classification Search
CPC ............... A61K 31/40; A61K 31/7088; A61K 38/1709; A61K 48/005; C07D 207/48; C07D 211/26; C12N 15/113; C12N 2310/11; C12N 2320/31; C07K 14/415; C07K 14/43
See application file for complete search history.

(56) References Cited

U.S. PATENT DOCUMENTS

| | | | | |
|---|---|---|---|---|
| 5,296,494 A | * | 3/1994 | Lavielle | C07D 207/08 548/530 |
| 6,838,460 B2 | * | 1/2005 | Himmelsbach | A61P 43/00 514/252.12 |
| 7,605,185 B2 | | 10/2009 | Graupner | |
| 2001/0051641 A1 | | 12/2001 | Mitaunobu | |
| 2010/0075898 A1 | | 3/2010 | Shosan-Barmatz et al. | |
| 2013/0102639 A1 | * | 4/2013 | Kwon | C07D 211/96 548/531 |
| 2013/0289086 A1 | * | 10/2013 | Duggan | A61P 25/22 514/397 |

FOREIGN PATENT DOCUMENTS

| | | |
|---|---|---|
| WO | 2004/110996 | 12/2004 |
| WO | 2005/079155 | 9/2005 |
| WO | 2007/113837 | 10/2007 |

OTHER PUBLICATIONS

Castellano et al. J. Am. Chem. Soc. 2007, 129, 5843-5845. (Year: 2007).*
Chen, 1590 Poster Board B360, PIIS0006349511030694, Pdf (www.cell.com) (Year: 2012).*
Adrio and Hii, "PhanePhos and Related Derivatives," *Encyclopedia of Reagents for Organic Synthesis*, 1-5, 2012.
Andrews et al. "Phosphine-catalyzed intramolecular γ-umpolung addition of α- aminoalkylallenic esters: facile synthesis of 3-carbethoxy-2-alkyl-3-pyrrolines" *Chemical Communications*, 48(43), 5373-5375, 2012.
Castellano et al., "Small-Molecule Inhibitors of Protein Geranylgeranyltransferase Type I" *Journal of the American Chemical Society*, 129(18), 5843-5845, 2007.
Chen et al. "Abstract 189: Activation of Voltage-Dependent Anion Channel 2 Suppresses $Ca^{2+}$-Induced Cardiac Arrhythmia", Poster presented in *Circulation Research*, November, 111:A189, 2012.
Ebert, et al., "Calcium Extrusion is Critical for Cardiac Morphogenesis and Rhythm in Embryonic Zebrafish Hearts," *PNAS*, 102(49): 17705-17710, 2005.
Fang et al., "Cooperative, Highly Enantioselective Phosphinothiourea Catalysis of Imine-Allene [3 + 2] Cycloadditions" *Journal of the American Chemical Society*, 130(17), 5660-5661, 2008.
Fleury-Bregeot et al., "Screening of chiral phosphines as catalysts for the enantioselective [3+2] annulations of N-tosylimines with allenic esters" *Tetrahedron*, 63(48), 11920-11927, 2007.
Grace & Camm, "Voltage-Gated Calcium-Channels and Antiarrhythmic Drug Action," Cardiovascular Research, 45; 43-51, 2000.
Han, et al., "Versatile Enantioselective [3+2] Cyclization Between Imines and Allenoates Catalyzed by Dipeptide-Based Phosphines," *Angewandte Chemie International Edition*, 51(3): 767-770, 2012.
Henry et al., "Hydroxyproline-Derived Pseudoenantiomeric [2.2.1] Bicyclic Phosphines: Asymmetric Synthesis of (+)- and (−)-Pyrrolines," *American Chemical Society* 2014, 136(34), 11890-11893, 2014.
International Search Report issued in corresponding International Application No. PCT/US2015/065876 and mailed Apr. 25, 2016.
Jean et al., "Phosphine-catalyzed enantioselective [3+2] annulations of 2,3-butadienoates with imines" *Tetrahedron Letters*, 47(13), 2141-2145, 2006.

(Continued)

*Primary Examiner* — Robert M Kelly
(74) *Attorney, Agent, or Firm* — Norton Rose Fulbright US LLP

(57) ABSTRACT

Agents, compositions, and methods for regulating cardiac rhythmicity are disclosed.

8 Claims, 23 Drawing Sheets

Specification includes a Sequence Listing.

(56) References Cited

OTHER PUBLICATIONS

Kim et al. "Ring-closing metathesis toward the synthesis of 2,5-dihydrofuran and 2,5- dihydropyrrole skeletons from Baylis-Hillman adducts" *Tetrahedron Letters*, 45(13), 2805-2808, 2004.

Langenbacher, et al., "Mutation in Sodium-Calcium Exchanger 1 (NCX1) Causes Cardiac Fibrillation in Zebrafish," *PNAS*, 102(49): 17699-17704, 2005.

Lammerhofer, M., "Chiral recognition by enantioselective liquid chromatography: Mechanisms and modern chiral stationary phases", *Journal of Chromatography A*, 1217, 814-856, 2010.

Liang et al., "Mechanism, Regioselectivity, and the Kinetics of Phosphine-Catalyzed [3+2] Cycloaddition Reactions of Allenoates and Electron-Deficient Alkenes" *Chemistry—A European Journal*, 14(14), 4361-4373, 2008.

Montero, et al., "Direct Activation of the Mitochondrial Calcium Uniporter by Natural Plant Flavonoids," Biochem. J., 384: 19-24, 2004.

Murphy et al., "Discovery of Novel, Potent, and Selective Inhibitors of 3-Phosphoinositide-Dependent Kinase (PDK1)" *Journal of Medicinal Chemistry*, 54(24), 8490-8500, 2011.

Scherer, Alexander, "A promising new catalyst family for enantioselective cycloadditions involving allenes and imines: chiral phosphines with transition metal-CH2-P: linkages" *Tetrahedron Letters*, 2006, 47(36), 6335-6337, 2006.

Schredelseker, J. et al., "High Resolution Structure and Double Electron-Electron Resonance of the Zebrafish Voltage-dependent Anion Channel 2 Reveal an Oligomeric Population," *The Journal of Biological Chemistry* 2014, 289(18), 12566-12577, 2014.

Shimizu, et al., "Mitochondrial $Ca^2$ Uptake by the Voltage-Dependent Anion Channel 2 Regulates Cardiac Rhythmicity," *eLife*, 4: e04801, 2015.

Sun, et al., "Asymmetric Organocatalytic Allylic Substitution of Morita-Baylis-Hillman Carbonates with Allylamines for the Synthesis of 2,5-Dihydropyrroles," *The Journal of Organic Chemistry*, 76(19): 7826-7833, 2011.

Supplementary Partial European Search Report issued in corresponding European Application No. EP15870900, dated Jun. 18, 2018.

Wang et al., "Diversity Through a Branched Reaction Pathway: Generation of Multicyclic Scaffolds and Identification of Antimigratory Agents" *Chemistry—A European Journal*, 17(2), 649-654, 2011.

Xu et al. "Silver-Catalyzed Intramolecular Aminofluorination of Activated Allenes" *Angewandte Chemie—International Edition*, 50(35), 8176-8179, 2011.

Xu et al., "A Novel [3+2] Cycloaddition Approach to Nitrogen Heterocycles via Phosphine-Catalyzed Reactions of 2,3-Butadienoates or 2-Butynoates and Dimethyl Acetylenedicarboxylate with Imines: A Convenient Synthesis of Pentabromopseudilin" *Journal of Organic Chemistry*, 63(15), 5031-5041, 1998.

\* cited by examiner

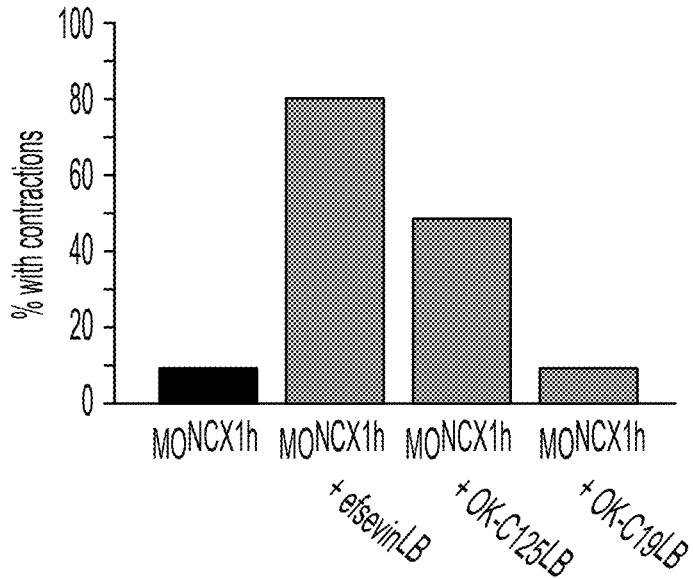

FIG. 3D

FIG. 3E
VDAC2 - 30% Sequence Coverage

MAVPPAYADLGKSAKDIFN
KGYGFGMVKLDVKTKSASG
VEFKTSGSSNTDTSKVVGS
LETKYKRSEYGLTFTEKWN
TDNTLGTEINIEDQIAKGL
KLTFDTTFSPNTGKKSGKV
KTAYKREFVNLGCDVDFDF
AGPTIHGAAVVGYEGWLAG
YQMSFDTAKSKMTQNNFAV
GYKTGDFQLHTNVNDGSEF
GGSIYQKVSDKLETAVNLA
WTAGSNSTRFGIAAKYQLD
KDASISAKVNNTSLVGVGY
TQSLRPGIKLTLSALVDGK
SINSGGHKLGLGLELEA

Formula Iv

Formula Iw

Formula Ix

Formula Iy

Formula Iz

```
SEQUENCE LISTING

<160> NUMBER OF SEQ ID NOS: 9

<210> SEQ ID NO 1
<211> LENGTH: 283
<212> TYPE: PRT
<213> ORGANISM: Artificial Sequence
<220> FEATURE:
<223> OTHER INFORMATION: Synthetic Peptide

<400> SEQUENCE: 1

Met Ala Val Pro Pro Ala Tyr Ala Asp Leu Gly Lys Ser Ala Lys Asp
1               5                   10                  15

Ile Phe Asn Lys Gly Tyr Gly Phe Gly Met Val Lys Leu Asp Val Lys
                20                  25                  30

Thr Lys Ser Ala Ser Gly Val Glu Phe Lys Thr Ser Gly Ser Ser Asn
            35                  40                  45

Thr Asp Thr Ser Lys Val Val Gly Ser Leu Glu Thr Lys Tyr Lys Arg
        50                  55                  60

Ser Glu Tyr Gly Leu Thr Phe Thr Glu Lys Trp Asn Thr Asp Asn Thr
65                  70                  75                  80

Leu Gly Thr Glu Ile Asn Ile Glu Asp Gln Ile Ala Lys Gly Leu Lys
                85                  90                  95

Leu Thr Phe Asp Thr Thr Phe Ser Pro Asn Thr Gly Lys Lys Ser Gly
            100                 105                 110

Lys Val Lys Thr Ala Tyr Lys Arg Glu Phe Val Asn Leu Gly Cys Asp
```

```
            115                 120                 125
Val Asp Phe Asp Phe Ala Gly Pro Thr Ile His Gly Ala Ala Val Val
130                 135                 140

Gly Tyr Glu Gly Trp Leu Ala Gly Tyr Gln Met Ser Phe Asp Thr Ala
145                 150                 155                 160

Lys Ser Lys Met Thr Gln Asn Asn Phe Ala Val Gly Tyr Lys Thr Gly
                165                 170                 175

Asp Phe Gln Leu His Thr Asn Val Asn Asp Gly Ser Glu Phe Gly Gly
            180                 185                 190

Ser Ile Tyr Gln Lys Val Ser Asp Lys Leu Glu Thr Ala Val Asn Leu
        195                 200                 205

Ala Trp Thr Ala Gly Ser Asn Ser Thr Arg Phe Gly Ile Ala Ala Lys
    210                 215                 220

Tyr Gln Leu Asp Lys Ser Ala Ser Ile Ser Ala Lys Val Asn Asn Thr
225                 230                 235                 240

Ser Leu Val Gly Val Gly Tyr Thr Gln Ser Leu Arg Pro Gly Ile Lys
                245                 250                 255

Leu Thr Leu Ser Ala Leu Val Asp Gly Lys Ser Ile Asn Ser Gly Gly
            260                 265                 270

His Lys Leu Gly Leu Gly Leu Glu Leu Glu Ala
        275                 280

<210> SEQ ID NO 2
<211> LENGTH: 35
<212> TYPE: DNA
<213> ORGANISM: Artificial Sequence
<220> FEATURE:
<223> OTHER INFORMATION: Synthetic Primer

<400> SEQUENCE: 2
aacactgaca ccagcaaagt ggttgggagc ctgga                         35

<210> SEQ ID NO 3
<211> LENGTH: 35
<212> TYPE: DNA
<213> ORGANISM: Artificial Sequence
<220> FEATURE:
<223> OTHER INFORMATION: Synthetic Primer

<400> SEQUENCE: 3
tccaggctcc caaccacttt gctggtgtca gtgtt                         35

<210> SEQ ID NO 4
<211> LENGTH: 96
<212> TYPE: DNA
<213> ORGANISM: Artificial Sequence
<220> FEATURE:
<223> OTHER INFORMATION: Synthetic Primer

<400> SEQUENCE: 4
aggaattcaa gacctctggt tcctccaaca ctgacaccag caaagtggtt gggagcctgg    60
aaaccaaata caagaggtct gaatatggcc tgacct                            96

<210> SEQ ID NO 5
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 5
```

```
Glu Phe Lys Thr Ser Gly Ser Ser Asn Thr Asp Thr Ser Lys Val Val
1               5                   10                  15

Gly Ser Leu Glu Thr Lys Tyr Lys Arg Ser Glu Tyr Gly Leu Thr
            20                  25                  30

<210> SEQ ID NO 6
<211> LENGTH: 62
<212> TYPE: DNA
<213> ORGANISM: Artificial Sequence
<220> FEATURE:
<223> OTHER INFORMATION: Synthetic Primer

<400> SEQUENCE: 6
aggaattcaa gaccttggga gcctggaaac caaatacaag aggtctgaat atggcctgac    60
ct                                                                   62

<210> SEQ ID NO 7
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 7

Glu Phe Lys Thr Leu Gly Ala Trp Lys Pro Asn Thr Arg Gly Leu Asn
1               5                   10                  15

Met Ala Lys

<210> SEQ ID NO 8
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 8

Leu Thr Phe Asp Thr Thr Phe Ser Pro Asn Thr Gly Lys
1               5                   10

<210> SEQ ID NO 9
<211> LENGTH: 25
<212> TYPE: DNA
<213> ORGANISM: Artificial Sequence
<220> FEATURE:
<223> OTHER INFORMATION: Synthetic Primer

<400> SEQUENCE: 9
gggaacggcc attttatctg ttaaa                                          25
```

ANTI-ARRHYTHMICITY AGENTS

CROSS REFERENCE TO RELATED APPLICATIONS

This application is a divisional of U.S. patent application Ser. No. 15/536,314, filed Jun. 15, 2017, which is a national phase application under 35 U.S.C. § 371 of International Application No. PCT/US2015/065876 filed Dec. 15, 2015, which claims the benefit of U.S. Provisional Application No. 62/092,185 filed Dec. 15, 2014. The entire contents of each of the above-referenced disclosures are specifically incorporated herein by reference without disclaimer.

FEDERAL GOVERNMENT GRANT INFORMATION

This invention was made with Government support under HL096980, GM071779, and GM081282 awarded by the National Institutes of Health. The Government has certain rights in the invention.

BACKGROUND OF THE INVENTION

A. Field of the Invention

The present invention relates to agents, compositions, and methods for regulating cardiac rhythmicity.

B. Description of Related Art

Cardiac diseases are the leading cause of death in Western countries. Many of these conditions, including hypertrophy, heart failure and arrhythmias, have a root in aberrant Ca2+ homeostasis. Identifying clinically relevant targets and pharmacological agents that can effectively modulate cardiac Ca2+ homeostasis may lead to the development of new therapeutic strategy for cardiac diseases.

The present invention addresses such needs for targets and agents for regulating cardiac rhythmicity.

SUMMARY OF THE INVENTION

In one embodiment, there are methods of regulating cardiac rhythmicity in a subject, comprising potentiating mitochondrial $Ca^{2+}$ uptake by inducing VDAC2 or VDAC1 overexpression in the subject to restore rhythmic contraction, inducing overexpression of or activating VDAC (VDAC2 or VDAC1) and/or MCU (MCU or MICU1) complex, or administering to the subject in need thereof an agent effective to induce Ca2+ transporting activity of VDAC2 or VDAC1.

In some embodiments, optionally in combination with any or all of the various embodiments disclosed herein, there are methods of regulating cardiac rhythmicity in a subject in need thereof comprising administering to the subject a composition that comprises an agent or compound that increases the activity of VDAC2 or VDAC1. In some embodiments, the agent or compound binds to VDAC2 or VDAC1. In some embodiments, the agent or compound increases Ca2+ transporting activity of VDAC2.

The agent or compound disclosed in the embodiments may be any agent or compound of the formulas described herein or compounds described herein. In some embodiments, one or more specific compounds described herein may be excluded.

In some embodiments, optionally in combination with any or all of the various embodiments disclosed herein, the compound is in a composition. In some embodiments, the composition comprises a pharmaceutically acceptable carrier.

In some embodiments, optionally in combination with any or all of the various embodiments disclosed herein, the subject suffers from a disorder related to cardiac arrhythmicity or cardiac disorder with a root in aberrant Ca2+ handling. Such disorder includes, for example, cardiac fibrillation, arrhythmia, atrial fibrillation, sick sinus syndrome, catecholaminergic polymorphic ventricular tachycardia (CPVT), or cardiomyopathy.

In some embodiments, optionally in combination with any or all of the various embodiments disclosed herein, inducing VDAC2 or VDAC1 overexpression in the subject is via gene therapy.

In some embodiments, optionally in combination with any or all of the various embodiments disclosed herein, the agent is a VDAC2 or VDAC1 gene product.

In some embodiments, optionally in combination with any or all of the various embodiments disclosed herein, the agent is a VDAC2 or VDAC1 protein, or a VDAC2 or VDAC1 RNA.

In some embodiments, optionally in combination with any or all of the various embodiments disclosed herein, the agent is the compound of Formula I or a derivative thereof, wherein compound of Formula I comprises

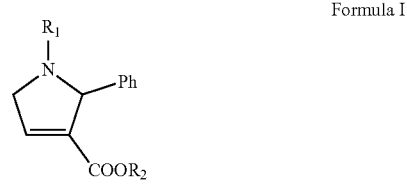

Formula I wherein: $R_1$ is tosyl, or mesyl group; and wherein $R_2$ is a hydrocarbyl group with or without a heteroatom or wherein the carboxylic ester of $R_2$ is attached to a mono-N-Boc protected 2,2'-(ethylenedioxy)bis(ethylamine), and wherein the compound is effective to potentiate mitochondrial $Ca^{2+}$ uptake so as to modulate cardiac rhythmicity in a subject, provided that when $R_1$ is tosyl and $R_2$ is ethyl, the compound is in an optionally active (e.g., substantially enantiomerically pure) form Formula Ia or Formula Ib:

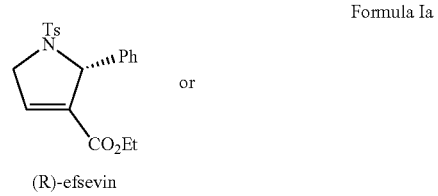

Formula Ia (R)-efsevin

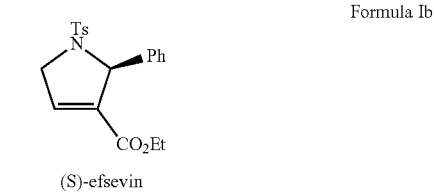

Formula Ib (S)-efsevin

In some embodiments, optionally in combination with any or all of the various embodiments disclosed herein, $R_2$ is methyl, ethyl, C3-C6 short alkyl, or menthyl group.

In some embodiments, optionally in combination with any or all of the various embodiments disclosed herein, $R_2$ is a C1-C10 straight or branched, acyclic or cyclic alkyl group, or aryl group.

In some embodiments, optionally in combination with any or all of the various embodiments disclosed herein, the compound is in an optionally active (e.g., substantially enantiomerically pure) form.

In some embodiments, optionally in combination with any or all of the various embodiments disclosed herein, the agent is efsevin.

In some embodiments, optionally in combination with any or all of the various embodiments disclosed herein, the efsevin is an efsevin enantiomer.

In some embodiments, optionally in combination with any or all of the various embodiments disclosed herein, the compound of Formula I is in a composition.

In some embodiments, optionally in combination with any or all of the various embodiments disclosed herein, the composition comprises a pharmaceutically acceptable carrier.

In some embodiments, optionally in combination with any or all of the various embodiments disclosed herein, the agent is the compound of Formula II, wherein compound of Formula II comprises:

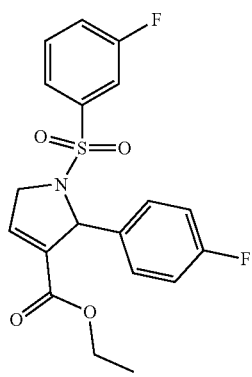

Formula II or wherein the carboxylic ester is attached to a mono-N-Boc protected 2,2'-(ethylenedioxy)bis(ethylamine).

In some embodiments, optionally in combination with any or all of the various embodiments disclosed herein, the compound is in an optionally active (e.g., substantially enantiomerically pure) form.

In some embodiments, optionally in combination with any or all of the various embodiments disclosed herein, the compound of Formula II is in a composition.

In some embodiments, optionally in combination with any or all of the various embodiments disclosed herein, the composition comprises a pharmaceutically acceptable carrier.

In another aspect, embodiments provide an anti-arrhythmicity compound of structure of Formula I or derivative thereof:

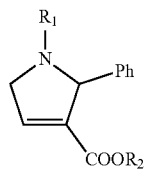

Formula I wherein: $R_1$ is tosyl, or mesyl group; and wherein $R_2$ is a hydrocarbyl group with or without a heteroatom or wherein the carboxylic ester of $R_2$ is attached to a mono-N-Boc protected 2,2'-(ethylenedioxy)bis(ethylamine), and wherein the compound is effective to potentiate mitochondrial $Ca^{2+}$ uptake so as to modulate cardiac rhythmicity in a subject, provided that when $R_1$ is tosyl and $R_2$ is ethyl, the compound is in an optionally active (e.g., substantially enantiomerically pure) form Formula Ia or Formula Ib:

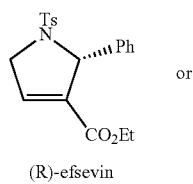

Formula Ia (R)-efsevin or

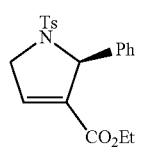

Formula Ib (S)-efsevin

In some embodiments, optionally in combination with any or all of the various embodiments disclosed herein, $R_2$ is methyl, ethyl, C3-C6 short alkyl, or menthyl group.

In some embodiments, optionally in combination with any or all of the various embodiments disclosed herein, $R_2$ is a C1-C10 straight or branched, acyclic or cyclic alkyl group, or aryl group.

In some embodiments, optionally in combination with any or all of the various embodiments disclosed herein, the compound is in an optionally active (e.g., substantially enantiomerically pure) form.

In a further aspect, embodiments involve methods of forming the compound of Formula I:

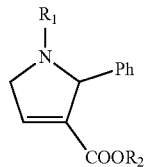

Formula I where $R_1$ is tosyl, or mesyl group; and $R_2$ is a hydrocarbyl group with or without a heteroatom or wherein the carboxylic ester of $R_2$ is attached to a mono-N-Boc protected 2,2'-(ethylenedioxy)bis(ethylamine), comprising reacting

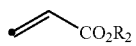

with

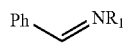

according to a reaction of Scheme I (Scheme I)

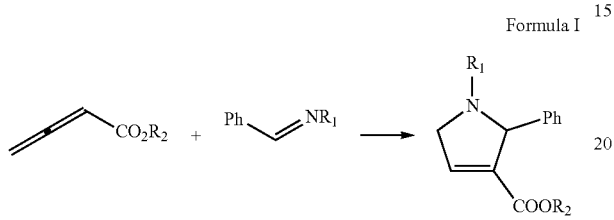

to form the compound of Formula I.

In some embodiments, optionally in combination with any or all of the various embodiments disclosed herein, the reaction of Scheme I is carried out under asymmetric synthesis conditions.

In some embodiments, optionally in combination with any or all of the various embodiments disclosed herein, the method further comprises performing chiral resolution of compound of Formula I to yield R- or S-enantiomers of the compound in an optionally active (e.g., substantially enantiomerically pure) form.

In some embodiments, optionally in combination with any or all of the various embodiments disclosed herein, the chiral resolution is performed on an HPLC chiral stationary phase.

In some embodiments, optionally in combination with any or all of the various embodiments disclosed herein, the chiral resolution is achieved by reacting the compound with a chiral agent.

In some embodiments, optionally in combination with any or all of the various embodiments disclosed herein, the chiral agent is menthol.

In a further aspect, there is provided a composition comprising the compound of Formula I or a derivative thereof:

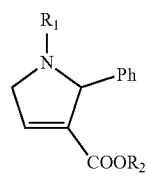

Formula I wherein: $R_1$ is tosyl, or mesyl group; and wherein $R_2$ is a hydrocarbyl group with or without a heteroatom or wherein the carboxylic ester of $R_2$ is attached to a mono-N-Boc protected 2,2'-(ethylenedioxy)bis(ethylamine), and wherein the compound is effective to potentiate mitochondrial $Ca^{2+}$ uptake so as to modulate cardiac rhythmicity in a subject, provided that when $R_1$ is tosyl and $R_2$ is ethyl, the compound is in an optionally active (e.g., substantially enantiomerically pure) form Formula Ia or Formula Ib:

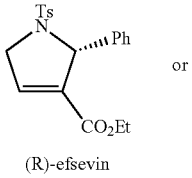

Formula Ia (R)-efsevin or

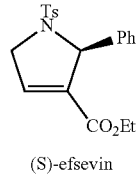

Formula Ib (S)-efsevin

In some embodiments of the invention composition, optionally in combination with any or all of the various embodiments disclosed herein, $R_2$ is methyl, ethyl, C3-C6 short alkyl, or menthyl group.

In some embodiments of the invention composition, optionally in combination with any or all of the various embodiments disclosed herein, $R_2$ is a C1-C10 straight or branched, acyclic or cyclic alkyl group, or aryl group.

In some embodiments of the invention composition, optionally in combination with any or all of the various embodiments disclosed herein, the compound is in an optionally active (e.g., substantially enantiomerically pure) form.

In some embodiments of the invention composition, optionally in combination with any or all of the various embodiments disclosed herein, the composition is in a formulation suitable for administration to a subject.

In a further aspect of the present invention, it is provided a method of forming a composition, comprising providing a compound of Formula I or a derivative thereof in an effective amount, and forming the composition, wherein the compound of Formula I comprises:

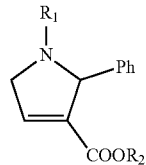

Formula I wherein: $R_1$ is tosyl, or mesyl group; and wherein $R_2$ is a hydrocarbyl group with or without a heteroatom or wherein the carboxylic ester of $R_2$ is attached to a mono-N-Boc protected 2,2'-(ethylenedioxy)bis(ethylamine), and wherein the compound is effective to potentiate mitochondrial $Ca^{2+}$ uptake so as to modulate cardiac rhythmicity in a subject, provided that when $R_1$ is tosyl and $R_2$ is ethyl, the compound is in an optionally active (e.g., substantially enantiomerically pure) pure form Formula Ia or Formula Ib:

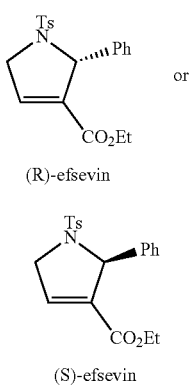

Formula Ia (R)-efsevin

Formula Ib

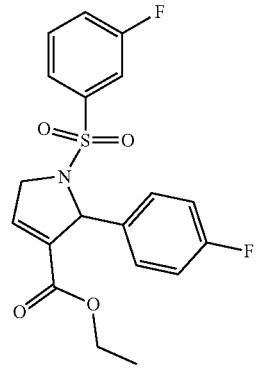

Formula II

In some embodiments of the invention method, optionally in combination with any or all of the various embodiments disclosed herein, R$_2$ is methyl, ethyl, C3-C6 short alkyl, or menthyl group.

In some embodiments of the invention method, optionally in combination with any or all of the various embodiments disclosed herein, R$_2$ is a C1-C10 straight or branched, acyclic or cyclic alkyl group, or aryl group.

In some embodiments of the invention method, optionally in combination with any or all of the various embodiments disclosed herein, the compound is in an optionally active (e.g., substantially enantiomerically pure) form.

In some embodiments of the invention method, optionally in combination with any or all of the various embodiments disclosed herein, the composition is in a formulation suitable for administration to a subject.

In another aspect, embodiments provide an anti-arrhythmicity compound of structure of Formula II:

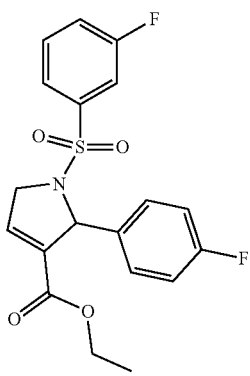

Formula II or wherein the carboxylic ester is attached to a mono-N-Boc protected 2,2'-(ethylenedioxy)bis(ethylamine).

In some embodiments, optionally in combination with any or all of the various embodiments disclosed herein, the compound is in an optionally active (e.g., substantially enantiomerically pure) form.

In a further aspect, there is provided a composition comprising the compound of Formula II:

or wherein the carboxylic ester is attached to a mono-N-Boc protected 2,2'-(ethylenedioxy)bis(ethylamine).

In some embodiments of the invention composition, optionally in combination with any or all of the various embodiments disclosed herein, the compound is in an optionally active (e.g., substantially enantiomerically pure) form.

In some embodiments of the invention composition, optionally in combination with any or all of the various embodiments disclosed herein, the composition is in a formulation suitable for administration to a subject.

In a further aspect of the present invention, it is provided a method of forming a composition, comprising providing a compound of Formula II in an effective amount, and forming the composition, wherein the compound of Formula II comprises:

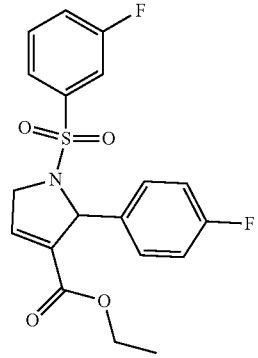

Formula II or wherein the carboxylic ester is attached to a mono-N-Boc protected 2,2'-(ethylenedioxy)bis(ethylamine).

In some embodiments of the invention composition, optionally in combination with any or all of the various embodiments disclosed herein, the compound is in an optionally active (e.g., substantially enantiomerically pure) form.

In some embodiments of the invention composition, optionally in combination with any or all of the various embodiments disclosed herein, the composition is in a formulation suitable for administration to a subject.

BRIEF DESCRIPTION OF THE DRAWINGS

FIGS. 3A-3E show test results demonstrating VDAC2 is a protein target of efsevin. (A) Structures of efsevin and two derivatives, OK-C125 and OK-C19. (B) Efsevin and OK-C125 restored rhythmic contractions in the majority of tremblor embryos, whereas OK-C19 failed to rescue the tremblor phenotype. (C) Structures of linker-attached compounds (indicated by superscript L). (D) Compounds efsevin$^L$ and OK-C125$^L$ retained their ability to restore rhythmic contractions in NCX1hMO injected embryos, while the inactive derivative OK-C19$^L$ was still unable to induce rhythmic contraction. (E) Mass Spectrometry identification of VDAC 2, a 32 kD band pulled down with affinity agarose beads covalently linked with efsevin (efsevin$^{LB}$) or OK-C125 (OK-C125$^{LB}$) that was sensitive to competition with a 100 fold excess free efsevin$^L$. The 32 kD band was not detected in proteins eluted from beads capped with ethanolamine alone (beads$^C$) or beads linked to OK-C19 (OK-C19$^{LB}$). Peptides identified by mass spectrometry (underlined) account for 30% of the total sequence (SEQ ID NO: 1).

Figure 1A:
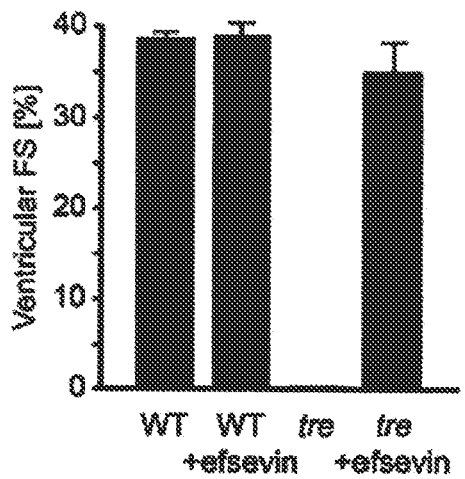
FIGS. 1A-1G show test results demonstrating that efsevin restores rhythmic cardiac contractions in zebrafish tremblor embryos. (A,B) Fractional shortening (FS) deduced from line scans across the atria of Tg(myl7:GFP) embryonic hearts at 48 hpf. Rhythmically alternating systoles and diastoles were recorded from vehicle- or efsevin-treated wild type and efsevin-treated tre embryos, while only sporadic unsynchronized contractions were recorded from vehicle-treated tre embryos. While cardiac contraction was not observed in tre, efsevin-treated wild type and tre hearts have similar levels of FS to those observed in control hearts. Ventricular FS of wild type v.s. wild type+ efsevin vs. tre+ efsevin: 39±0.6%, n=8 vs. 39±1%, n=10 vs. 35±3%, n=6; and Atrial FS: 37±1%, n=11 vs. 35±2%, n=11 vs. 33±2%, n=15. (C) While efsevin restored a heart rate of 46±2 beats per minute (bpm) in tre embryos, same treatment does not affect the heart rate in wild type embryos (126±2 bpm in vehicle-treated embryos vs. 123±3 bpm in efsevin-treated wild-type embryos). ***, p<0.001 by one-way ANOVA. (D) Dose-dependence curve for efsevin. The tre embryos were treated with various concentrations of efsevin from 24 hpf and cardiac contractions were analyzed at 48 hpf. (E-G) Representative time traces of local field potentials for wild type (E), tre (F) and efsevin-treated tre (G) embryos clearly display periods of regular, irregular, and restored periodic electrical activity.

A) Injection of 25 pg in-vitro synthesized VDAC1 and VDAC2 mRNA restored cardiac contractions in 53.0±10.2% (n=126) and 52.9±12.1% (n=78) of one-day-old tre embryos, respectively, compared to 21.8±5.1% in uninjected siblings (n=111).

B) While only ~20% of myl7:VDAC2; NCX1hMO embryos have coordinated contractions (n=116), 52.3±2.4% of these embryos established persistent, rhythmic contractions after TBF induction of VDAC2 (n=154).

C) On average, 71.2±8.8% efsevin treated embryos have coordinated cardiac contractions (n=131). Morpholino antisense oligonucleotide knockdown of VDAC2 (MO$^{VDAC2}$) or VDAC1 (MO$^{VDAC1}$) attenuates the ability of efsevin to suppress cardiac fibrillation in tre embryos (45.3±7.4% and 46.9±10.7% embryos with coordinated contractions, n=94 and 114, respectively). Knocking down VDAC1/2 simultaneously further suppresses efsevin's effect (30.3±6.3%, n=75).

D) Efsevin treatment restores coordinated cardiac contractions in 76.2±8.7% NCX1MO embryos, only 54.1±3.6% VDAC2$^{zfn/zfn}$; NCX1MO embryos and 35.7±7.1% VDAC2$^{zfn/zfn}$; VDAC1MO; NCX1MO embryos have coordinated contractions (n=250).

E) Overexpression of MCU is sufficient to restore coordinated cardiac contractions in tre embryos (47.1±1.6% embryos, n=112 as opposed to 18.3±5.3% of uninjected siblings, n=64) while this effect is significantly attenuated when co-injected with morpholino antisense oligonucleotide targeted to VDAC2 (27.1±1.9% embryos, n=135).

F) Suboptimal overexpression of MCU (MCU$^S$) and VDAC2 (VDAC2$^S$) in combination is able to suppress cardiac fibrillation in tre embryos (42.9±2.6% embryos, n=129).

G) The ability of VDAC2 to restore rhythmic contractions in tre embryos (48.5±3.5% embryos, n=111) is significantly attenuated when MCU is knocked down by antisense oligonucleotide (MO$^{MCU}$) (25.6±2.4% embryos, n=115). Error bars represent s.d.; *p<0.05; ***p<0.001.

Figure 10:
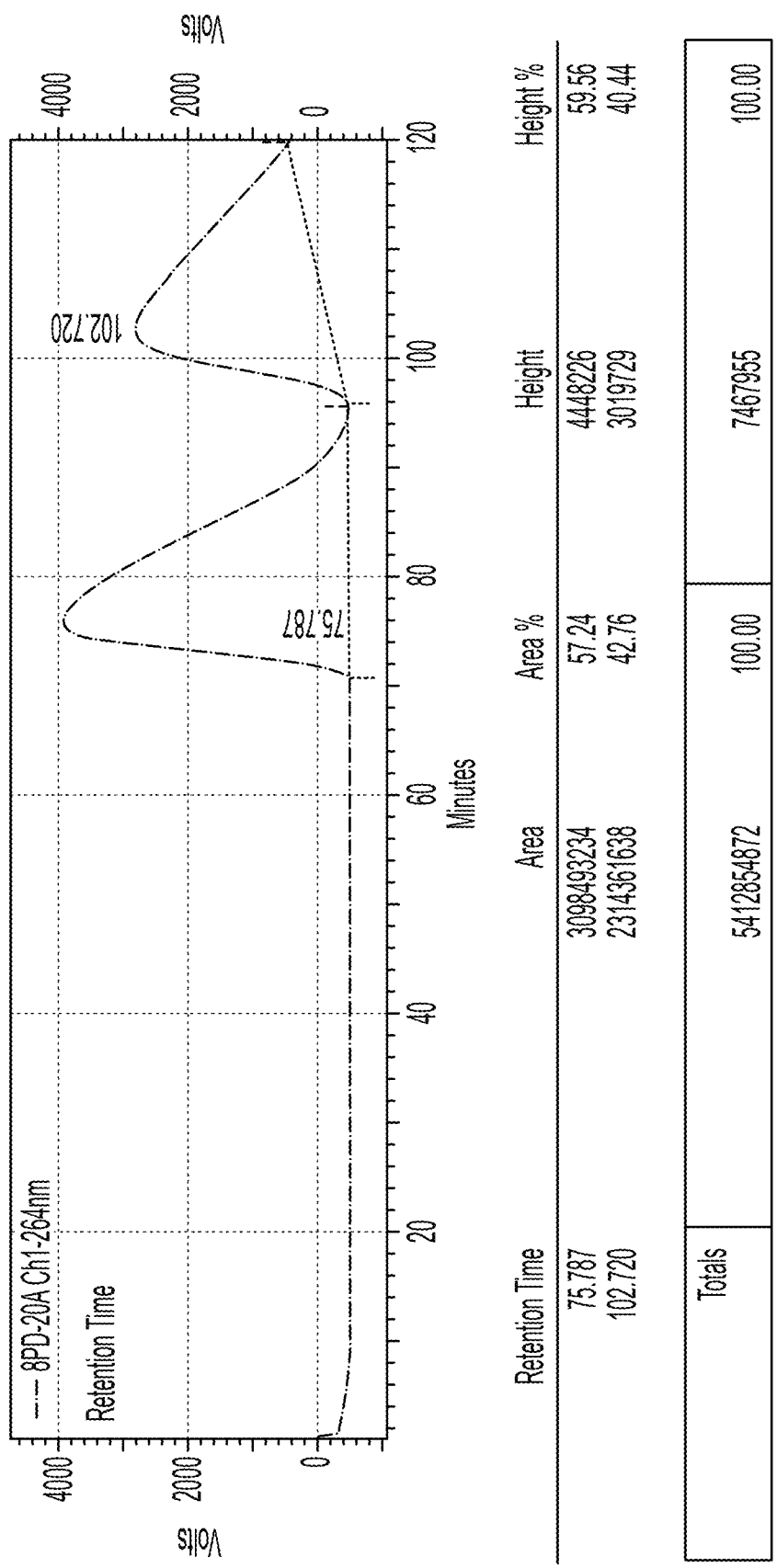

FIG. 10 shows resolution of (R)- and (S)-efsevin from a mixture of (R)- and (S)-efsevin through HPLC separation.

Figure 11:
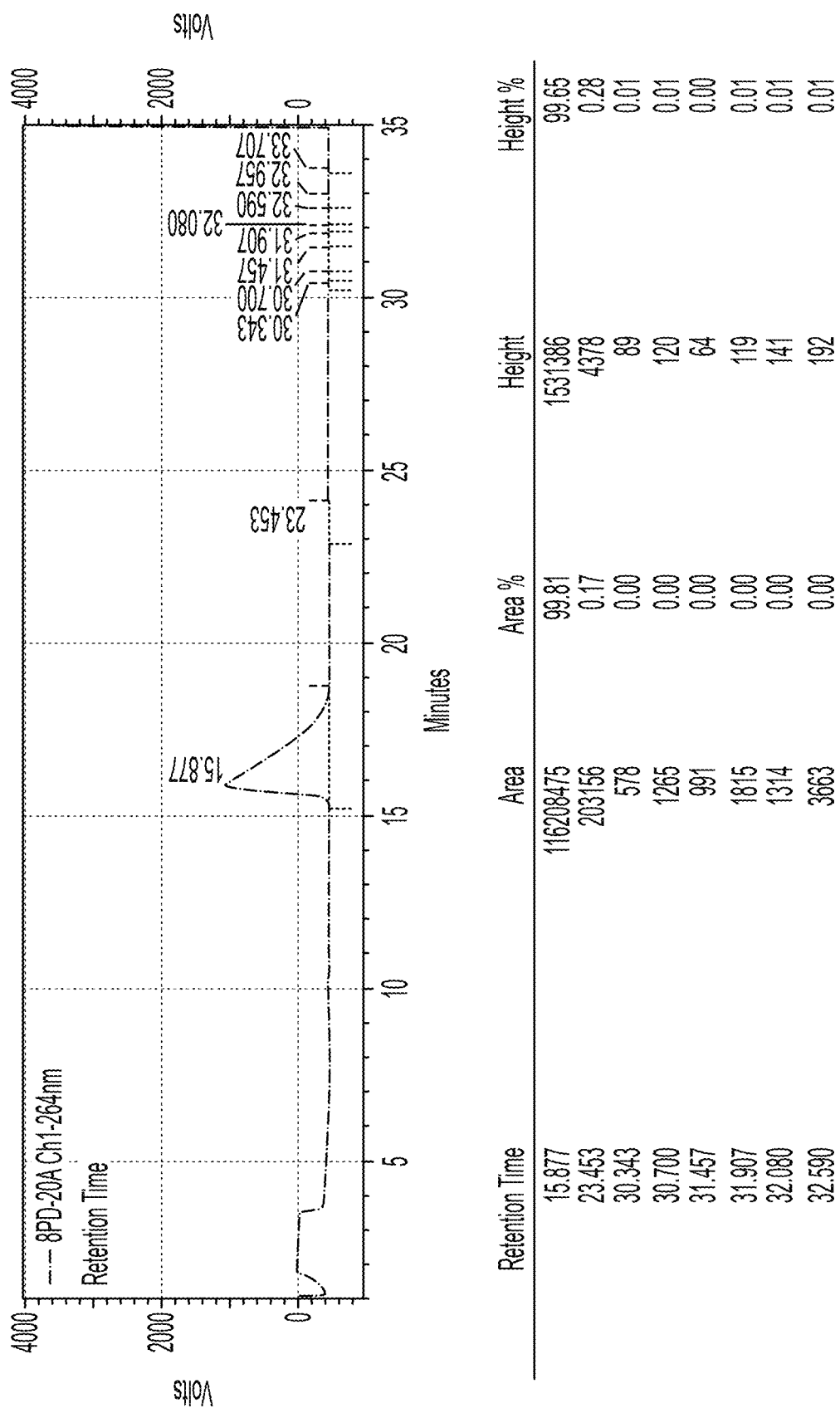

FIG. 11 shows purification of (R)-efsevin through HPLC separation.

Figure 12:
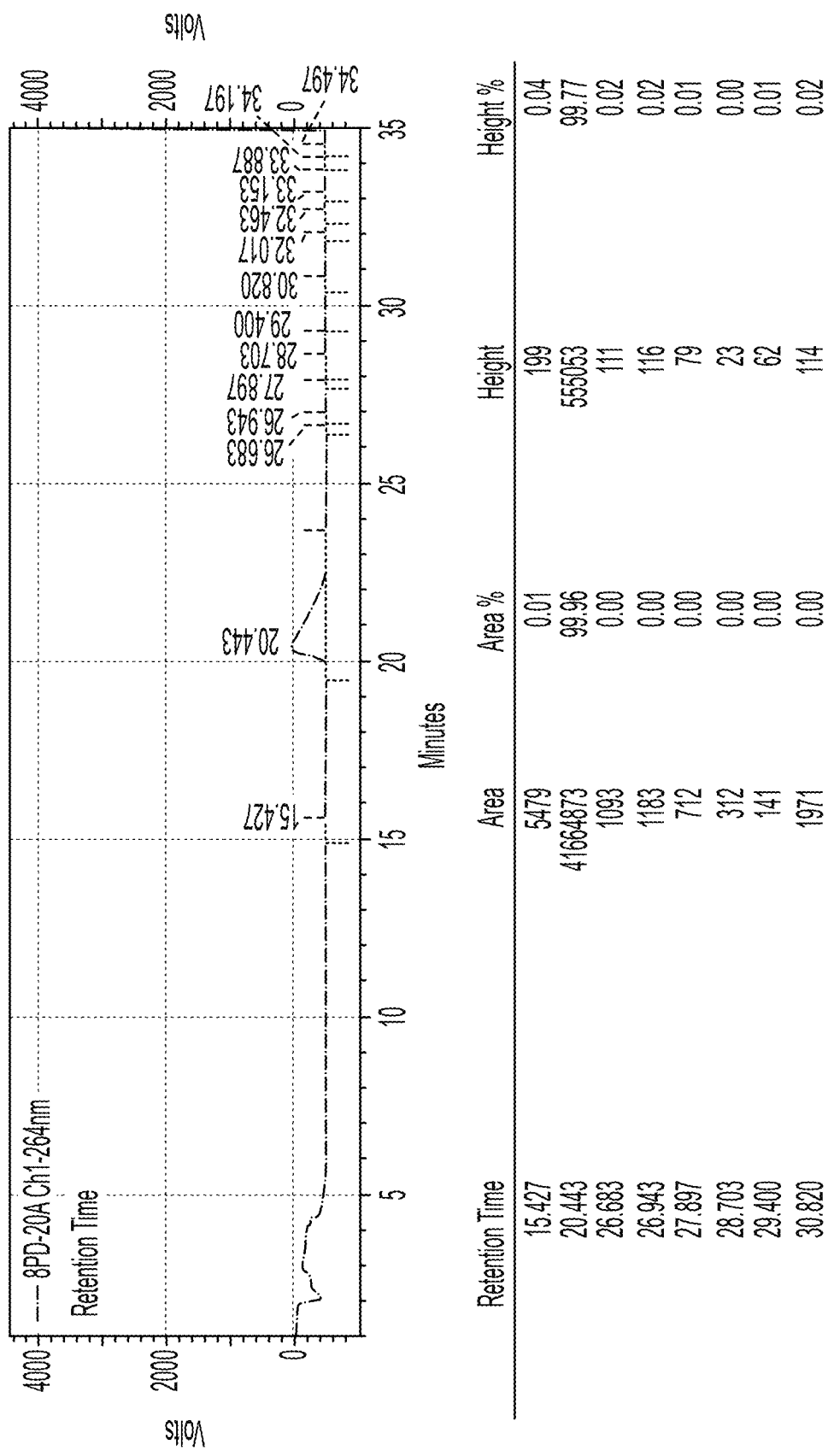

FIG. 12 shows purification of (S)-efsevin through HPLC separation.

Figure 13:
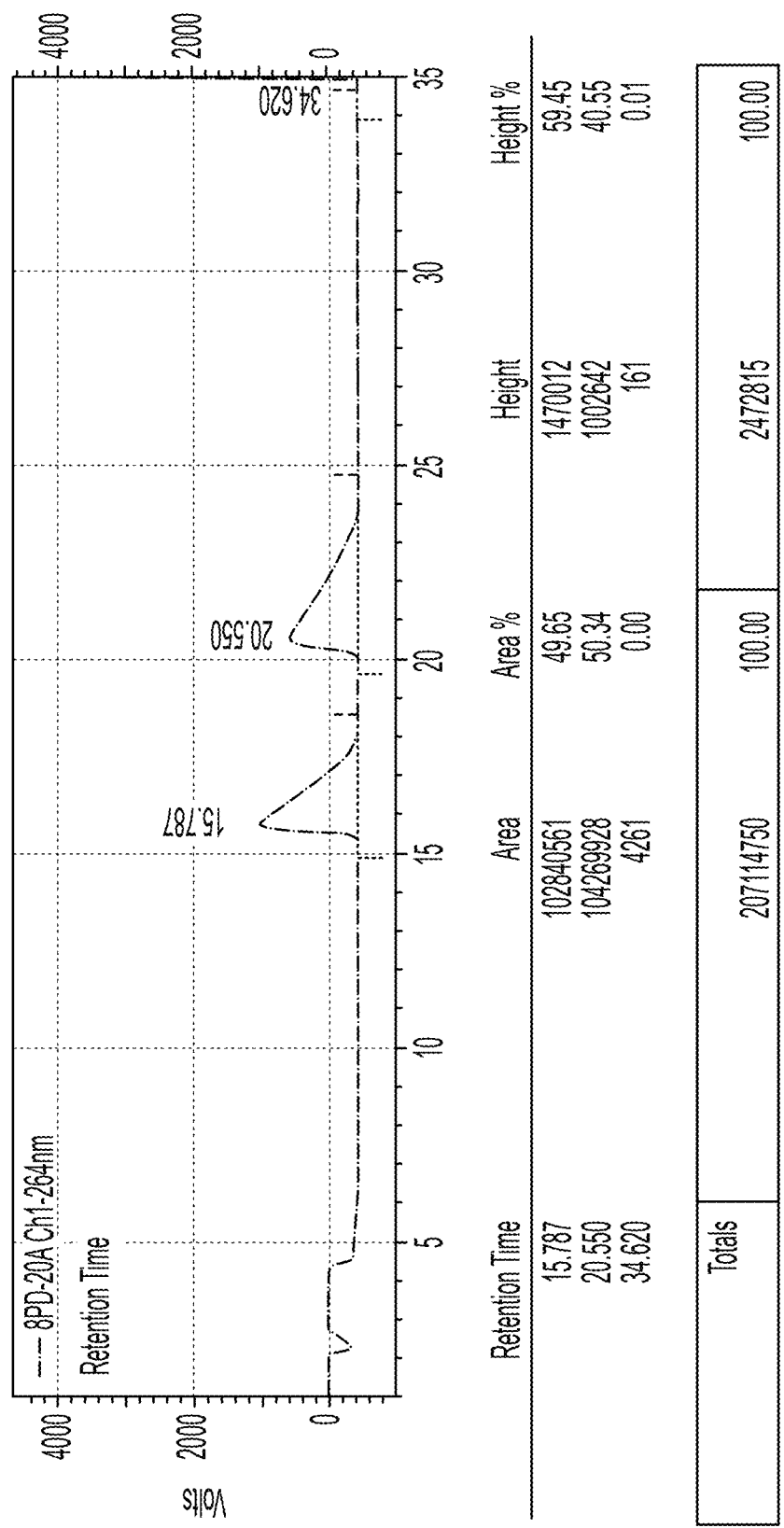

FIG. 13 shows resolution of (R)- and (S)-efsevin from a racemic mixture of efsevin through HPLC separation.

Figure 14:
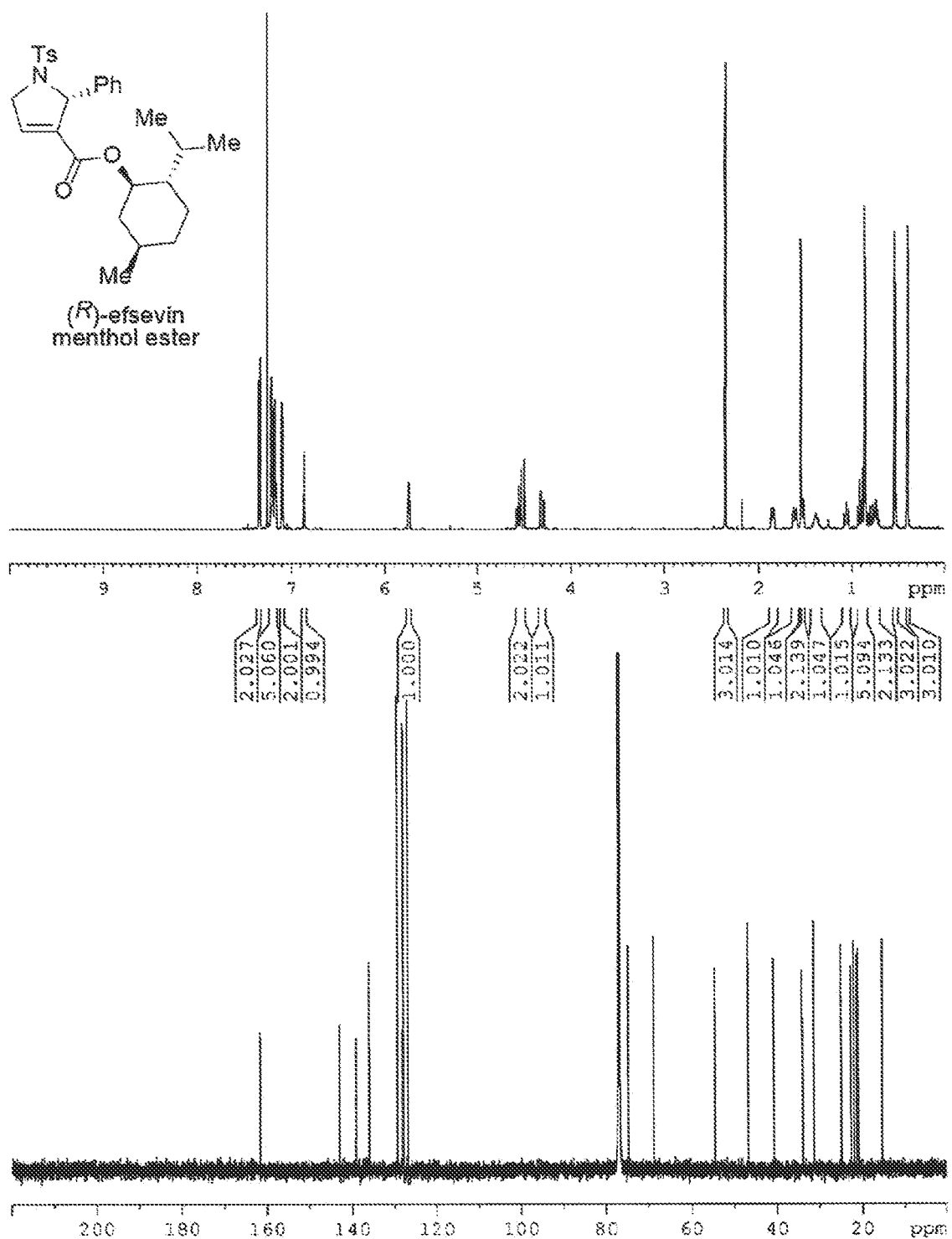

FIG. 14 shows ¹H NMR (top) and ¹³C NMR (bottom) of (R)-Efsevin menthol ester.

Figure 15:
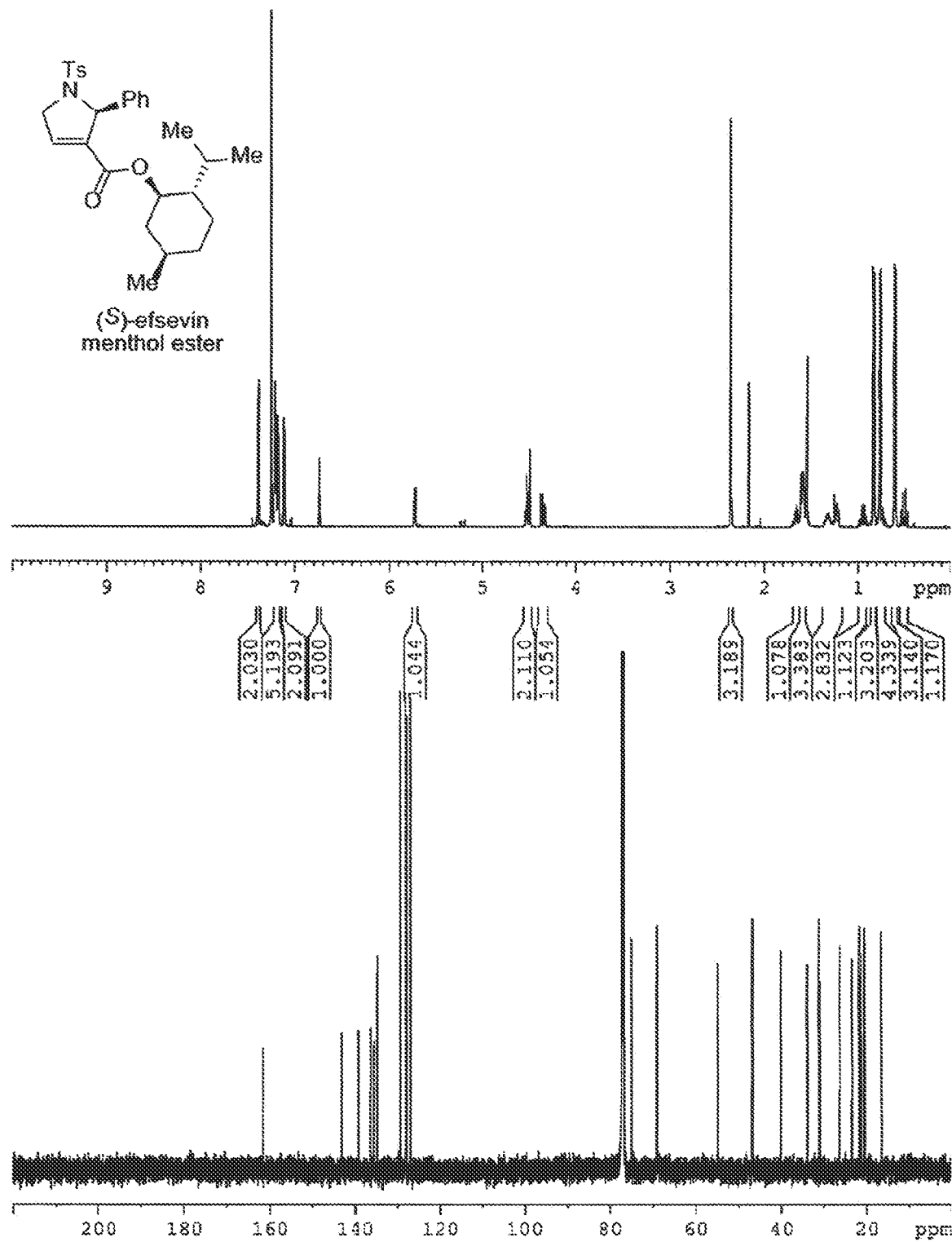

FIG. 15 shows ¹H NMR (top) and ¹³C NMR (bottom) of (S)-Efsevin menthol ester.

Figure 16A:
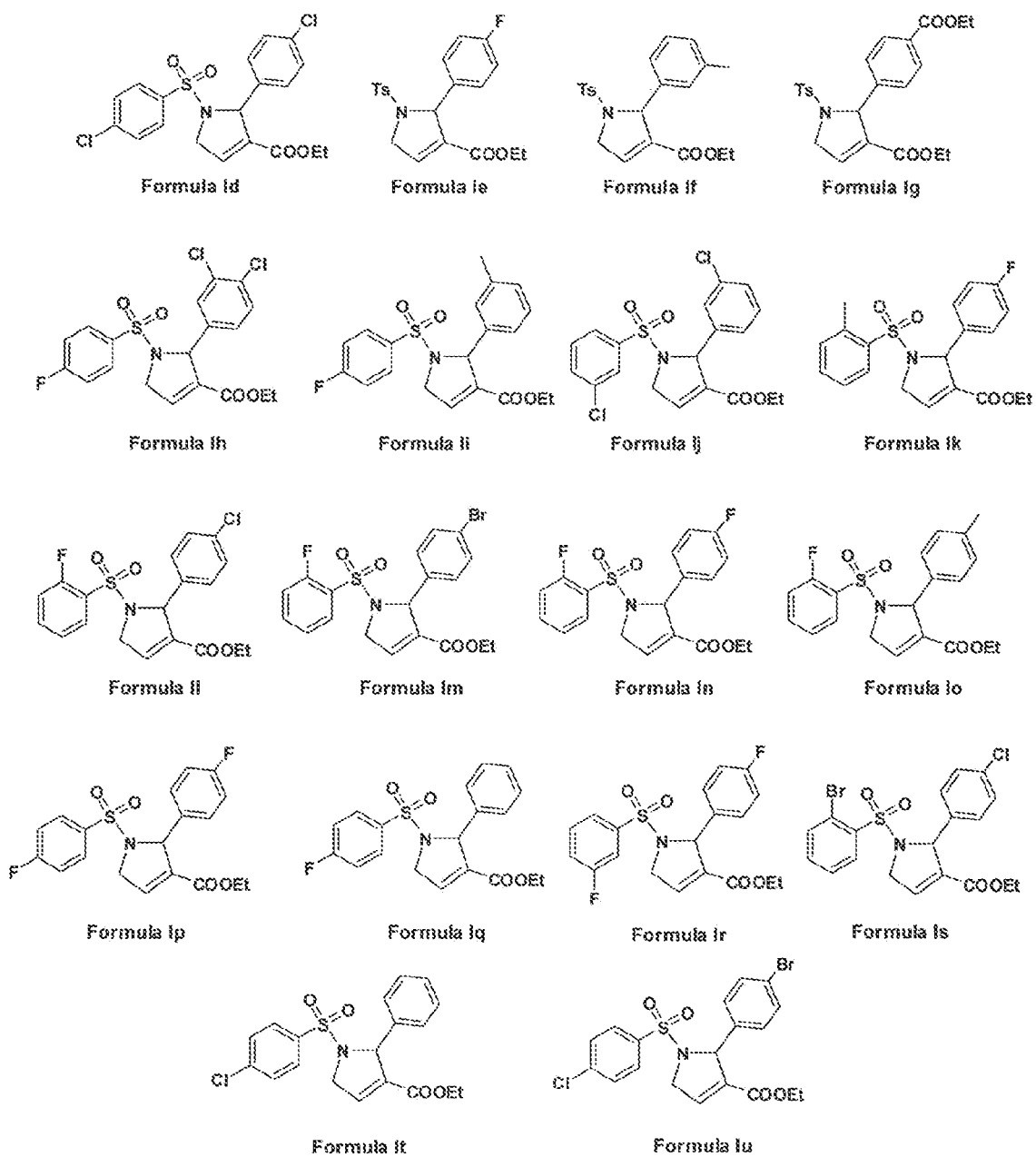
Figure 16B:
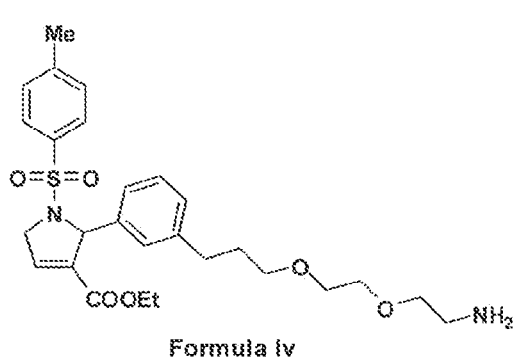
Figure 16B:
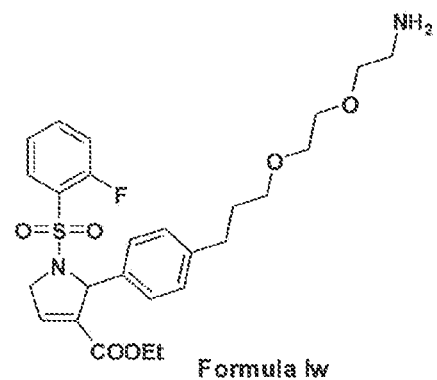
Figure 16B:
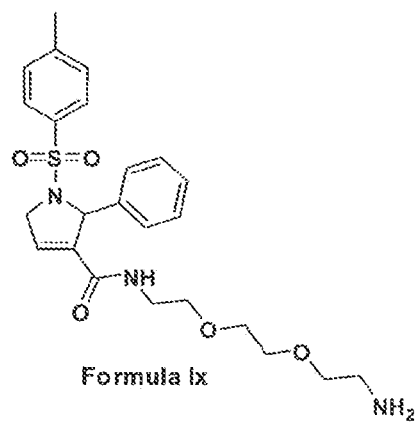
Figure 16B:
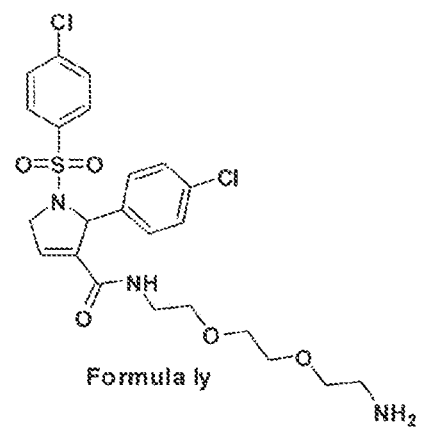
Figure 16B:
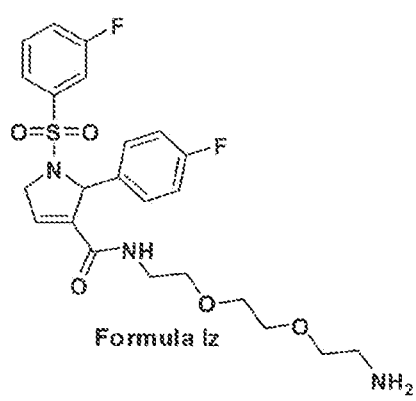

FIGS. 16A and 16B show active compounds found through forward chemical genetics.

DETAILED DESCRIPTION OF THE INVENTION

A. Definitions

The term "effective amount", as used herein, is an amount of an agent that is sufficient to produce a statistically significant, measurable change of a condition in cardiac rhythmicity as compared with the condition in cardiac rhythmicity without using the agent. Such effective amounts can be gauged in clinical trials as well as animal studies. Such a statistically significant, measurable, and positive change of a condition in cardiac rhythmicity using the agent disclosed herein as compared with the condition in the cardiac rhythmicity without using the agent is referred to as being an "improved condition".

As used herein, the term "agent" refers to an agent that capable of potentiating mitochondrial Ca²⁺ uptake to effect VDAC2 expression in a subject. In some embodiments, the term agent can refer to as "anti-arrhythmicity" drug or compound.

As used herein, the term "subject" as used herein is any vertebrate. Subjects include individuals in need of drug (e.g. an agent disclosed herein such as efsevin) treatment (patients) and individuals not in need of drug treatment (e.g. normal healthy volunteers). Humans are preferred subjects and patients.

"Treat" or "treatment" refers to any treatment of a disorder or disease, such as preventing the disorder or disease from occurring in a subject which may be predisposed to the disorder or disease, but has not yet been diagnosed as having the disorder or disease; inhibiting the disorder or disease, e.g., arresting the development of the disorder or disease, relieving the disorder or disease, causing regression of the disorder or disease, relieving a condition caused by the disease or disorder or reducing the symptoms of the disease or disorder.

As used herein, the term "disorder" generally refers to a condition related to cardiac cardiac arrhythmicity or cardiac disorder with a root in aberrant Ca2+ handling. Such disorder includes, for example, cardiac fibrillation, arrhythmia, atrial fibrillation, sick sinus syndrome, catecholaminergic polymorphic ventricular tachycardia, or cardiomyopathy.

As used herein, the term "derivative" refers to a form of the agent or compound disclosed herein, which derivative is capable of generating an active species or moiety in vitro or in vivo having anti-arrhythmicity activities as is the agent or compound disclosed herein. Non-limiting examples of such "derivative" includes prodrug or metabolite.

As used herein, the term "optically active" refers to the compound Formula I disclosed herein that is not a 50/50 R/S racemic mixture of the compound of Formula I.

As used herein, the term "substantially enantiomerically pure" refers to the purity of S- or R-enantiomer of the compound of Formula I of about 60%—about 100%, of about 70%—about 100%, of about 80%—about 100%, of about 90%—about 100%, of about 95%—about 100%, e.g., of about 75%, of about 80%, of about 85%, or of about 99%.

As used herein, the term "enantiomer" refers to a compound disclosed herein that is optically active or substantially enantiomerically pure.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus, for example, references to "the method" include one or more methods, and/or steps of the type described herein and/or which will become apparent to those persons skilled in the art upon reading this disclosure and so forth.

B. Mitochondrial $Ca^{2+}$ Uptake Regulates Cardiac Rhythmicity

In an aspect of the present invention, it is provided a method of regulating cardiac rhythmicity in a subject, comprising potentiating mitochondrial $Ca^{2+}$ uptake by inducing VDAC2 or VDAC1 overexpression in the subject to restore rhythmic contraction, inducing overexpression of or activating VDAC (VDAC2 or VDAC1) and/or MCU (MCU or MICU1) complex, or administering to the subject in need thereof an agent effective to induce Ca2+ transporting activity of VDAC2 or VDAC1.

In some embodiments, optionally in combination with any or all of the various embodiments disclosed herein, the subject suffers from a disorder related to cardiac arrhythmicity or cardiac disorder with a root in aberrant Ca2+ handling. Such disorder includes, for example, cardiac fibrillation, arrhythmia, atrial fibrillation, sick sinus syndrome, catecholaminergic polymorphic ventricular tachycardia, or cardiomyopathy.

In some embodiments of the invention method, optionally in combination with any or all of the various embodiments disclosed herein, inducing VDAC2 or VDAC1 overexpression in the subject is via gene therapy.

In some embodiments of the invention method, optionally in combination with any or all of the various embodiments disclosed herein, the agent is a VDAC2 or VDAC1 gene product.

In some embodiments of the invention method, optionally in combination with any or all of the various embodiments disclosed herein, the agent is a VDAC2 or VDAC1 protein, or a VDAC2 or VDAC1 RNA.

In some embodiments of the invention method, optionally in combination with any or all of the various embodiments disclosed herein, the agent is the compound of Formula I, which is described in detail below. For concise description of the present invention, the description of the compound of Formula I is not repeated here but is fully incorporated hereto by reference.

In some embodiments of the invention method, optionally in combination with any or all of the various embodiments disclosed herein, the agent is efsevin.

In some embodiments of the invention method, optionally in combination with any or all of the various embodiments disclosed herein, the efsevin is an efsevin enantiomer.

In some embodiments of the invention method, optionally in combination with any or all of the various embodiments disclosed herein, the compound of Formula I is in a composition.

In some embodiments of the invention method, optionally in combination with any or all of the various embodiments disclosed herein, the composition comprises a pharmaceutically acceptable carrier.

C. Gene Therapy

In some embodiments, potentiating mitochondrial Ca2+ uptake can be achieved by overexpression of VDAC2 or VDAC1 by delivery to a subject in need thereof a VDAC2- or VDAC1-encoding gene sequence using a viral or non-viral vector. Vectors for transduction of a VDAC2- or VDAC1-encoding sequence are well known in the art. While overexpression using a strong non-specific promoter, such as a CMV promoter, can be used, it can be helpful to include a tissue- or cell-type-specific promoter on the expression construct. Further, treatment can include the administration of viral vectors that drive the overexpression of VDAC2 or VDAC1 proteins in infected host cells. Viral vectors are well known to those skilled in the art.

These vectors are readily adapted for use in the methods of the present invention. By the appropriate manipulation using recombinant DNA/molecular biology techniques to insert an operatively linked VDAC2 or VDAC1 encoding nucleic acid segment into the selected expression/delivery vector, many equivalent vectors for the practice of the methods described herein can be generated. It will be appreciated by those of skill in the art that cloned genes readily can be manipulated to alter the amino acid sequence of a protein.

The cloned gene for VDAC2 or VDAC1 can be manipulated by a variety of well-known techniques for in vitro mutagenesis, among others, to produce variants of the naturally occurring human protein, herein referred to as muteins or variants or mutants of VDAC2 or VDAC1, which may be used in accordance with the methods and compositions described herein. The variation in primary structure of muteins of VDAC2 or VDAC1 protein useful in the invention, for instance, may include deletions, additions and substitutions. The substitutions may be conservative or non-conservative. The differences between the natural protein and the mutein generally conserve desired properties, mitigate or eliminate undesired properties and add desired or new properties. The VDAC2 or VDAC1 protein can also be a fusion polypeptide, fused, for example, to a polypeptide that targets the product to a desired location, or, for example, a tag that facilitates its purification, if so desired. Fusion to a polypeptide sequence that increases the stability of the VDAC2 protein is also contemplated. For example, fusion to a serum protein, e.g., serum albumin, can increase the circulating half-life of a VDAC2 or VDAC1 protein. Tags and fusion partners can be designed to be cleavable, if so desired. Another modification specifically contemplated is attachment, e.g., covalent attachment, to a polymer. In one aspect, polymers such as polyethylene glycol (PEG) or methoxypolyethylene glycol (mPEG) can increase the in vivo half-life of proteins to which they are conjugated. Methods of PEGylation of polypeptide agents are well known to those skilled in the art, as are considerations of, for example, how large a PEG polymer to use. In another aspect, biodegradable or absorbable polymers can provide extended, often localized, release of polypeptide agents. Such synthetic bioabsorbable, biocompatible polymers, which may release proteins over several weeks or months can include, for example, poly-α-hydroxy acids (e.g. polylactides, polyglycolides and their copolymers), polyanhydrides, polyorthoesters, segmented block copolymers of polyethylene glycol and polybutylene terephtalate (Polyactive™), tyrosine derivative polymers or poly(ester-amides). Suitable bioabsorbable polymers to be used in manufacturing of drug delivery materials and implants are discussed e.g. in U.S. Pat. Nos. 4,968,317; 5,618,563, among others, and in "Biomedical Polymers" edited by S. W. Shalaby, Carl Hanser Verlag, Munich, Vienna, New York, 1994 and in many references cited in the above publications. The particular bioabsorbable polymer that should be selected will depend upon the particular patient that is being treated.

D. Anti-Arrhythmicity Compound

In another aspect of the present invention, it is provided an anti-arrhythmicity compound of structure of Formula I or a derivative thereof:

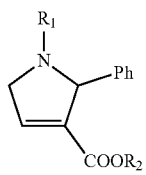

Formula I wherein: $R_1$ is tosyl, or mesyl group; and wherein $R_2$ is a hydrocarbyl group with or without a heteroatom, and wherein the compound is effective to potentiate mitochondrial $Ca^{2+}$ uptake so as to modulate cardiac rhythmicity in a subject, provided that when $R_1$ is tosyl and $R_2$ is ethyl, the compound is in an optionally active (e.g., substantially enantiomerically pure) form Formula Ia or Formula Ib:

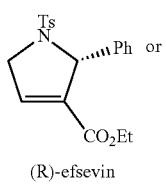

Formula Ia (R)-efsevin

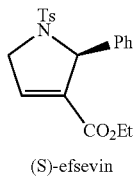

Formula Ib (S)-efsevin

In some embodiments of the invention compound, optionally in combination with any or all of the various embodiments disclosed herein, $R_2$ is methyl, ethyl, C3-C6 short alkyl, or menthyl group.

In some embodiments of the invention compound, optionally in combination with any or all of the various embodiments disclosed herein, $R_2$ is a C1-C10 straight or branched, acyclic or cyclic alkyl group, or aryl group.

In some embodiments of the invention compound, optionally in combination with any or all of the various embodiments disclosed herein, the compound is in an optionally active (e.g., substantially enantiomerically pure) form.

Non-limiting examples of derivatives of Formula I include Formula Ic:

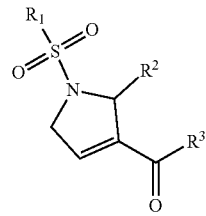

Formula Ic wherein: R1 is an alkane, phenyl, heteroaryl, or substituted phenyl group; R2 is a phenyl, heteroaryl, substituted phenyl, or hydrocarbyl group with or without a heteroatom, and R3 is an alkoxy, amino, or amino ether. Non-limiting examples of a substituted phenyl group is a phenyl group wherein one or more hydrogens are replaced with an alkane, amino, amino ether, or heteroatom.

In some embodiments, R3 is an alkoxy, amino, amino ether, N-Boc-protected 2-aminoethoxyethoxyethylamino group, or a C1-C10 straight or branched, acyclic or cyclic alkyloxy group, aryloxy, or amino group with or without heteroatom In some embodiments, the $R_1$ is para-tolyl, $R_2$ is phenyl, and $R_3$ is ethoxy.

In some embodiments, R3 is ethoxy, menthyloxy, or N-Box-protected 2-aminoethoxyeth-oxyethalamino group.

In some embodiments, there is a method of forming the compound of Formula Ic:

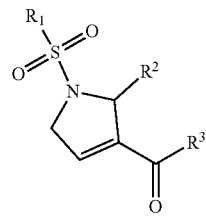

Formula Ic where $R_1$ is substituted phenyl or substituted or unsubstituted heteroaryl; and $R_2$ is substituted phenyl or substituted or unsubstituted heteroaryl; and R3 is $R_3$ is an alkoxy, amino, amino ether, N-Boc-protected 2-aminoethoxyethoxyethylamino group, or a C1-C10 straight or branched, acyclic or cyclic alkyloxy group, aryloxy, or amino group with or without heteroatom comprising reacting

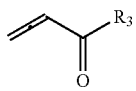

with

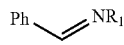

according to a reaction of Scheme I (Scheme I)

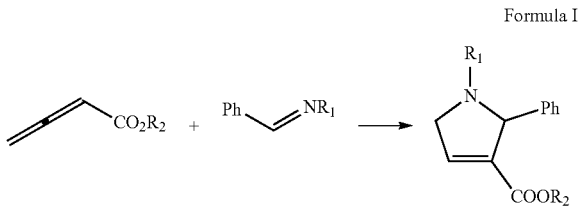

to form the compound of Formula Ic.

In some embodiments, the compound is any one of, (FIG. 16A-B)

E. Method of Synthesis

In a further aspect of the present invention, it is provided a method of forming the compound of Formula I:

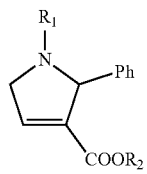

where $R_1$ is tosyl, or mesyl group; and $R_2$ is a hydrocarbyl group with or without a heteroatom, comprising reacting

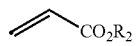

with

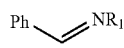

according to a reaction of Scheme I (Scheme I)

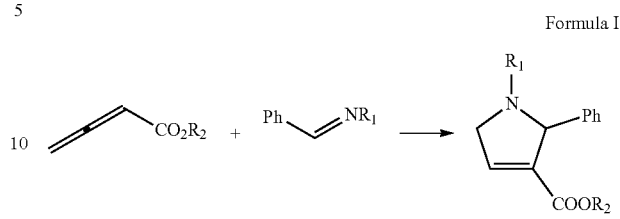

to form the compound of Formula I.

Description of the compound of Formula I is fully provided above. For concise description of the present invention, the description of the compound of Formula I is not repeated here but is fully incorporated hereto by reference.

In some embodiments of the invention method, optionally in combination with any or all of the various embodiments disclosed herein, the reaction of Scheme I is carried out under asymmetric synthesis conditions.

In some embodiments of the invention method, optionally in combination with any or all of the various embodiments disclosed herein, the method further comprises performing chiral resolution of compound of Formula I to yield R- or S-enantiomers of the compound in an optionally active (e.g., substantially enantiomerically pure) form.

In some embodiments of the invention method, optionally in combination with any or all of the various embodiments disclosed herein, the chiral resolution is performed on an HPLC chiral stationary phase.

In some embodiments of the invention method, optionally in combination with any or all of the various embodiments disclosed herein, the chiral resolution is achieved by reacting the compound with a chiral agent.

In some embodiments of the invention method, optionally in combination with any or all of the various embodiments disclosed herein, the chiral agent is menthol.

F. Compositions

In a further aspect of the present invention, it is provided a composition comprising an anti-arrhythmicity compound of Formula I, which is described above. For concise description of the present invention, the description of the compound of Formula I is not repeated here but is fully incorporated hereto by reference.

In some embodiments of the invention composition, optionally in combination with any or all of the various embodiments disclosed herein, the compound is in an optionally active (e.g., substantially enantiomerically pure) form.

In some embodiments of the invention composition, optionally in combination with any or all of the various embodiments disclosed herein, the composition is in a formulation suitable for administration to a subject.

In a further aspect of the present invention, it is provided a method of forming a composition, comprising providing a compound of Formula I in an effective amount, and forming the composition.

The compound of Formula I is fully described above. For concise description of the present invention, the description of the compound of Formula I is not repeated here but is fully incorporated hereto by reference.

In some embodiments of the invention method, optionally in combination with any or all of the various embodiments disclosed herein, the compound is in an optionally active (e.g., substantially enantiomerically pure) form.

In some embodiments of the invention method, optionally in combination with any or all of the various embodiments disclosed herein, the composition is in a formulation suitable for administration to a subject to treat or ameliorate a disorder related to cardiac arrhythmicity, e.g., cardiac fibrillation.

G. Formulations

The compound of invention or composition of invention can be formulated into any desirable formulation. Such formulations can include a pharmaceutically acceptable carrier, which can be, e.g., salient or can comprise a polymeric material.

In some embodiments, the carrier disclosed herein can be a polymeric material. Exemplary polymeric material that can be used here include but are not limited to a biocompatible or bioabsorbable polymer that is one or more of poly($_{D,L}$-lactide), poly($_L$-lactide), poly($_L$-lactide), poly($_L$-lactide-co-$_{D,L}$-lactide), polymandelide, polyglycolide, poly(lactide-co-glycolide), poly($_{D,L}$-lactide-co-glycolide), poly($_L$-lactide-co-glycolide), poly(ester amide), poly(ortho esters), poly(glycolic acid-co-trimethylene carbonate), poly($_{D,L}$-lactide-co-trimethylene carbonate), poly(trimethylene carbonate), poly(lactide-co-caprolactone), poly(glycolide-co-caprolactone), poly(tyrosine ester), polyanhydride, derivatives thereof. In some embodiments, the polymeric material comprises a combination of these polymers.

In some embodiments, the polymeric material comprises poly($_{D,L}$-lactide-co-glycolide). In some embodiments, the polymeric material comprises poly($_{D,L}$-lactide). In some embodiments, the polymeric material comprises poly($_L$-lactide). [0065] Additional exemplary polymers include but are not limited to poly($_D$-lactide) (PDLA), polymandelide (PM), polyglycolide (PGA), poly($_L$-lactide-co-D,L-lactide) (PLDLA), poly($_{D,L}$-lactide) (PDLLA), poly($_{D,L}$-lactide-co-glycolide) (PLGA) and poly($_L$-lactide-co-glycolide) (PLLGA). With respect to PLLGA, the stent scaffolding can be made from PLLGA with a mole % of GA between 5-15 mol %. The PLLGA can have a mole % of (LA:GA) of 85:15 (or a range of 82:18 to 88:12), 95:5 (or a range of 93:7 to 97:3), or commercially available PLLGA products identified as being 85:15 or 95:5 PLLGA. The examples provided above are not the only polymers that may be used. Many other examples can be provided, such as those found in Polymeric Biomaterials, second edition, edited by Severian Dumitriu; chapter 4.

In some embodiments, polymers that are more flexible or that have a lower modulus that those mentioned above may also be used. Exemplary lower modulus bioabsorbable polymers include, polycaprolactone (PCL), poly(trimethylene carbonate) (PTMC), polydioxanone (PDO), poly(3-hydrobutyrate) (PHB), poly(4-hydroxybutyrate) (P4HB), poly(hydroxyalkanoate) (PHA), and poly(butylene succinate), and blends and copolymers thereof.

In exemplary embodiments, higher modulus polymers such as PLLA or PLLGA may be blended with lower modulus polymers or copolymers with PLLA or PLGA. The blended lower modulus polymers result in a blend that has a higher fracture toughness than the high modulus polymer. Exemplary low modulus copolymers include poly($_L$-lactide)-b-polycaprolactone (PLLA-b-PCL) or poly($_L$-lactide)-co-polycaprolactone (PLLA-co-PCL). The composition of a blend can include 1-5 wt % of low modulus polymer.

More exemplary polymers include but are not limited to at least partially alkylated polyethyleneimine (PEI); at least partially alkylated poly(lysine); at least partially alkylated polyornithine; at least partially alkylated poly(amido amine), at least partially alkylated homo- and co-polymers of vinylamine; at least partially alkylated acrylate containing aminogroups, copolymers of vinylamine containing aminogroups with hydrophobic monomers, copolymers of acrylate containing aminogroups with hydrophobic monomers, and amino containing natural and modified polysaccharides, polyacrylates, polymethacryates, polyureas, polyurethanes, polyolefins, polyvinylhalides, polyvinylidenehalides, polyvinylethers, polyvinylaromatics, polyvinylesters, polyacrylonitriles, alkyd resins, polysiloxanes and epoxy resins, and mixtures thereof. Additional examples of biocompatible biodegradable polymers include, without limitation, polycaprolactone, poly($_L$-lactide), poly($_{D,L}$-lactide), poly($_{D,L}$-lactide-co-PEG) block copolymers, poly($_{D,L}$-lactide-co-trimethylene carbonate), poly(lactide-co-glycolide), polydioxanone (PDS), polyorthoester, polyanhydride, poly(glycolic acid-co-trimethylene carbonate), polyphosphoester, polyphosphoester urethane, poly(amino acids), polycyanoacrylates, poly(trimethylene carbonate), poly(iminocarbonate), polycarbonates, polyurethanes, polyalkylene oxalates, polyphosphazenes, PHA-PEG, and combinations thereof. The PHA may include poly(α-hydroxyacids), poly(β-hydroxyacid) such as poly(3-hydroxybutyrate) (PHB), poly(3-hydroxybutyrate-co-valerate) (PHBV), poly(3-hydroxyproprionate) (PHP), poly(3-hydroxyhexanoate) (PHH), or poly(4-hydroxyacid) such as poly poly(4-hydroxybutyrate), poly(4-hydroxyvalerate), poly(4-hydroxyhexanoate), poly(hydroxyvalerate), poly(tyrosine carbonates), poly(tyrosine arylates), poly(ester amide), polyhydroxyalkanoates (PHA), poly(3-hydroxyalkanoates) such as poly(3-hydroxypropanoate), poly(3-hydroxybutyrate), poly(3-hydroxyvalerate), poly(3-hydroxyhexanoate), poly(3-hydroxyheptanoate) and poly(3-hydroxyoctanoate), poly(4-hydroxyalkanaote) such as poly(4-hydroxybutyrate), poly(4-hydroxyvalerate), poly(4-hydroxyhexanote), poly(4-hydroxyheptanoate), poly(4-hydroxyoctanoate) and copolymers including any of the 3-hydroxyalkanoate or 4-hydroxyalkanoate monomers described herein or blends thereof, poly($_{D,L}$-lactide), poly($_L$-lactide), polyglycolide, poly($_{D,L}$-lactide-co-glycolide), poly($_L$-lactide-co-glycolide), polycaprolactone, poly(lactide-co-caprolactone), poly(glycolide-co-caprolactone), poly(dioxanone), poly(ortho esters), poly(anhydrides), poly(tyrosine carbonates) and derivatives thereof, poly(tyrosine ester) and derivatives thereof, poly(imino carbonates), poly(glycolic acid-co-trimethylene carbonate), polyphosphoester, polyphosphoester urethane, poly(amino acids), polycyanoacrylates, poly(trimethylene carbonate), poly(iminocarbonate), polyphosphazenes, silicones, polyesters, polyolefins, polyisobutylene and ethylene-alphaolefin copolymers, acrylic polymers and copolymers, vinyl halide polymers and copolymers, such as polyvinyl chloride, polyvinyl ethers, such as polyvinyl methyl ether, polyvinylidene halides, such as polyvinylidene chloride, polyacrylonitrile, polyvinyl ketones, polyvinyl aromatics, such as polystyrene, polyvinyl esters, such as polyvinyl acetate, copolymers of vinyl monomers with each other and olefins, such as ethylene-methyl methacrylate copolymers, acrylonitrile-styrene copolymers, ABS resins, and ethylene-vinyl acetate copolymers, polyamides, such as Nylon 66 and polycaprolactam, alkyd resins, polycarbonates, polyoxymethylenes, polyimides, polyethers, poly(glyceryl sebacate), poly(propylene fumarate), poly(n-butyl methacrylate), poly(sec-butyl methacrylate), poly(isobutyl methacrylate), poly(tert-butyl methacrylate), poly(n-propyl methacrylate), poly(isopropyl methacrylate), poly(ethyl methacrylate), poly(methyl methacrylate), epoxy resins, polyurethanes, rayon, rayon-triacetate, cellulose acetate, cellulose butyrate, cellulose acetate butyrate, cellophane, cellulose nitrate, cellulose propionate, cellulose ethers, carboxymethyl cellulose, polyethers such as poly(ethylene glycol) (PEG), copoly(ether-esters) (e.g. poly(ethylene oxide-co-lactic acid) (PEO/PLA)), polyalkylene oxides such as poly(ethylene oxide), poly(propylene oxide), poly(ether ester), polyalkylene oxalates, phosphoryl choline containing polymer, choline, poly(aspirin), polymers and co-polymers of hydroxyl bearing monomers such as 2-hydroxyethyl methacrylate (HEMA), hydroxypropyl methacrylate (HPMA), hydroxypropylmethacrylamide, PEG acrylate (PEGA), PEG methacrylate, methacrylate polymers containing 2-methacryloyloxyethyl-phosphorylcholine (MPC) and n-vinyl pyrrolidone (VP), carboxylic acid bearing monomers such as methacrylic acid (MA), acrylic acid (AA), alkoxymethacrylate, alkoxyacrylate, and 3-trimethylsilylpropyl methacrylate (TMSPMA), poly(styrene-isoprene-styrene)-PEG (SIS-PEG), polystyrene-PEG, polyisobutylene-PEG, polycaprolactone-PEG (PCL-PEG), PLA-PEG, poly(methyl methacrylate), MED610, poly(methyl methacrylate)-PEG (PMMA-PEG), polydimethylsiloxane-co-PEG (PDMS-PEG), poly(vinylidene fluoride)-PEG (PVDF-PEG), PLURONIC™ surfactants (polypropylene oxide-co-polyethylene glycol), poly(tetramethylene glycol), hydroxy functional poly(vinyl pyrrolidone), biomolecules such as collagen, chitosan, alginate, fibrin, fibrinogen, cellulose, starch, dextran, dextrin, hyaluronic acid, fragments and derivatives of hyaluronic acid, heparin, fragments and derivatives of heparin, glycosamino glycan (GAG), GAG derivatives, polysaccharide, elastin, elastin protein mimetics, or combinations thereof.

In some embodiments, polyethylene is used to construct at least a portion of the device. For example, polyethylene can be used in an orthopedic implant on a surface that is designed to contact another implant, as such in a joint or hip replacement. Polyethylene is very durable when it comes into contact with other materials. When a metal implant moves on a polyethylene surface, as it does in most joint replacements, the contact is very smooth and the amount of wear is minimal. Patients who are younger or more active may benefit from polyethylene with even more resistance to wear. This can be accomplished through a process called crosslinking, which creates stronger bonds between the elements that make up the polyethylene. The appropriate amount of crosslinking depends on the type of implant. For example, the surface of a hip implant may require a different degree of crosslinking than the surface of a knee implant.

Additional examples of polymeric materials can be found, for example, in U.S. Pat. No. 6,127,448 to Domb, US Pat. Pub. No. 2004/0148016 by Klein and Brazil, US Pat. Pub. No. 2009/0169714 by Burghard et al, U.S. Pat. No. 6,406,792 to Briquet et al, US Pat. Pub. No. 2008/0003256 by Martens et al, each of which is hereby incorporated by reference herein in its entirety.

H. Dosage and Administration

The dosage can be determined by one of skill in the art and can also be adjusted by the individual physician in the event of any complication. Typically, the dosage ranges from 0.0005 mg/kg body weight to 1 g/kg body weight. In some embodiments, the dosage range is from 0.001 mg/kg body weight to 0.5 g/kg body weight, from 0.0005 mg/kg body weight to 0.1 g/kg body weight, from 0.001 mg/kg body weight to 0.05 g/kg body weight.

As another alternative, dosages are selected for localized delivery and are not necessarily selected for body weight or to achieve a certain serum level, but to achieve a localized effect, e.g., as for a localized injection, implantation or other localized administration to the eye.

Administration of the doses recited above can be repeated for a limited period of time. In some embodiments, the doses are given once a day, or multiple times a day, for example, but not limited to, three times a day. In a preferred embodiment, the doses recited above are administered daily for several weeks or months. The duration of treatment depends upon the subject's clinical progress and responsiveness to therapy. Continuous, relatively low maintenance doses are contemplated after an initial higher therapeutic dose.

Agents useful in the methods and compositions described herein can be administered topically, intravenously (by bolus or continuous infusion), orally, by inhalation, intraperitoneally, intramuscularly, subcutaneously, intracavity, and can be delivered by peristaltic means, if desired, or by other means known by those skilled in the art. It is preferred that the agents for the methods described herein are administered topically to the eye. For the treatment of tumors, the agent can be administered systemically, or alternatively, can be administered directly to the tumor e.g., by intratumor injection or by injection into the tumor's primary blood supply.

Therapeutic compositions containing at least one agent disclosed herein can be conventionally administered in a unit dose. The term "unit dose" when used in reference to a therapeutic composition refers to physically discrete units suitable as unitary dosage for the subject, each unit containing a predetermined quantity of active material calculated to produce the desired therapeutic effect in association with the required physiologically acceptable diluent, i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. An agent can be targeted by means of a targeting moiety, such as e.g., an antibody or targeted liposome technology.

Precise amounts of active ingredient required to be administered depend on the judgment of the practitioner and are particular to each individual. However, suitable dosage ranges for systemic application are disclosed herein and depend on the route of administration. Suitable regimes for administration are also variable, but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

An agent may be adapted for catheter-based delivery systems including coated balloons, slow-release drug-eluting stents or other drug-eluting formats, microencapsulated PEG liposomes, or nanobeads for delivery using direct mechanical intervention with or without adjunctive techniques such as ultrasound, together with an active agent as described herein, dissolved or dispersed therein as an active ingredient. In a preferred embodiment, the therapeutic composition is not immunogenic when administered to a mammal or human patient for therapeutic purposes. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions; however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at a physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, and publications identified are expressly incorporated herein by reference for the purpose of describing and disclosing, for example, the methodologies described in such publications that might be used in connection with the present invention.

These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

The following examples illustrate rather than limit the embodiments of the present invention.

Example 1

Studies on Mitochondrial $Ca^{2+}$ Uptake by the Voltage-Dependent Anion Channel 2 Regulates Cardiac Rhythmicity A. Summary Tightly regulated $Ca^{2+}$ homeostasis is a prerequisite for proper cardiac function. To dissect the regulatory network of cardiac $Ca^{2+}$ handling, we performed a chemical suppressor screen on zebrafish tremblor embryos, which suffer from $Ca^{2+}$ extrusion defects. Efsevin was identified based on its potent activity to restore coordinated contractions in tremblor. We show that efsevin binds to VDAC2, potentiates mitochondrial $Ca^{2+}$ uptake and accelerates the transfer of $Ca^{2+}$ from intracellular stores into mitochondria. In cardiomyocytes, efsevin restricts the temporal and spatial boundaries of $Ca^{2+}$ sparks and thereby inhibits $Ca^{2+}$ overload-induced erratic $Ca^{2+}$ waves and irregular contractions. We further show that overexpression of VDAC2 recapitulates the suppressive effect of efsevin on tremblor embryos whereas VDAC2 deficiency attenuates efsevin's rescue effect and that VDAC2 functions synergistically with MCU to suppress cardiac fibrillation in tremblor. Together, these findings demonstrate a critical modulatory role for VDAC2-dependent mitochondrial $Ca^{2+}$ uptake in the regulation of cardiac rhythmicity.

B. Introduction

During development, well-orchestrated cellular processes guide cells from diverse lineages to integrate into the primitive heart tube and establish rhythmic and coordinated contractions. While many genes and pathways important for cardiac morphogenesis have been identified, molecular mechanisms governing embryonic cardiac rhythmicity are poorly understood. The findings that Ca2+ waves traveling across the heart soon after the formation of the primitive heart tube (Chi et al., 2008, PLoS Biol 6, e109) and that loss of function of key Ca2+ regulatory proteins, such as the L-type Ca2+ channel, Na/K-ATPase and sodium-calcium exchanger 1 (NCX1), severely impairs normal cardiac function (Rottbauer et al., 2001, Dev Cell 1, 265-275; Shu et al., 2003, Development 130, 6165-6173; Ebert et al., 2005, Proc Natl Acad Sci USA 102, 17705-17710; Langenbacher et al., 2005, Proc Natl Acad Sci USA 102, 17699-17704), indicate an essential role for Ca2+ handling in the regulation of embryonic cardiac function.

$Ca^{2+}$ homoeostasis in cardiac muscle cells is tightly regulated at the temporal and spatial level by a subcellular network involving multiple proteins, pathways, and organelles. The release and reuptake of $Ca^{2+}$ by the sarcoplasmic reticulum (SR), the largest $Ca^{2+}$ store in cardiomyocytes, constitutes the primary mechanism governing the contraction and relaxation of the heart. $Ca^{2+}$ influx after activation of the L-type $Ca^{2+}$ channel in the plasma membrane induces the release of $Ca^{2+}$ from the SR via ryanodine receptor (RyR) channels, which leads to an increase of the intracellular $Ca^{2+}$ concentration and cardiac contraction. During diastolic relaxation, $Ca^{2+}$ is transferred back into the SR by the SR $Ca^{2+}$ pump or extruded from the cell through NCX1. Defects in cardiac $Ca^{2+}$ handling and $Ca^{2+}$ overload, for example during cardiac ischemia/reperfusion or in long QT syndrome, are well known causes of contractile dysfunction and many types of arrhythmias including early and delayed afterdepolarizations and Torsade des pointes (Bers, 2002, Nature 415, 198-205; Choi et al., 2002, J Physiol 543, 615-631; Yano et al., 2008, Circ J 72, A22-30; Greiser et al., 2011, Cardiovasc Res 89, 722-733).

$Ca^{2+}$ crosstalk between mitochondria and ER/SR has been noted in many cell types and the voltage-dependent anion channel (VDAC) and the mitochondrial $Ca^{2+}$ uniporter (MCU) serve as primary routes for $Ca^{2+}$ entry through the outer and inner mitochondrial membranes, respectively (Rapizzi et al., 2002, J Cell Biol 159, 613-624; Bathori et al., J Biol Chem 2006, 281, 17347-17358; Shoshan-Barmatz et al., 2010, Mol Aspects Med 31, 227-285; Baughman et al., 2011, Nature 476, 341-345; De Stefani et al., 2011, Nature 476, 336-340). In the heart, mitochondria are tethered to the SR and are located in close proximity to $Ca^{2+}$ release sites (Garcia-Perez et al., 2008, J Biol Chem 283, 32771-32780; Boncompagni et al., 2009, Mol Biol Cell 20, 1058-1067; Hayashi et al., 2009, J Cell Sci 122, 1005-1013). This subcellular architecture exposes the mitochondria near the $Ca^{2+}$ release sites to a high local $Ca^{2+}$ concentration that is sufficient to overcome the low $Ca^{2+}$ affinity of MCU and facilitates $Ca^{2+}$ crosstalk between SR and mitochondria (Garcia-Perez et al., 2008; Dorn et al., 2010, Circ Res 107, 689-699; Kohlhaas et al., 2013, Cardiovasc Res 98, 259-268). Increase of the mitochondrial $Ca^{2+}$ concentration enhances energy production during higher workload and dysregulation of SR-mitochondrial $Ca^{2+}$ signaling results in energetic deficits and oxidative stress in the heart and may trigger programmed cell death (Brandes et al., 1997, Circ Res 80, 82-87; Maack et al., 2006, Circ Res 99, 172-182; Kohlhaas et al., 2013). However, whether SR-mitochondrial $Ca^{2+}$ crosstalk also contributes significantly to cardiac $Ca^{2+}$ signaling during excitation-contraction coupling requires further investigation.

In zebrafish, the tremblor (tre) locus encodes a cardiac-specific isoform of the Na+/Ca2+ exchanger 1, NCX1h (also known as slc8a1a) (Ebert et al., 2005; Langenbacher et al., 2005). The tre mutant hearts lack rhythmic Ca2+ transients and display chaotic Ca2+ signals in the myocardium leading to unsynchronized contractions resembling cardiac fibrillation (Langenbacher et al., 2005). In this study, we used tre as an animal model for aberrant Ca2+ handling-induced cardiac dysfunction and took a chemical genetic approach to dissect the Ca2+ regulatory network important for maintaining cardiac rhythmicity. A synthetic compound named efsevin was identified from a suppressor screen due to its potent ability to restore coordinated contractions in tre. Using biochemical and genetic approaches we show that efsevin interacts with VDAC2 and potentiates its mitochondrial Ca2+ transporting activity and spatially and temporally modulates cytosolic Ca2+ signals in cardiomyocytes. The important role of mitochondrial Ca2+ uptake in regulating cardiac rhythmicity is further supported by the suppressive effect of VDAC2 and MCU overexpression on cardiac fibrillation in tre.

C. Materials and Methods

Zebrafish Husbandry and Transgenic Lines.

Zebrafish of the mutant line tremblor ($tre^{tc318}$) were maintained and bred as described previously (Langenbacher et al., 2005). Transgenic lines, $myl7:gCaMP4.1^{L2124}$ and $myl7:VDAC2^{LA2309}$ were created using the Tol2kit (Esengil et al., 2007, Nat Chem Biol 3, 154-155; Kwan et al., 2007, Dev Dyn 236, 3088-3099; Shindo et al., 2010, PLoS One 5, e8897). The $VDAC2^{LA2256}$ was created using the zinc finger array OZ523 and OZ524 generated by the zebrafish Zinc Finger Consortium (Foley et al., 2009a, Nature protocols 4, 1855-1867; Foley et al., 2009b, PLoS One 4, e4348).

Molecular Biology.

Full length VDAC2 cDNA was purchased from Open Biosystems and cloned into pCS2+ or pCS2+3XFLAG. Full length cDNA fragments of zebrafish MCU (Accession number: JX424822) and MICU1 (JX42823) were amplified from 2 dpf embryos and cloned into pCS2+. For mRNA synthesis, plasmids were linearized and mRNA was synthesized using the SP6 mMESSAGE mMachine kit according to the manufacturers manual (Ambion).

Zebrafish Injections.

VDAC2 mRNA and morpholino antisense oligos (5'-GGGAACGGCCATTTTATCTGTTAAA-3') (Genetools) (SEQ ID NO: 9) were injected into one-cell stage embryos collected from crosses of $tre^{tc318}$ heterozygotes. Cardiac performance was analyzed by visual inspection on 1 dpf. The tre mutant embryos were identified either by observing the fibrillation phenotype at 2-3 dpf or by genotyping as previously described (Langenbacher et al., 2005).

Chemical Screen.

Chemicals from a synthetic library (Castellano et al., 2007, J Am Chem Soc 129, 5843-5845; Choi et al., 2011, Development 138, 1173-1181; Cruz et al., 2011, Proc Natl Acad Sci USA 108, 6769-6774) and from Biomol International LP were screened for their ability to partially or completely restore persistent heartbeat in tre embryos. 12 embryos collected from crosses of $tre^{tc318}$ heterozygotes were raised in the presence of individual compounds at a concentration of 10 μM from 4 hpf (Choi et al., 2011). Cardiac function was analyzed by visual inspection at 1 and 2 dpf. The hearts of $tre^{tc318}$ embryos manifest a chaotic movement resembling cardiac fibrillation with intermittent contractions in rare occasion (Ebert et al., 2005; Langenbacher et al., 2005). Compounds that elicit persistent coordinated cardiac contractions were validated on large number of tre mutant embryos and NCX1h morphants (>500 embryos).

Zebrafish Cardiac Imaging.

Movies of GFP-labelled myl7:GFP hearts were taken at 30 frames per second. Line-scan analysis was performed along a line through the atria or the ventricles of these hearts (Nguyen et al., 2009, Drug Discovery Today: Disease Models 5). Fraction of shortening was deduced from the ratio of diastolic and systolic width and heart rate was determined by beats per minute. Cardiac parameters were analyzed in $tremblor^{tc318}$ and $VDAC2^{LA2256}$ at 2 dpf.

Zebrafish Optical Mapping.

36 hpf myl7:gCaMP4.1 embryos were imaged at a frame rate of 30 ms/frame. Electromechanical isolation was achieved by tnnt2MO (Milan et al., 2006, Development 133, 1125-1132). The fluorescence intensity of each pixel in a 2D map was normalize to generate heat maps and isochronal lines at 33 ms intervals were obtained by identifying the maximal spatial gradient for a given time point (Chi et al., 2008).

Mouse and Human Embryonic Stem Cells.

The mouse E14Tg2a ESC and human H9 ESC line were cultured and differentiated as previously described (Blin et al., 2010, J Clin Invest 120, 1125-1139; Arshi et al., 2013, Sci Technol Adv Mater 2013, 025003). At day 10 of differentiation, beating mouse EBs were exposed to external solution containing 10 mM $CaCl_2$ for 10 minutes before DMSO or efsevin (10 µM) treatment. Human EBs were differentiated for 15 days and treated with 5 mM $CaCl_2$) for 10 minutes before DMSO or efsevin (5 µM) treatment. Images of beating EBs were acquired at a rate of 30 frames/sec and analyzed by motion-detection software. For calcium recording, the EBs were loaded with 10 µM fluo-4 AM in culture media for 30 minutes at 37° C. Line-scan analysis was performed and fluorescent signals were acquired by a Zeiss LSM510 confocal microscope.

Microelectrode Array Measurements.

Two-day-old wild type, tre, and efsevin-treated tre embryos were placed on uncoated, microelectrode arrays (MEAs) containing 120 integrated TiN electrodes (30 µm diameter, 200 µm interelectrode spacing). Local field potentials (LFPs) at each electrode were collected for three trials per embryo type over a period of three minutes at a sampling rate of 1 kHz using the MEA2100-HS120 system (Multichannel Systems, Reutiligen, Germany). Raw data was low-pass filtered at a cutoff frequency of 10 Hz using a third-order Butterworth filter. Data analysis was carried out using the MC_DataTool (Multichannel Systems) and Matlab (MathWorks).

$Ca^{2+}$ imaging.

Murine ventricular cardiomyocytes were isolated as previously described (Reuter et al., 2004, J Physiol 554, 779-789). Cells were loaded with 5 µM fluo-4 AM in external solution containing: 138.2 mM NaCl, 4.6 mM KCl, 1.2 mM $MgCl$, 15 mM glucose, 20 mM HEPES for 1 hr and imaged in external solution supplemented with 2, 5 or 10 mM $CaCl_2$). For the recording of $Ca^{2+}$ sparks and transients, the external solution contained 2 mM $CaCl_2$. For $Ca^{2+}$ transients, cells were field stimulated at 0.5 Hz with a 5 ms pulse at a voltage of 20% above contraction threshold. For all measurements, efsevin was added 2 hours prior to the actual experiment. Images were recorded on a Zeiss LSM 5 Pascal confocal microscope. Data analysis was carried out using the Zeiss LSM Image Browser and ImageJ with the SparkMaster plugin (Picht et al., 2007, Am J Physiol Cell Physiol 293, C1073-1081). Cells were visually inspected prior to and after each recording. Only those recordings from healthy looking cells with distinct borders, uniform striations and no membrane blebs or granularity were included in the analysis.

Biochemistry.

For pull down assays mono-N-Boc protected 2,2'-(ethylenedioxy)bis(ethylamine) was attached to the carboxylic ester of efsevin and its derivatives through the amide bond. After removal of the Boc group using TFA, the primary amine was coupled to the carboxylic acid of Affi-Gel 10 Gel (Biorad). Two-day-old zebrafish embryos were deyolked by centrifugation before being lysed with Rubinfeld's lysis buffer (Rubinfeld et al., 1993, Science 262, 1731-1734). The lysate was precleaned by incubation with Affi-Gel 10 Gel to eliminate non-specific binding. Precleaned lysate was incubated with affinity beads overnight. Proteins were eluted from the affinity beads and separated on SDS-PAGE. Protein bands of interest were excised. Gel plugs were dehydrated in acetonitrile (ACN) and dried completely in a Speedvac. Samples were reduced and alkylated with 10 mM dithiotreitol and 10 mM TCEP solution in 50 mM $NH_4HCO_3$ (30 min at 56° C.) and 100 mM iodoacetamide (45 min in dark), respectively. Gel plugs were washed with 50 mM $NH_4HCO_3$, dehydrated with ACN, and dried down in a Speedvac. Gel pieces were then swollen in digestion buffer containing 50 mM $NH_4HCO_3$, and 20.0 ng/µL of chymotrypsin (25° C., overnight). Peptides were extracted with 0.1% TFA in 50% ACN solution, dried down and resuspended in LC buffer A (0.1% formic acid, 2% ACN).

Mass Spectrometry Analyses and Database Searching.

Extracted peptides were analyzed by nano-flow LC/MS/MS on a Thermo Orbitrap with dedicated Eksigent nanopump using a reversed phase column (New Objective). The flow rate was 200 nL/min for separation: mobile phase A contained 0.1% formic acid, 2% ACN in water, and mobile phase B contained 0.1% formic acid, 20% water in ACN. The gradient used for analyses was linear from 5% B to 50% B over 60 min, then to 95% B over 15 min, and finally keeping constant 95% B for 10 min. Spectra were acquired in data-dependent mode with dynamic exclusion where the instrument selects the top six most abundant ions in the parent spectra for fragmentation. Data were searched against the *Danio rerio* IPI database v3.45 using the SEQUEST algorithm in the BioWorks software program version 3.3.1 SP1. All spectra used for identification had deltaCN>0.1 and met the following Xcorr criteria: >2 (+1), >3 (+2), >4 (+3), and >5 (+4). Searches required full cleavage with the enzyme, ≤4 missed cleavages and were performed with the differential modifications of carbamidomethylation on cysteine and methionine oxidation.

In Situ Hybridization.

In situ hybridization was performed as previously described (Chen et al., 1996, Development 122, 3809-3816). DIG-labeled RNA probe was synthesized using the DIG RNA labeling kit (Roche).

Immunostaining.

HeLa cells were transfected with a C-terminally flag-tagged zebrafish VDAC1 or VDAC2 in plasmid pCS2+ using Lipofectamine™ 2000 (Invitrogen). After staining with MitoTracker® Orange (Invitrogen) cells were fixed in 3.7% formaldehyde and permeabilized with acetone. Immunostaining was performed using primary antibody ANTI-FLAG® M2 (Sigma Aldrich) at 1:100 and secondary antibody Anti-Mouse IgG1-FITC (Southern Biotechnology Associates) at 1:200. Cells were mounted and counterstained using Vectashield® Hard Set™ with DAPI (Vector Laboratories).

Mitochondria $Ca^{2+}$ Uptake Assay in HeLa Cells.

HeLa cells were transfected with zebrafish VDAC2 using Lipofectamine™ 2000 (Invitrogen). 36 hrs after transfection, cells were loaded with 5 µM Rhod2-AM (Invitrogen), a $Ca^{2+}$ indicator preferentially localized in mitochondria, for 1 hour at 15° C. followed by a 30 min de-esterification period at 37° C. Subsequently, cells were permeabilized with 100 µM digitonin for 1 min at room temperature. Fluorescence changes in Rhod2 (ex: 544 nm, em: 590 nm) immediately after the addition of $Ca^{2+}$ (final free $Ca^{2+}$ concentration is calculated to be approximately 10 µM using WEBMAXC at http://web.stanford.edu/~cpatton/webmaxcS.htm) were monitored in internal buffer (5 mM K-EGTA, 20 mM HEPES, 100 mM K-aspartate, 40 mM KCl, 1 mM $MgCl_2$, 2 mM maleic acid, 2 mM glutamic acid, 5 mM pyruvic acid, 0.5 mM $KH_2PO_4$, 5 mM MgATP, pH adjusted to 7.2 with Trizma base) using a FLUOSTAR plate reader (BMG Labtech).

Mitochondria $Ca^{2+}$ Uptake Assay in VDAC1/VDAC3 Double Knockout (V1/V3 DKO) MEFs.

V1/V3 DKO MEFs were cultured as previously described (Roy et al., 2009a, EMBO Rep 10, 1341-1347). Efsevin-treated (15 µM for 30 min) or mock-treated MEFs were used for measurements of $[Ca^{2+}]_c$ in suspensions of permeabilized cells or imaging of $[Ca^{2+}]_m$ simultaneously with $[Ca^{2+}]_c$ in intact single cells. Permeabilization of the plasma membrane was performed by digitonin (40 µM/ml). Changes in $[Ca^{2+}]$ in the cytoplasmic buffer upon $IP_3$ (7.5 µM) addition in the presence or absence of ruthenium red (3 µM) was measured by fura2 in a fluorometer (Csordas et al., 2006, J Cell Biol 174, 915-921; Roy et al., 2009b, Mol Cell 33, 377-388). To avoid endoplasmic reticulum $Ca^{2+}$ uptake 2 µM thapsigargin was added before $IP_3$. For imaging of $[Ca^{2+}]_m$ and $[Ca^{2+}]_c$, MEFs were co-transfected with plasmids encoding polycistronic zebrafish VDAC2 with mCherry and mitochondria-targeted inverse pericam for 40 hours. Cells were sorted to enrich the transfected cells and attached to glass coverslips. In the final 10 min, of the efsevin or mock-treatment, the cells were also loaded with fura2AM (2.5µ□) and subsequently transferred to the microscope stage. Stimulation with 1 µM ATP was carried out in a norminally $Ca^{2+}$ free buffer. Changes in $[Ca^{2+}]_c$ and $[Ca^{2+}]_m$ were imaged using fura2 (ratio of ex: 340 nm to 380 nm) and mitochondria-targeted inverse pericam (ex: 495 nm), respectively (Csordas et al., 2010, Mol Cell 39, 121-132).

Statistics.

All values are expressed as mean±SEM. Significance values are calculated by unpaired student's t-test unless noted otherwise.

Test data not shown include the following information:
1) a heart of a wild-type zebrafish embryo at 2 dpf. Robust rhythmic contractions can be observed in atrium and ventricle.
2) a heart of a tremblor embryo at 2 dpf. Embryos of the mutant line tremblor display only local, unsynchronized contractions, comparable to cardiac fibrillation.
3) a heart of a tremblor embryo at 2 dpf treated with efsevin. Treatment of tremblor embryos with efsevin restores rhythmic contractions with comparable atrial fractional shortening compared to wild-type embryos and approximately 40% of wild-type heart rate.
4) a heart of a wild-type zebrafish embryo at 2 dpf treated with efsevin. Treatment of wild-type embryos with efsevin did not affect cardiac performance, indicated by robust, rhythmic contractions comparable to untreated wild-type embryos.
5) heat map of $Ca^{2+}$ transients recorded in one day old wild type heart.
6) heat map of $Ca^{2+}$ transients recorded in one day old tremblor heart.
7) heat map of $Ca^{2+}$ transients recorded in one day old efsevin treated tremblor heart.
8) a heart of a wild-type zebrafish embryo at 1 dpf. Robust rhythmic contractions can be observed in atrium and ventricle.
9) a heart of a wild-type zebrafish embryo injected with zebrafish VDAC2 mRNA at 1 dpf. Robust rhythmic contractions can be observed in atrium and ventricle.
10) a heart of a tremblor embryo at 1 dpf. Tremblor embryos display only local, unsynchronized contractions, comparable to cardiac fibrillation.
11) a heart of a tremblor embryo injected with zebrafish VDAC2 mRNA at 1 dpf. Overexpression of zebrafish VDAC2 mRNA restores rhythmic contractions in tremblor embryos.
12) a heart of a 2 dpf Tg-VDAC2 embryo injected with a morpholino targeting NCX1h. Morpholino knockdown of NCX1h results in a fibrillating heart.
13) a heart of a 2 dpf NCX1h morphant in the Tg-VDAC2 genetic background. TBF treatment induces VDAC2 expression and restores coordinated cardiac contractions.
14) a heart of a 2 dpf wild type zebrafish embryo injected with a morpholino targeting VDAC2. Morpholino knockdown of VDAC2 did not have obvious effects on cardiac performance.
15) a heart of a 2 dpf tremblor mutant embryo injected with a morpholino targeting VDAC2.
16) a heart of a 2 dpf tremblor mutant embryo injected with a morpholino targeting VDAC2. Efsevin treatment cannot restore coordinated cardiac contractions in the absence of VDAC2.

D. Results and Discussion

Identification of a Chemical Suppressor of Tre Cardiac Dysfunction

Figure 1B:
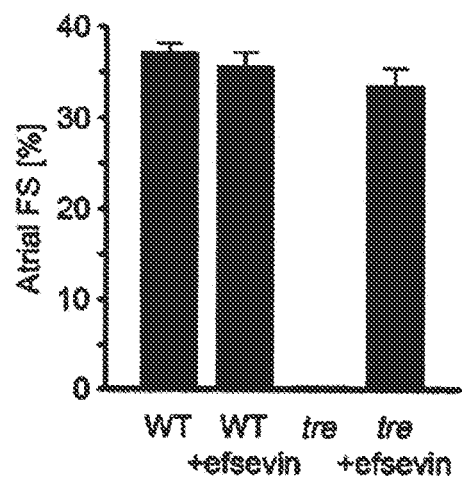
Figure 1C:
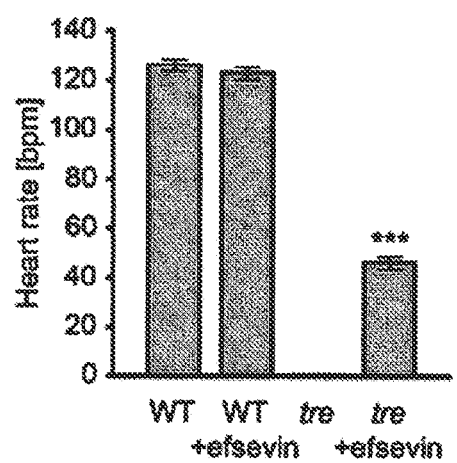
Figure 1D:
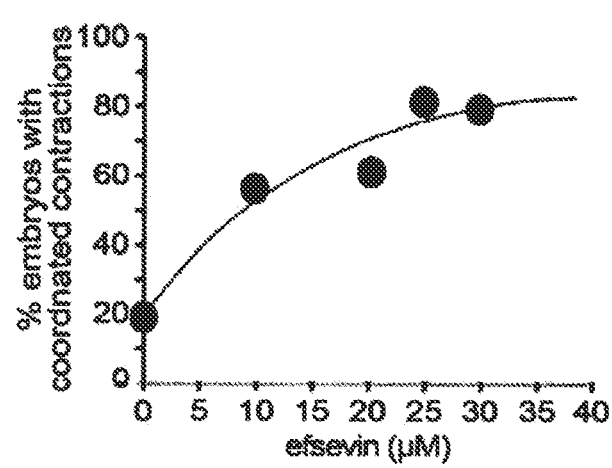
Figure 1E:
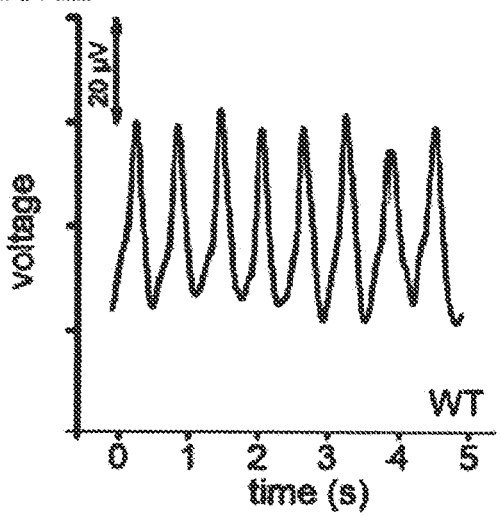
Figure 1F:
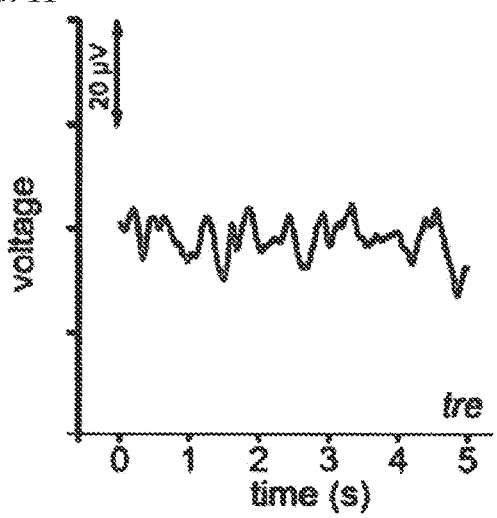
Figure 1G:
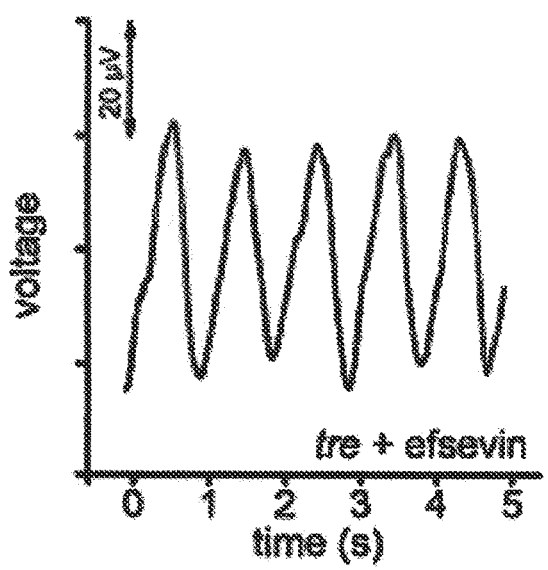

Homozygous tre mutant embryos suffer from Ca2+ extrusion defects and manifest chaotic cardiac contractions resembling fibrillation (Ebert et al., 2005; Langenbacher et al., 2005). To dissect the regulatory network of Ca2+ handling in cardiomyocytes and to identify mechanisms controlling embryonic cardiac rhythmicity, we screened the BioMol library and a collection of synthetic compounds for chemicals that are capable of restoring heartbeat either completely or partially in tre embryos. A dihydropyrrole carboxylic ester compound named efsevin was identified based on its ability to restore persistent and rhythmic cardiac contractions in tre mutant embryos in a dose-dependent manner (FIG. 1D). To validate the effect of efsevin, we assessed cardiac performance of wild type, tre and efsevin-treated tre embryos (Nguyen et al., 2009). Line scans across the atria of Tg(myl7:GFP) embryonic hearts at 48 hpf showed rhythmically alternating systoles and diastoles from vehicle- or efsevin-treated wild type and efsevin-treated tre embryos, while only sporadic unsynchronized contractions were seen from vehicle-treated tre embryos. Fractional shortening of efsevin treated tre mutant hearts was comparable to that of their wild type siblings and heart rate was restored to approximately 40% of that observed in controls (FIG. 1A-C). Periodic local field potentials accompanying each heartbeat were detected in wild type and efsevin-treated tre embryos using a microelectrode array (FIG. 1E-G). Furthermore, while only sporadic $Ca^{2+}$ signals were detected in tre hearts, in vivo $Ca^{2+}$ imaging revealed steady $Ca^{2+}$ waves propagating through efsevin-treated tre hearts, demonstrating that cardiomyocytes are functionally coupled and that efsevin treatment restores regular $Ca^{2+}$ transients in tre hearts.

Efsevin Suppresses $Ca^{2+}$ Overload-Induced Irregular Contraction

Figure 2A:
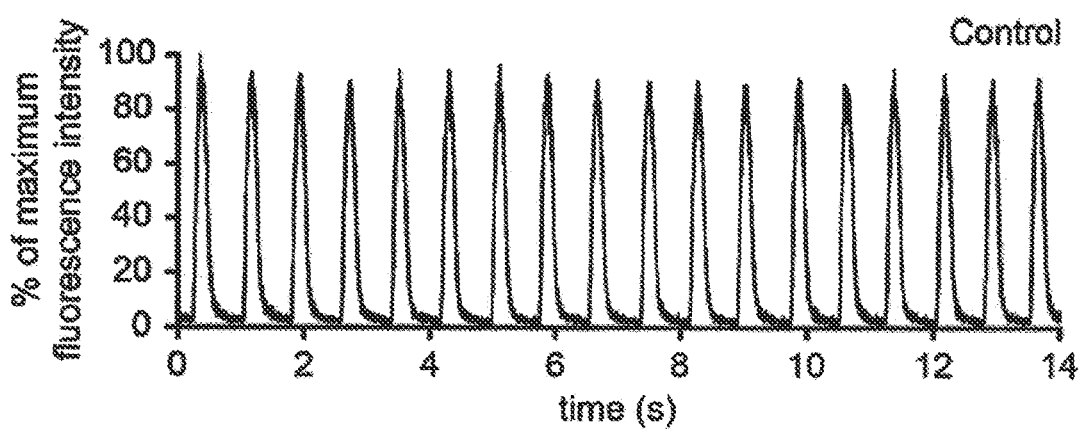
FIGS. 2A-2F show test results demonstrating efsevin reduces arrhythmogenic events in ES cell-derived cardiomyocytes (A-D). Representative graph of rhythmic $Ca^{2+}$ transients detected in mESC-CMs of line-scan analysis of $Ca^{2+}$ transients in mESC-CMs after 10 days of differentiation (A). After treatment with 10 mM $Ca^{2+}$ for 10 minutes, the EB showed an irregular pattern of $Ca^{2+}$ transients (B). Efsevin treatment restores regular $Ca^{2+}$ transients under $Ca^{2+}$ overload conditions in mESC-CMs (C). (D) Plotted intervals between peaks of $Ca^{2+}$ signals detected in mESC-CMs prior to treatment (control), in 10 mM $Ca^{2+}_{ext}$ ($Ca^{2+}$) and in 10 mM $Ca^{2+}_{ext}$+10 μM efsevin ($Ca^{2+}$+ efsevin). (E,F) Plotted intervals of contractions detected in EBs prior to treatment (control), in 10 mM $Ca^{2+}_{ext}$ ($Ca^{2+}$) and in 10 mM $Ca^{2+}_{ext}$+10 μM efsevin ($Ca^{2+}$+ efsevin) for mouse ESC-CMs (E) and 5 mM $Ca^{2+}_{ext}$ ($Ca^{2+}$) and in 5 mM $Ca^{2+}_{ext}$+5 μM efsevin ($Ca^{2+}$+ efsevin) for human ESC-CMs (F). ***, p<0.001 by F-test.
Figure 2B:
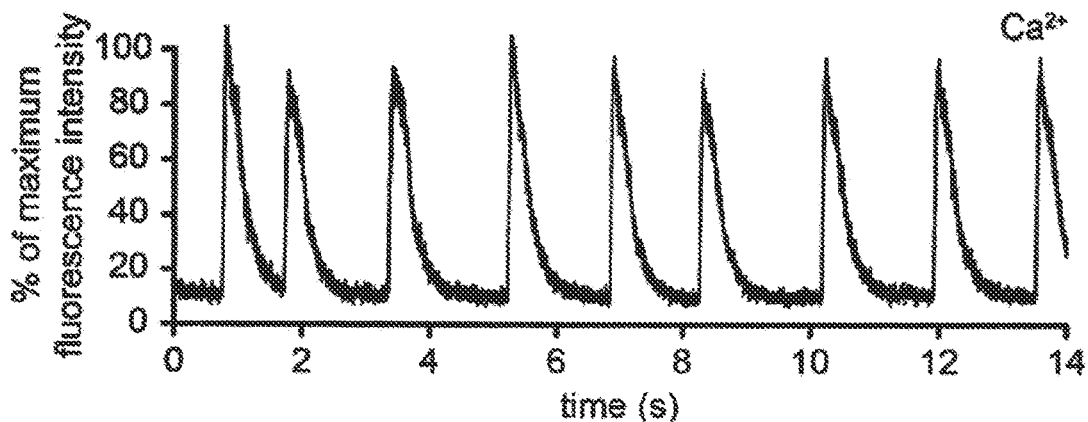
Figure 2C:
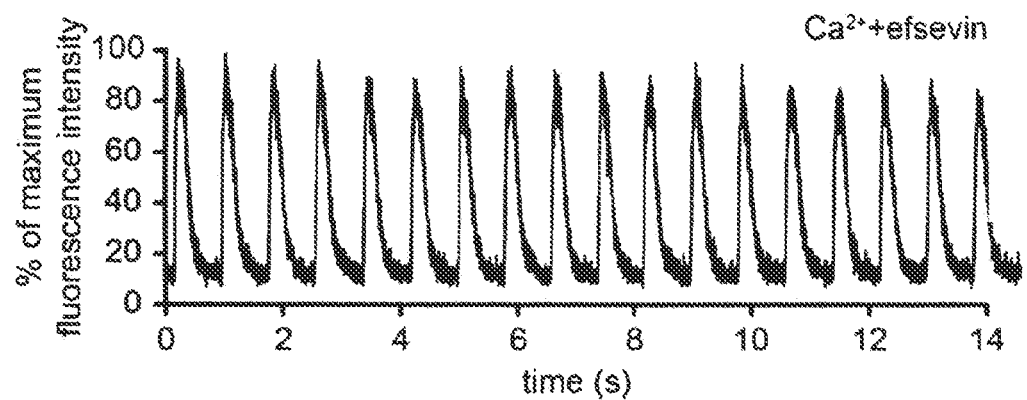
Figure 2D:
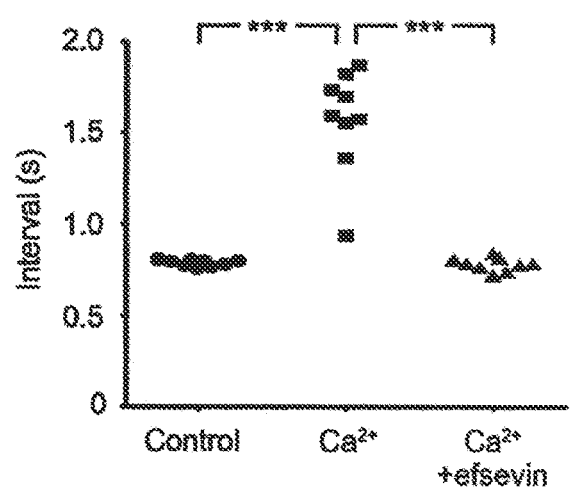
Figure 2E:
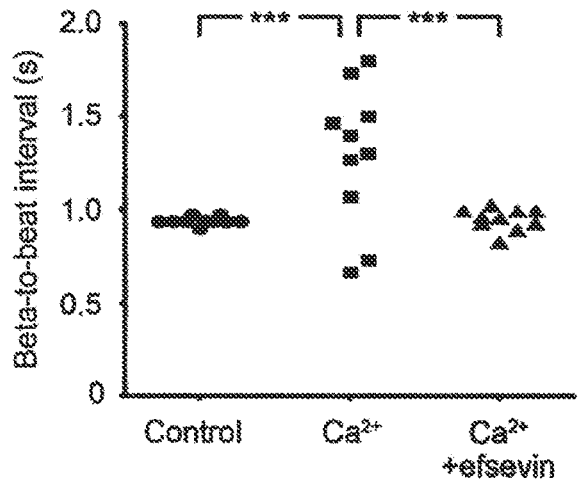
Figure 2F:
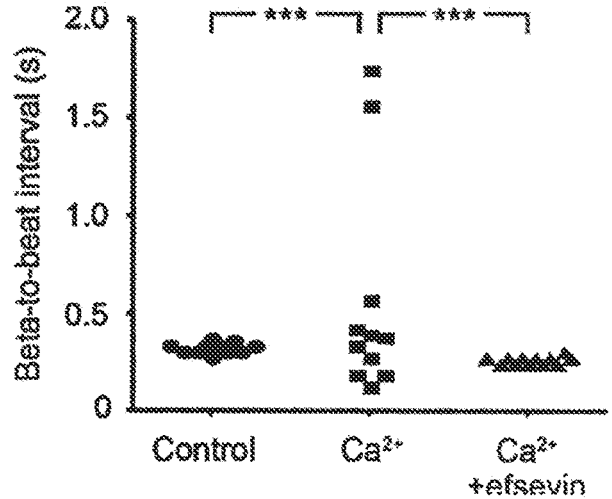

We next examined whether efsevin could suppress aberrant Ca2+ homeostasis-induced arrhythmic responses in mammalian cardiomyocytes. Mouse embryonic stem cell-derived cardiomyocytes (mESC-CMs) establish a regular contraction pattern with rhythmic Ca2+ transients (FIG. 2A, D, E). Mimicking Ca2+ overload by increasing extracellular Ca2+ levels was sufficient to disrupt normal Ca2+ cycling and induce irregular contractions in mESC-CMs (FIG. 2B, D, E). Remarkably, efsevin treatment restored rhythmic Ca2+ transients and cardiac contractions in these cells (FIG. 2C-E). Similar effect was observed in human embryonic stem cell-derived cardiomyocytes (hESC-CMs) (FIG. 2F). Together, these findings suggest that efsevin targets a conserved Ca2+ regulatory mechanism critical for maintaining rhythmic cardiac contraction in fish, mice and humans.

VDAC2 Mediates the Suppressive Effect of Efsevin on Tre

Figure 3A:
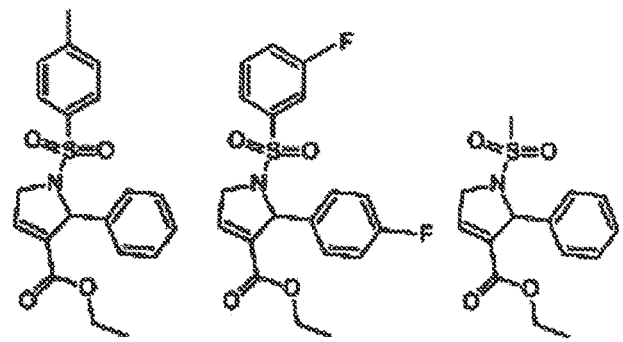
Figure 3B:
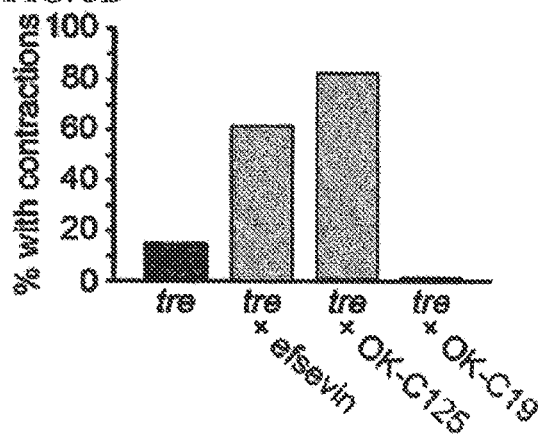
Figure 3C:
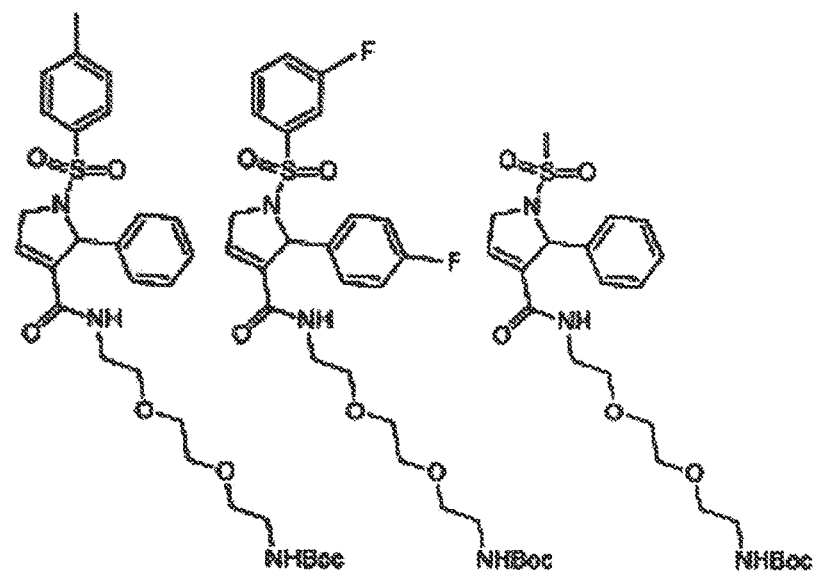

To identify the protein target of efsevin, we generated a N-Boc-protected 2-aminoethoxyethoxyethylamine linker-attached efsevine (efsevine$^L$) (FIGS. 3A and C). This modified compound retained the activity of efsevin to restore cardiac contractions in ncx1h deficient embryos (FIGS. 3B and D) and was used to create efsevin-conjugated agarose beads (efsevin$^{LB}$). A 32 kD protein species was detected from zebrafish lysate due to its binding ability to efsevin$^{LB}$ and OK-C125$^{LB}$, an active efsevin derivative conjugated to beads, but not to beads capped with ethanolamine alone or beads conjugated with an inactive efsevin analog (OK-C19$^{LB}$) (FIG. 3A-D). Furthermore, preincubation of zebrafish lysate with excess efsevin prevented the 32 kD protein from binding to efsevin$^{LB}$ or OK-C125$^{LB}$. Mass spectrometry analysis revealed that this 32 kD band represents a zebrafish homologue of the mitochondrial voltage-dependent anion channel 2 (VDAC2) (FIG. 3E) by identification of VDAC2 peptide LTFDTTFSPNTGK by b- and y-series ions analysis (SEQ ID NO: 8).

Figure 4A:
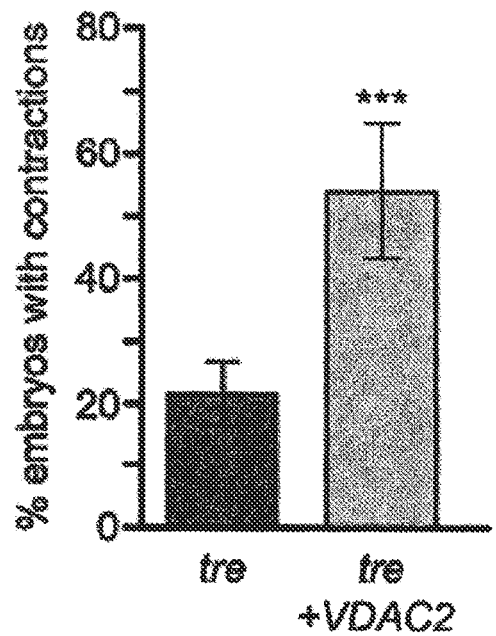
FIGS. 4A-4F show test results demonstrating VDAC2 restores rhythmic cardiac contractions in tre. In situ hybridization analysis showed that VDAC2 is expressed in embryonic hearts at 36 hpf and 48 hpf. (A) Injection of 25 pg in-vitro synthesized VDAC2 mRNA restored cardiac contractions in 52.9±12.1% (n=78) of one-day-old ire embryos, compared to 21.8±5.1% in uninjected siblings (n=111). (B) Schematic diagram of myl7:VDAC2 construct. (C) While only ~20% of myl7:VDAC2; NCX1hMO embryos have coordinated contractions (n=116), 52.3±2.4% of these embryos established persistent, rhythmic contractions after TBF induction of VDAC2 (n=154). (D) On average, 71.2±8.8% efsevin treated embryos have coordinated cardiac contractions (n=131). Morpholino antisense oligonucleotide knockdown of VDAC2 ($MO^{VDAC2}$) attenuates the ability of efsevin to suppress cardiac fibrillation in tre embryos (45.3±7.4% embryos with coordinated contractions, n=94). (E) Efsevin treatment restores coordinated cardiac contractions in 76.2±8.7% NCX1MO embryos, only 54.1±3.6% VDAC2$^{zfn/zfn}$; NCX1MO embryos have coordinated contractions (n=250). (F) Diagram of Zinc finger target sites. VDAC2$^{zfn/zfn}$ carries a 34 bp deletion in exon 3 which results in a premature stop codon (asterisk).
Figure 4B:
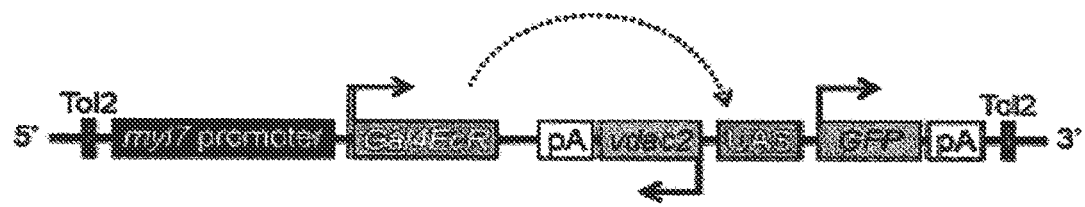
Figure 4C:
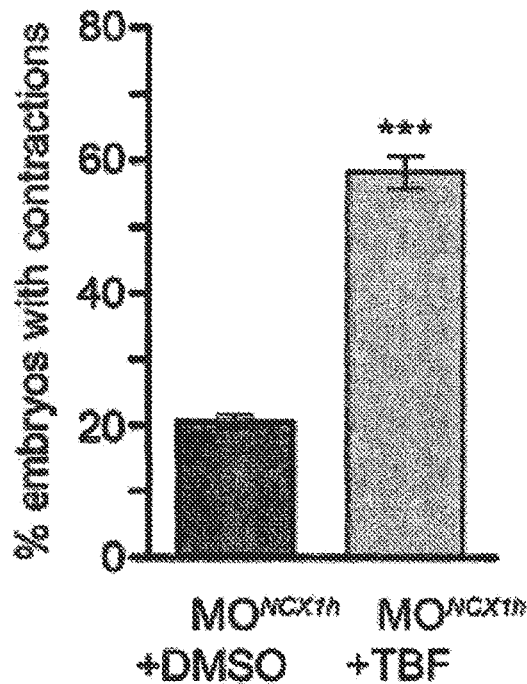
Figure 4D:
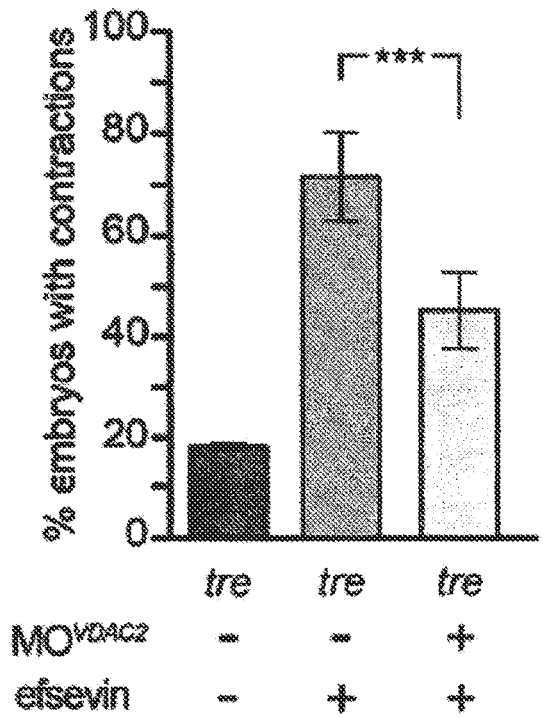
Figure 4E:
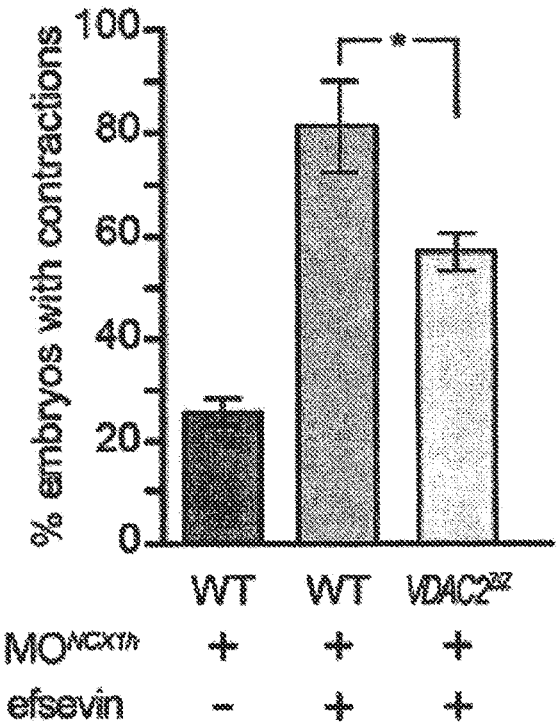
Figure 4F:
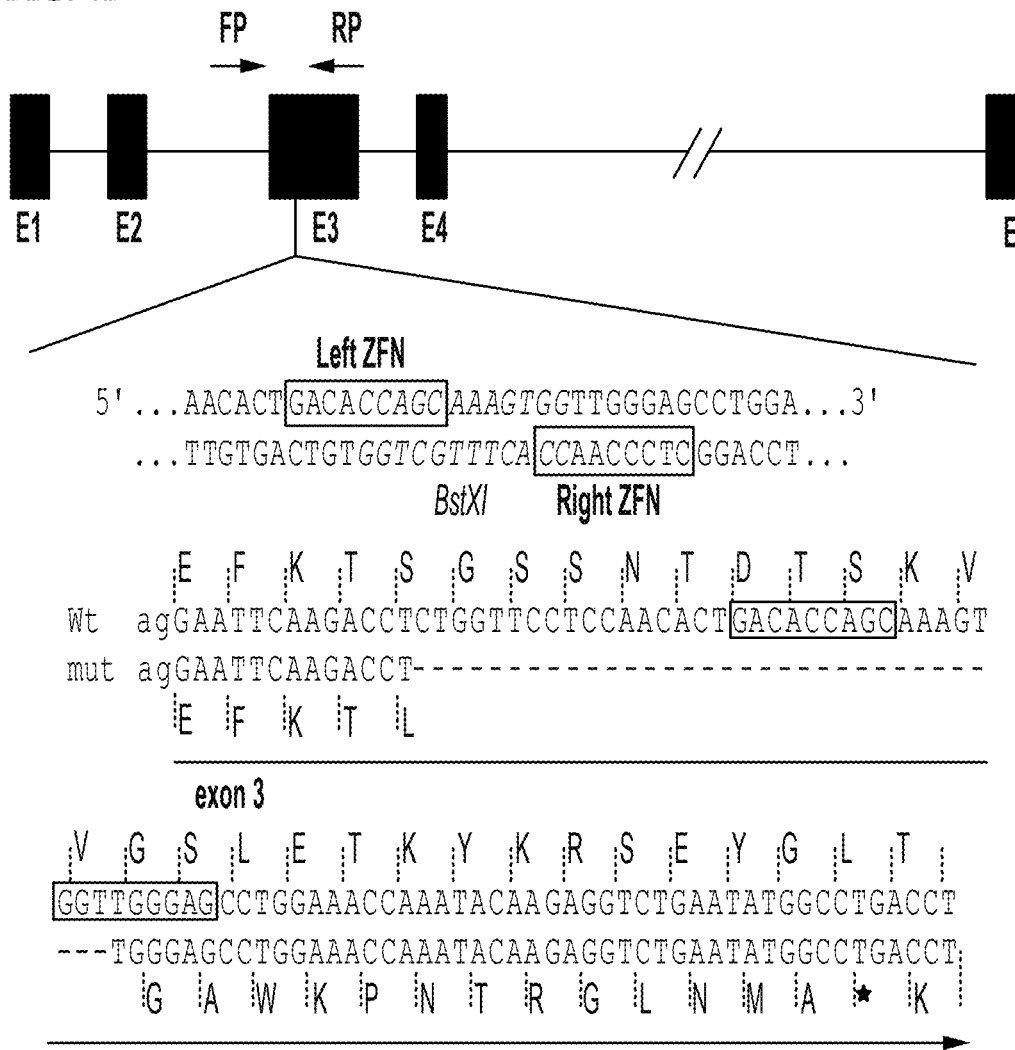

VDAC2 is expressed in the developing zebrafish heart, as confirmed by in situ hybridization analysis of embryonic hearts at 36 hpf and 48 hpf, making it a good candidate for mediating efsevin's effect on cardiac Ca$^{2+}$ handling. To examine this possibility, we injected in vitro synthesized VDAC2 RNA into tre embryos and found that the majority of these embryos had coordinated cardiac contractions similar to those subjected to efsevin treatment (FIG. 4A). In addition, we generated myl7:VDAC2 transgenic fish in which VDAC2 expression can be induced in the heart by tebufenozide (TBF) (FIG. 4B). In situ hybridization analysis showed that TBF treatment induces VDAC2 expression in the heart. Knocking down NCX1h in myl7:VDAC2 embryos results in chaotic cardiac movement similar to tre. Like efsevin treatment, induction of VDAC2 expression by TBF treatment restored coordinated and rhythmic contractions in myl7:VDAC2; NCX1h MO hearts (FIG. 4C). Conversely, knocking down VDAC2 in tre hearts attenuated the suppressive effect of efsevin (FIG. 4D). Furthermore, we generated VDAC2 null embryos by the Zinc Finger Nuclease gene targeting approach (FIG. 4F). In situ hybridization analysis showed loss of VDAC2 transcripts in VDAC2$^{zfn/zfn}$ embryos (SEQ ID NO: 2-7). Similar to that observed in morpholino knockdown embryos, homozygous VDAC2$^{LA2256}$ embryos do not exhibit noticeable morphological defects, but the suppressive effect of efsevin was attenuated in homozygous VDAC2$^{LA2256}$; NCX1MO embryos (FIG. 4E). These findings demonstrate that VDAC2 is a major mediator for efsevin's effect on ncx1h deficient hearts.

VDAC2-Dependent Effect of Efsevin on Mitochondrial Ca$^{2+}$ Uptake

Figure 5A:
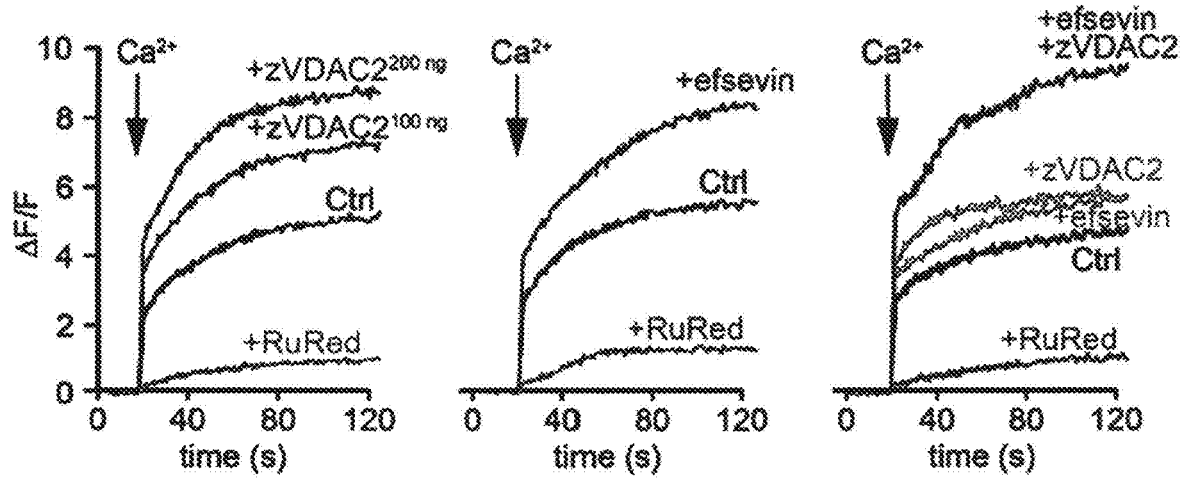
FIGS. 5A-5D show test results demonstrating efsevin enhances mitochondrial $Ca^{2+}$ uptake. HeLa cells were transfected with a flag-tagged zebrafish VDAC2 (VDAC2$^{flag}$), immunostained against the flag epitope and counterstained for mitochondria with MitoTracker Orange and for nuclei with DAPI. (A) Representative traces of mitochondrial matrix $[Ca^{2+}]$ ($[Ca^{2+}]_m$) detected by Rhod2. Arrows denote the addition of $Ca^{2+}$. Mitochondrial $Ca^{2+}$ uptake was assessed when VDAC2 was overexpressed (left), cells were treated with 1 μM efsevin (middle) and combination of both at suboptimal doses (right). Control-traces with ruthenium red (RuRed) show mitochondrial specificity of the signal. (B) Representative traces of cytosolic $[Ca^{2+}]$ ($[Ca^{2+}]_c$) changes upon the application of 7.5 μM $IP_3$ in the presence (+) or absence (−) of RuRed. Mitochondrial $Ca^{2+}$ uptake was assessed by the difference of the − and + RuRed conditions normalized to the total release (n=4; mean±SE). (C) MEFs overexpressing zebrafish VDAC2 (polycistronic with mCherry) were stimulated with 1 μM ATP in a nominally $Ca^{2+}$ free buffer. Changes in $[Ca^{2+}]_c$ and $[Ca^{2+}]_m$ were imaged using fura2 and mitochondria-targeted inverse pericam, respectively. Black and gray traces show the $[Ca^{2+}]_c$ (in nM) and $[Ca^{2+}]_m$ ($F_0$/F mtpericam) time courses in the absence (left) or present (right) of efsevin. (D) Bar charts: Cell population averages for the peak $[Ca^{2+}]_c$ (left), the corresponding $[Ca^{2+}]_m$ (middle), and the coupling time (time interval between the maximal $[Ca^{2+}]_c$ and $[Ca^{2+}]_m$ responses) in the presence (black, n=24) or absence (gray, n=28) of efsevin.

VDAC is an abundant channel located on the outer mitochondrial membrane serving as a primary passageway for metabolites and ions (Rapizzi et al., 2002; Bathori et al., 2006; Shoshan-Barmatz et al., 2010). At its close state, VDAC favours Ca$^{2+}$ flux (Tan et al., 2007, Biochim Biophys Acta 1768, 2510-2515). To examine whether efsevin would modulate mitochondrial Ca$^{2+}$ uptake via VDAC2, we transfected HeLa cells with VDAC2. HeLa cells transfected with a flag-tagged zebrafish VDAC2 (VDAC2$^{flag}$) were immunostained against the flag epitope and counterstained for mitochondria with MitoTracker Orange and for nuclei with DAPI to confirm transfection. We noted increased mitochondrial Ca$^{2+}$ uptake in permeabilized VDAC2 transfected and efsevin-treated cells after the addition of Ca$^{2+}$ and the combined treatment further enhanced mitochondrial Ca$^{2+}$ levels (FIG. 5A).

Figure 5B:
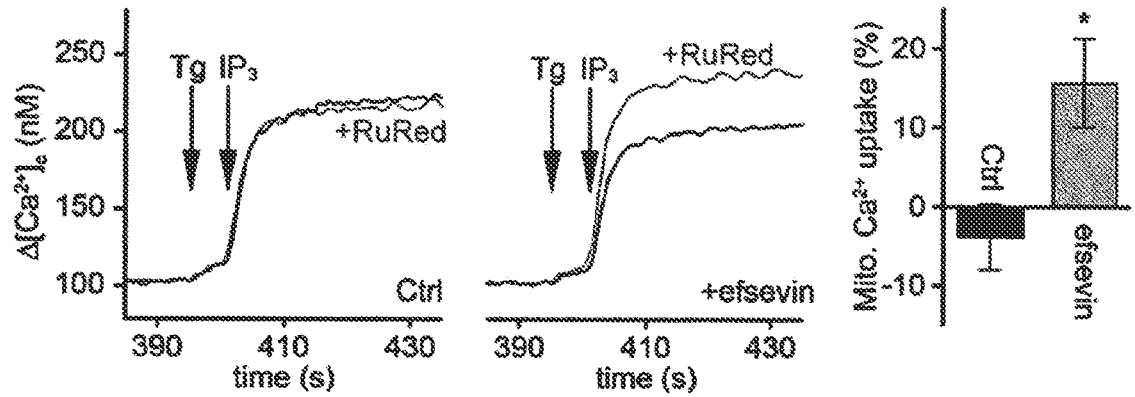
Figure 5C:
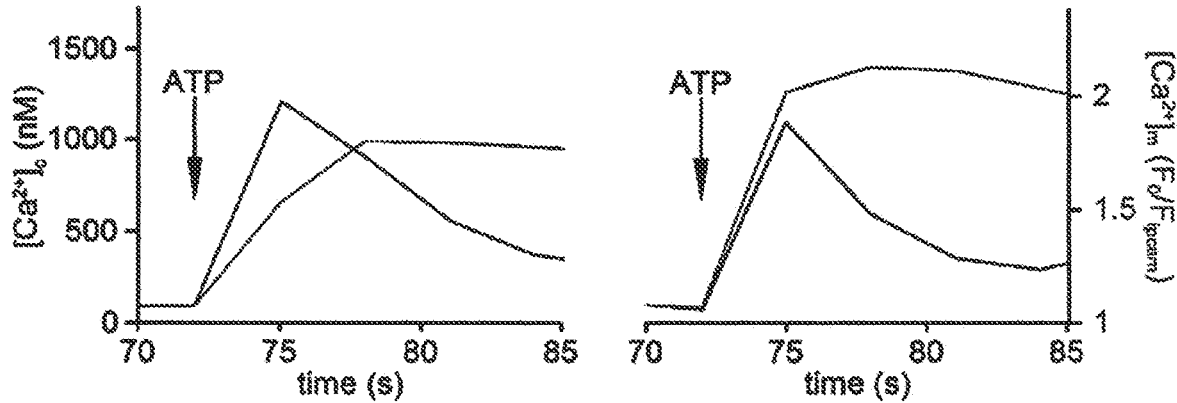
Figure 5D:
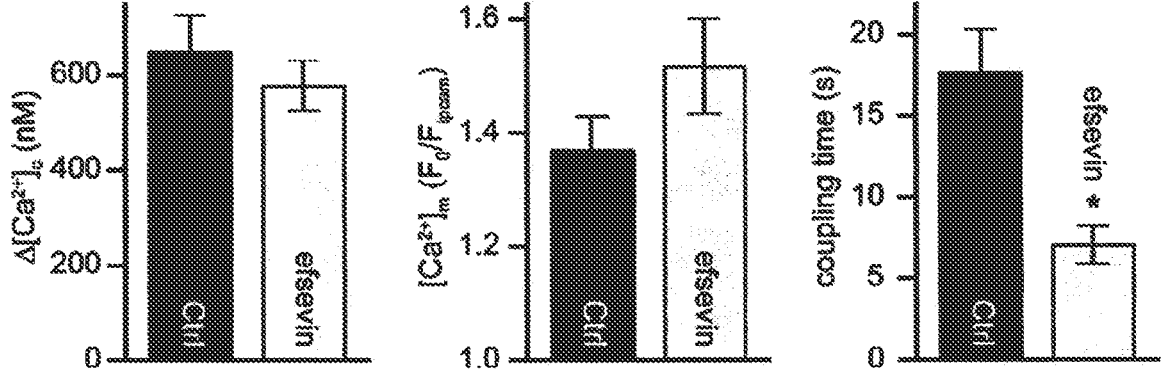
Figure 8:
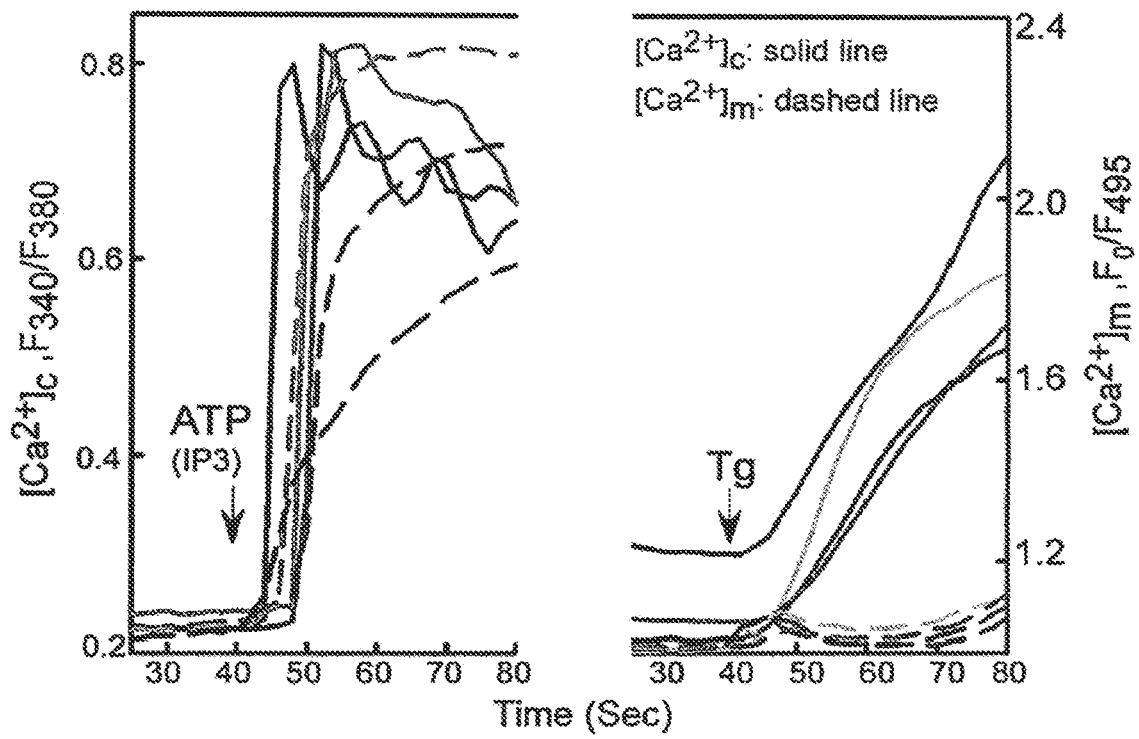
FIG. 8 shows that local Ca²⁺ delivery between IP3 receptors and VDAC2. V1/V3DKO MEFs were stimulated with 100 µM ATP (left) or 2 µM thapsigargan (Tg) (right). Changes in [Ca²⁺]$_c$ and [Ca²⁺]$_m$ were imaged using fura 2 and mitochondria targeted inverse pericam, respectively. Representative traces obtained in 3 cells are shown.
Figure 9A:
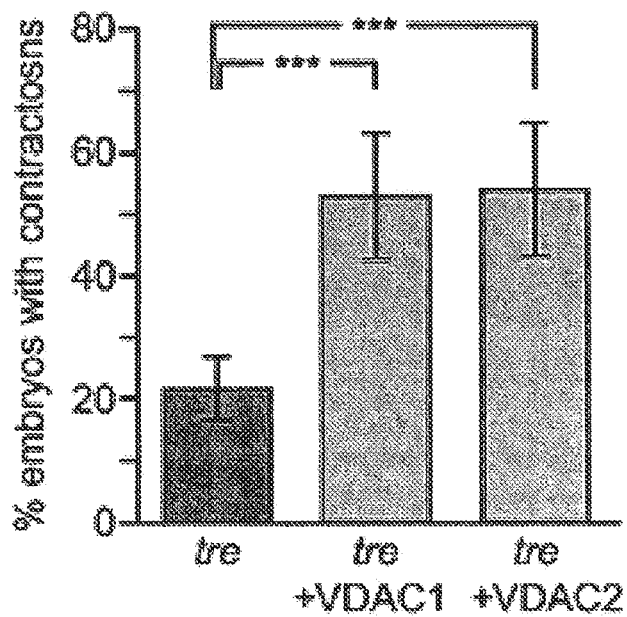
FIGS. 9A-9G show that mitochondria regulate cardiac rhythmicity through a VDAC dependent mechanism.
Figure 9B:
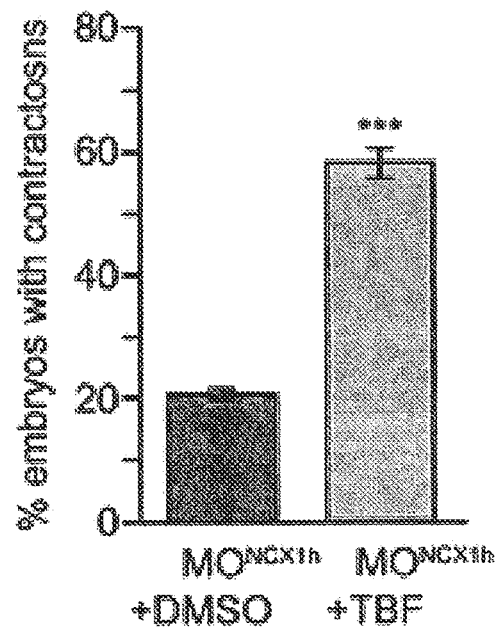
Figure 9C:
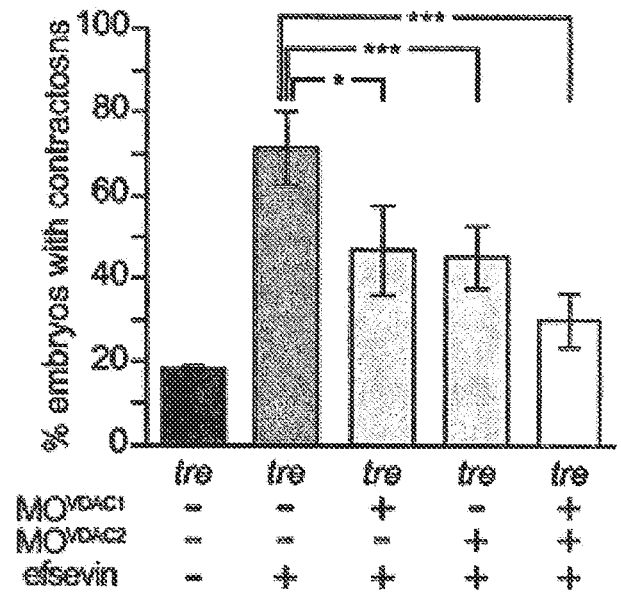
Figure 9D:
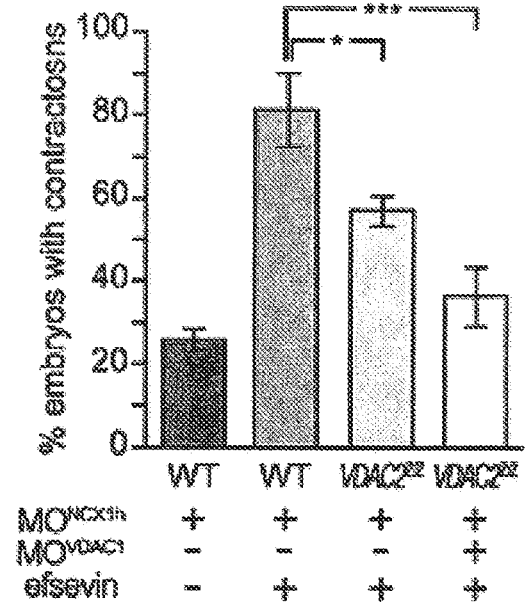
Figure 9E:
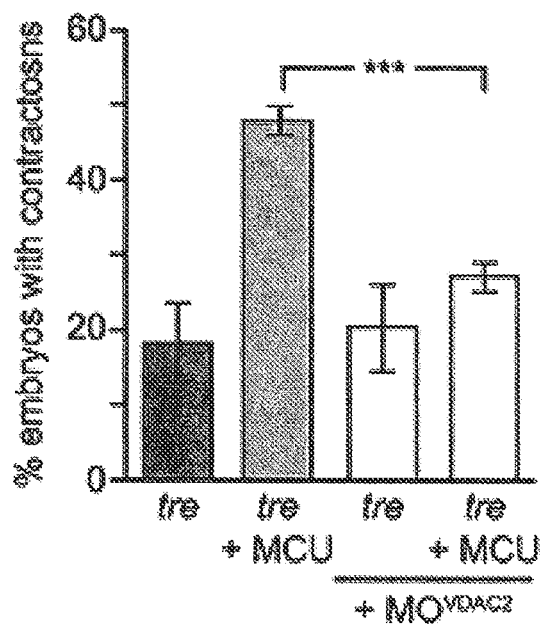
Figure 9F:
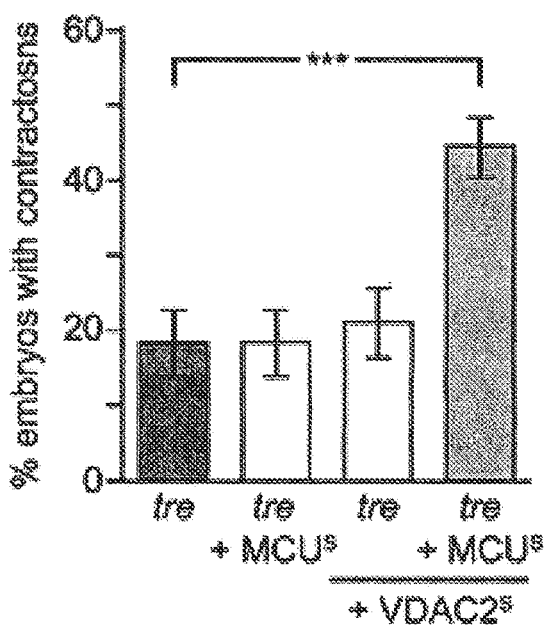
Figure 9G:
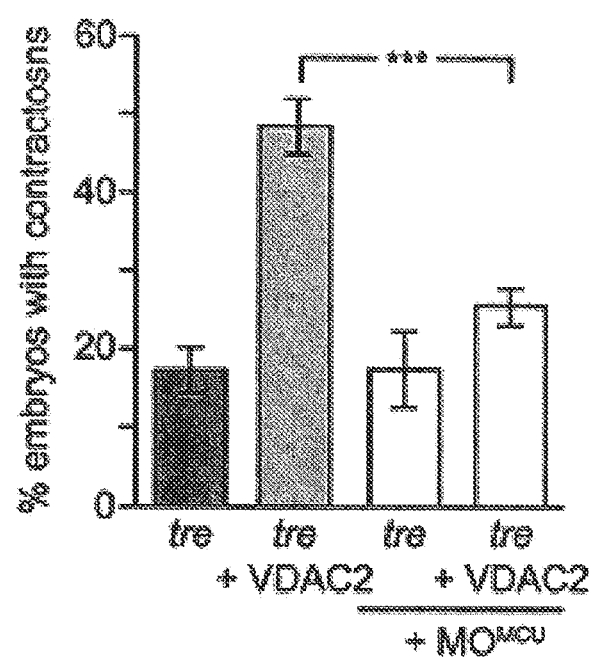

Mitochondria are located in close proximity to Ca$^{2+}$ release sites of the ER/SR and an extensive crosstalk between the two organelles exists (Garcia-Perez et al., 2008; Hayashi et al., 2009; Brown et al., 2010, Cardiovasc Res 88, 241-249; Dorn et al., 2010; Kohlhaas et al., 2013). We examined whether Ca$^{2+}$ released from intracellular stores could be locally transported into mitochondria through VDAC2 in VDAC1/VDAC3 double knockout (V1/V3DKO) MEFs where VDAC2 is the only VDAC isoform being expressed (Roy et al., 2009a). While treatments with ATP, an IP3-linked agonist, and Thapsigargin, a SERCA inhibitor, stimulated similar global cytoplasmic [Ca$^{2+}$] elevation in intact cells, only ATP induced a rapid mitochondrial matrix [Ca$^{2+}$] rise (FIG. 8). This finding is consistent with observations obtained in other cell types (Rizzuto et al., 1994, J Cell Biol 126, 1183-1194; Hajnoczky et al., 1995, Cell 82, 415-424) and suggests that Ca$^{2+}$ was locally transferred from IP3 receptors to mitochondria through VDAC2 at the close ER-mitochondrial associations. We next investigated whether this process could be modulated by efsevin. In permeabilized V1/V3DKO MEFs, treatment with efsevin increased the amount of Ca$^{2+}$ transferred into mitochondria during IP$_3$-induced Ca$^{2+}$ release (FIG. 5B). Also, in intact V1/V3 DKO MEFs, efsevin accelerated the transfer of Ca$^{2+}$ released from intracellular stores into mitochondria during stimulation with ATP (FIGS. 5C and D).

Figure 6A:
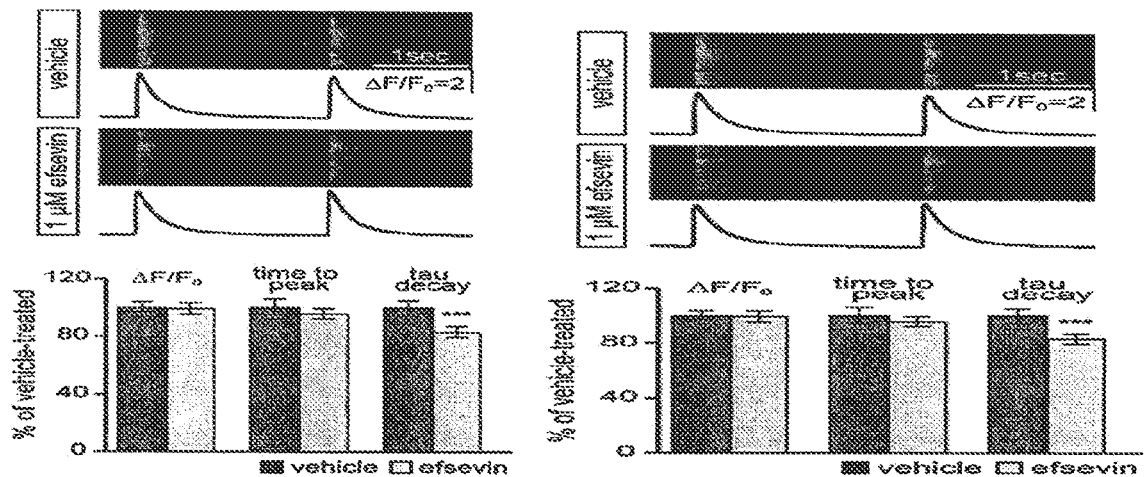
FIGS. 6A-6C show effects of efsevin on isolated cardiomyocytes. (A) Electrically paced $Ca^{2+}$ transients at 0.5 Hz (top). Normalized quantification of $Ca^{2+}$ transient parameters reveals no difference for transient amplitude (efsevin-treated at 98.6±4.5% of vehicle-treated) and time to peak (95±3.9%), but a significant decrease for the rate of decay (82.8±4% of vehicle- for efsevin-treated) (lower panel). (B) Representation of typical $Ca^{2\pm}$ sparks of vehicle- and efsevin treated cardiomyocytes (top). No differences were observed for spark frequency (101.1±7.7% for efsevin-compared to vehicle-treated), maximum spark amplitude (101.6±2.5%) and $Ca^{2\pm}$ release flux (98.7±2.8%). In contrast, the decay phase of the single spark was significantly faster in efsevin treated cells (82.5±2.1% of vehicle-treated). Consequently, total duration of the spark was reduced to 85.7±2% and the total width was reduced to 89.5±1.4% of vehicle-treated cells. *, p<0.05; ***, p<0.001. (C) Quantitative analysis of spontaneous $Ca^{2\pm}$ waves spanning more than half of the entire cell. Addition of 1 μM efsevin reduced $Ca^{2\pm}$ waves to approximately half. Increasing the concentration of efsevin to 10 µM further reduced the number of spontaneous Ca²⁺ waves and 25 µM efsevin almost entirely blocked the formation of Ca²⁺ waves.
Figure 6B:
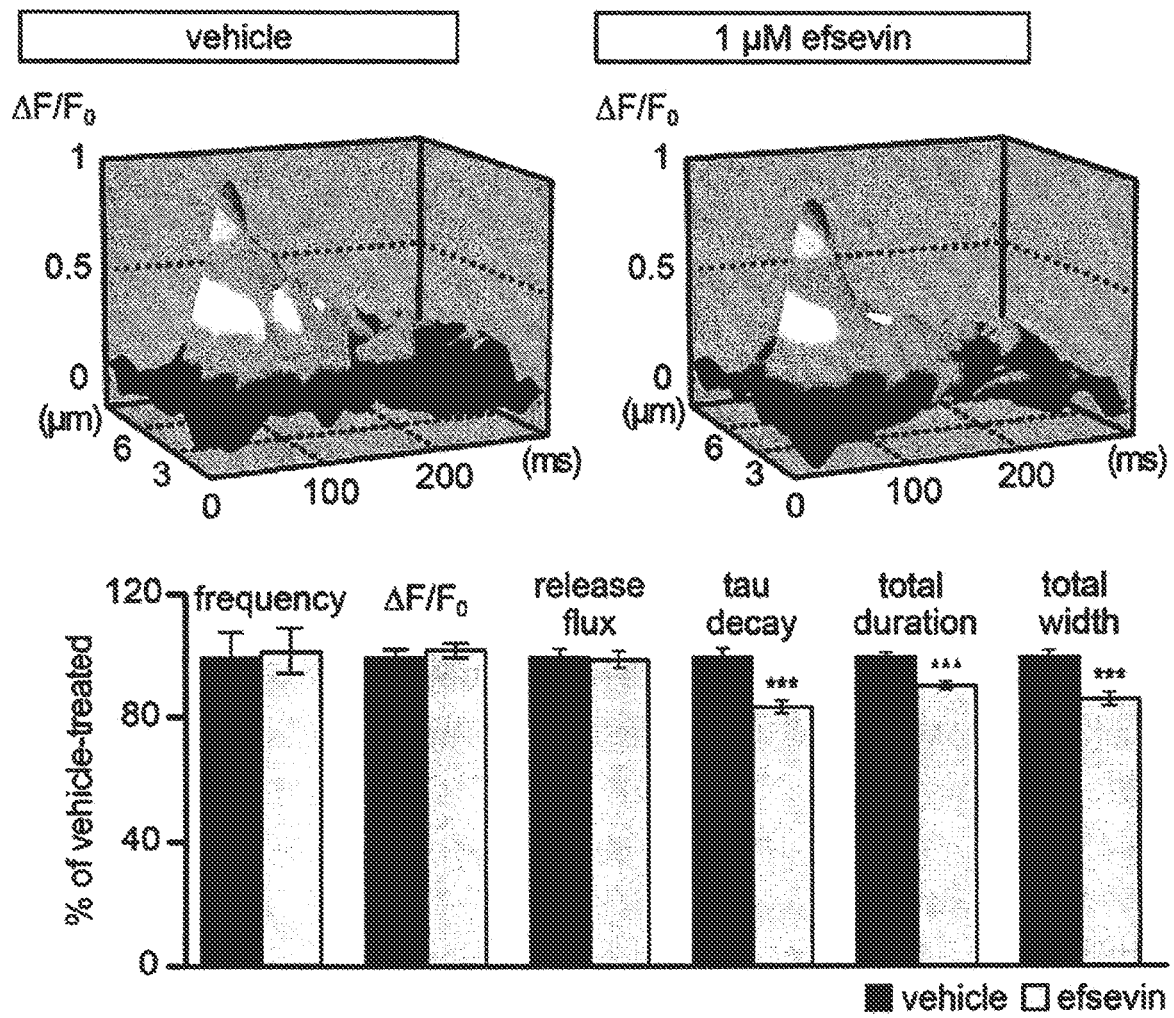
Figure 6C:
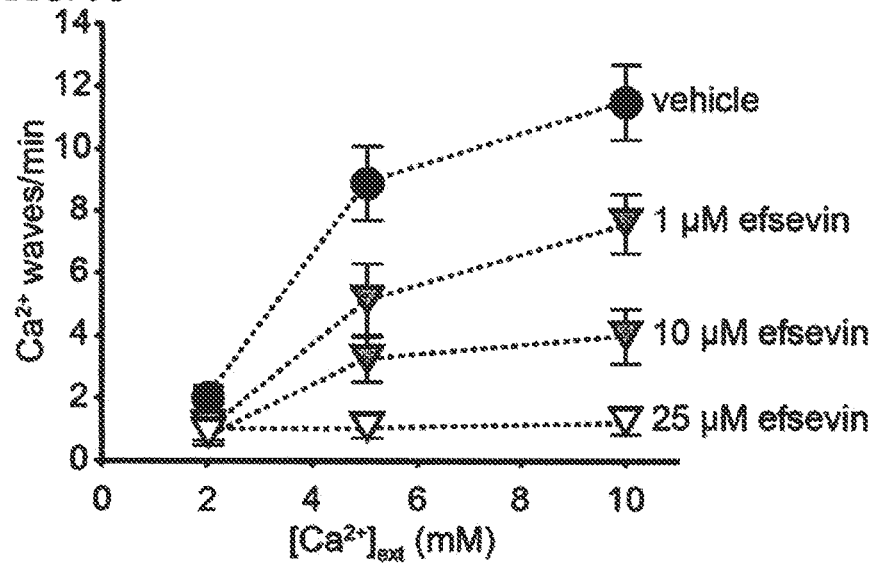

Efsevin Modulates Ca$^{2+}$ Sparks and Suppresses Erratic Ca$^{2+}$ Waves in Cardiomyocytes We next examined the effect of efsevin on cytosolic Ca$^{2+}$ signals in isolated adult murine cardiomyocytes. We found that efsevin treatment induced faster inactivation kinetics without affecting the amplitude or time to peak of paced Ca$^{2+}$ transients (FIG. 6A). Similarly, efsevin treatment did not significantly alter the frequency, amplitude or Ca$^{2+}$ release flux of spontaneous Ca$^{2+}$ sparks, local Ca$^{2+}$ release events, but accelerated the decay phase resulting in sparks with a shorter duration and a narrower width (FIG. 6B). These results indicate that by activating mitochondrial Ca$^{2+}$ uptake, efsevin accelerates Ca$^{2+}$ removal from the cytosol in cardiomyocytes and thereby restricts local cytosolic Ca$^{2+}$ sparks to a narrower domain for a shorter period of time without affecting SR Ca$^{2+}$ load or RyR Ca$^{2+}$ release. Under conditions of Ca$^{2+}$ overload, single Ca$^{2+}$ sparks can trigger opening of neighbouring Ca$^{2+}$ release units and thus induce the formation of erratic Ca$^{2+}$ waves. Efsevin treatment significantly reduced the number of propagating Ca2+ waves in a dosage-dependent manner (FIG. 6C), demonstrating a potent suppressive effect of efsevin on the propagation of Ca2+ overload-induced Ca2+ waves and suggesting that efsevin could serve as a pharmacological tool to manipulate local Ca2+ signals.

Mitochondrial Ca2+ Uptake Modulates Embryonic Cardiac Rhythmicity

Figure 7A:
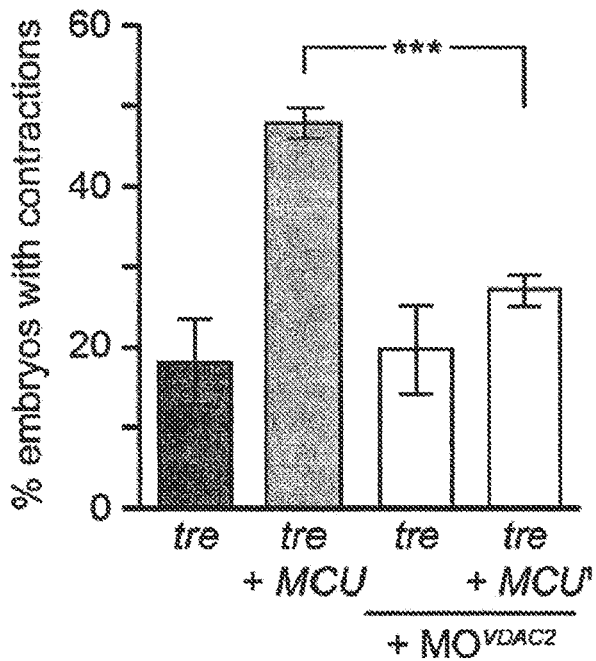
FIGS. 7A-7E show test results demonstrating that mitochondria regulate cardiac rhythmicity through a VDAC2-dependent mechanism. MCU and MICU1 are expressed in the developing zebrafish hearts. (A) Overexpression of MCU is sufficient to restore coordinated cardiac contractions in tre embryos (47.1±1.6% embryos, n=112 as opposed to 18.3±5.3% of uninjected siblings, n=64) while this effect is significantly attenuated when co-injected with morpholino antisense oligonucleotide targeted to VDAC2 (27.1±1.9% embryos, n=135). (B) Suboptimal overexpression of MCU (MCU$^S$) and VDAC2 (VDAC2$^S$) in combination is able to suppress cardiac fibrillation in tre embryos (42.9±2.6% embryos, n=129). (C) The ability of VDAC2 to restore rhythmic contractions in tre embryos (48.5±3.5% embryos, n=111) is significantly attenuated when MCU is knocked down by antisense oligonucleotide (MO$^{MCU}$) (25.6±2.4% embryos, n=115). (D) Overexpression of MICU1 is sufficient to restore rhythmic cardiac contractions in tre embryos (49.3±3.4% embryos, n=127 compared to 16.8±1.4% of uninjected siblings, n=150). This effect is abrogated by VDAC2 knockdown (MO$^{VDAC2}$, 25.3±5.5% embryos, n=97). (E) Suboptimal overexpression of MICU1 (MICU1$^S$) and VDAC2 (VDAC2$^S$) in combination is able to restore rhythmic cardiac contractions in tre embryos (48.6±6.0%, n=106). Error bars represent s.d.; *p<0.05; ***p<0.001.
Figure 7B:
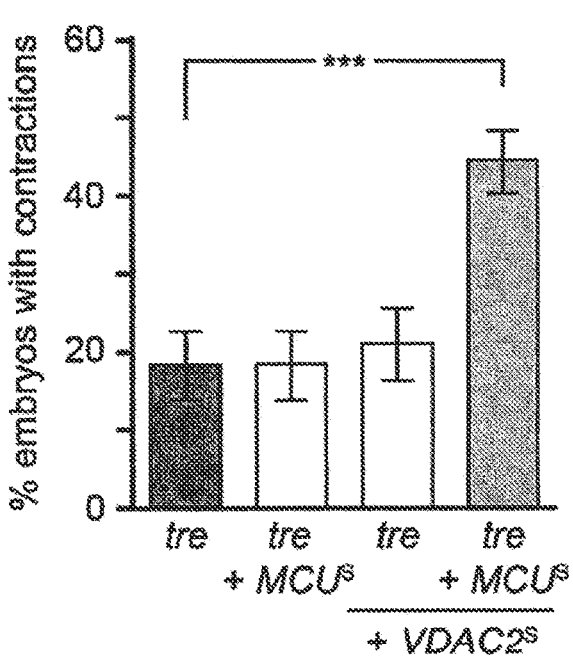
Figure 7C:
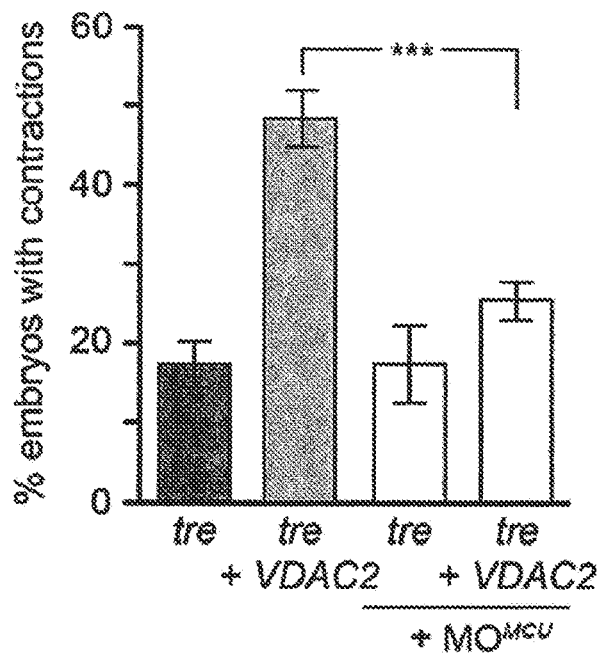
Figure 7D:
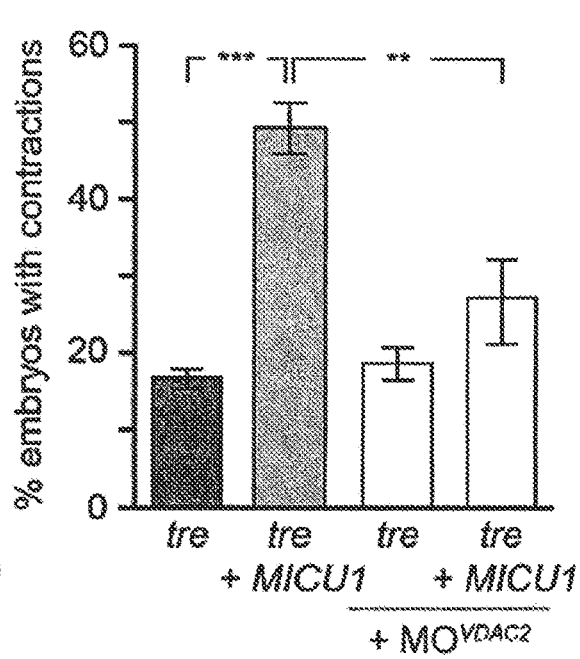
Figure 7E:
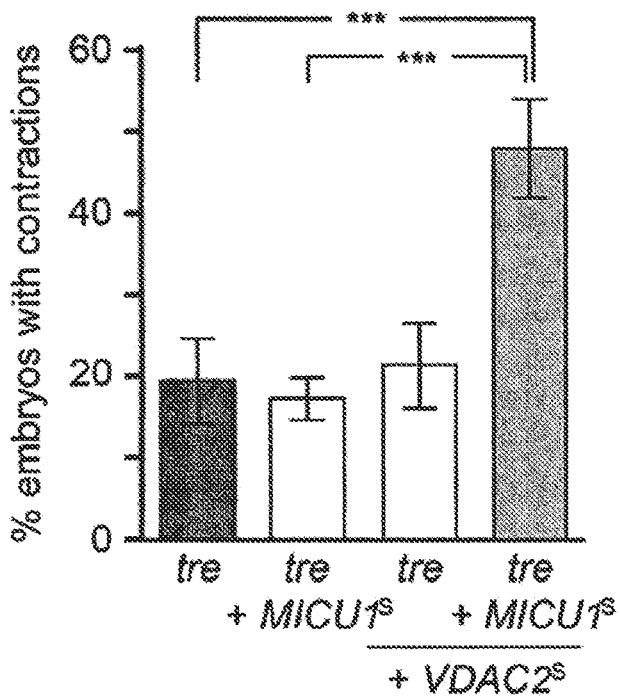

We believe that efsevin treatment/VDAC2 overexpression suppresses aberrant Ca2+ handling-associated arrhythmic cardiac contractions by buffering excess Ca$^{2+}$ into mitochondria. Therefore we predict that activating other mitochondrial Ca$^{2+}$ uptake molecules would likewise restore coordinated contractions in tre. To test this model, we cloned zebrafish MCU and MICU1, an inner mitochondrial membrane $Ca^{2+}$ transporter and its regulator (Perocchi et al., 2010, Nature 467, 291-296; Baughman et al., 2011; De Stefani et al., 2011; Mallilankaraman et al., 2012, Cell 151, 630-644; Csordas et al., 2013, Cell Metab 17, 976-987). In situ hybridization showed that MCU and MICU1 were expressed in the developing zebrafish heart and their expression levels were comparable between the wild type and tre hearts and embryos with and without efsevin treatment. Overexpression of MCU restored coordinated contractions in tre, akin to what was observed with VDAC2 (FIG. 7A). In addition, tre embryos injected with suboptimal concentrations of MCU or VDAC2 had a fibrillating heart, but embryos receiving both VDAC2 and MCU at the suboptimal concentration manifested coordinated contractions (FIG. 7B), demonstrating a synergistic effect of these proteins. Furthermore, overexpression of MCU failed to suppress the tre phenotype in the absence of VDAC2 activity and VDAC2 could not restore coordinated contractions in tre without functional MCU (FIG. 7A,C). Similar results were observed by manipulating MICU1 activity (FIGS. 7D and E). Together, these findings indicate that mitochondrial $Ca^{2+}$ uptake mechanisms on outer and inner mitochondrial membranes act cooperatively to regulate cardiac rhythmicity.

Mitochondria Regulate Cardiac Rhythmicity Through a VDAC Dependent Mechanism

Affinity agarose beads covalently linked with efsevin (efsevin$^{LB}$) pulled down 2 protein species from zebrafish embryonic lysate, whereof one, the 32 kD upper band, was sensitive to competition with a 100 fold excess free efsevin$^L$. The 32 kD band was not detected in proteins eluted from beads capped with ethanolamine alone (beads$^C$) or beads linked to an inactive derivative of efsevin, OK-C19$^{LB}$, but was detected in samples eluted from beads attached with a biologically active derivative, OK-C125$^{LB}$. Also for the OK-C125$^{LB}$ pull-down the 32 kD band was again sensitive to competition with free efsevin. In situ hybridization analysis showed that VDAC1, VDAC2 and MCU are expressed in embryonic hearts at 36 hpf and 48 hpf.

FIG. 9 A)-G) show that mitochondria regulate cardiac rhythmicity through a VDAC dependent mechanism.

A) Injection of 25 pg in-vitro synthesized VDAC1 and VDAC2 mRNA restored cardiac contractions in 53.0±10.2% (n=126) and 52.9±12.1% (n=78) of one-day-old tre embryos, respectively, compared to 21.8±5.1% in uninjected siblings (n=111).

B) While only ~20% of myl7:VDAC2; NCX1hMO embryos have coordinated contractions (n=116), 52.3±2.4% of these embryos established persistent, rhythmic contractions after TBF induction of VDAC2 (n=154).

C) On average, 71.2±8.8% efsevin treated embryos have coordinated cardiac contractions (n=131). Morpholino antisense oligonucleotide knockdown of VDAC2 (MO$^{VDAC2}$) or VDAC1 (MO$^{VDAC1}$) attenuates the ability of efsevin to suppress cardiac fibrillation in tre embryos (45.3±7.4% and 46.9±10.7% embryos with coordinated contractions, n=94 and 114, respectively). Knocking down VDAC1/2 simultaneously further suppresses efsevin's effect (30.3±6.3%, n=75).

D) Efsevin treatment restores coordinated cardiac contractions in 76.2±8.7% NCX1MO embryos, only 54.1±3.6% VDAC2$^{zfn/zfn}$; NCX1MO embryos and 35.7±7.1% VDAC2$^{zfn/zfn}$; VDAC1MO; NCX1MO embryos have coordinated contractions (n=250).

E) Overexpression of MCU is sufficient to restore coordinated cardiac contractions in tre embryos (47.1±1.6% embryos, n=112 as opposed to 18.3±5.3% of uninjected siblings, n=64) while this effect is significantly attenuated when co-injected with morpholino antisense oligonucleotide targeted to VDAC2 (27.1±1.9% embryos, n=135).

F) Suboptimal overexpression of MCU (MCU$^S$) and VDAC2 (VDAC2$^S$) in combination is able to suppress cardiac fibrillation in tre embryos (42.9±2.6% embryos, n=129).

G) The ability of VDAC2 to restore rhythmic contractions in tre embryos (48.5±3.5% embryos, n=111) is significantly attenuated when MCU is knocked down by antisense oligonucleotide (MO$^{MCU}$) (25.6±2.4% embryos, n=115). Error bars represent s.d.; *p<0.05; ***p<0.001.

E. Conclusion

In summary, we conducted a chemical suppressor screen in zebrafish to dissect the regulatory network critical for maintaining rhythmic cardiac contractions and to identify mechanisms underlying aberrant $Ca^{2+}$ handling-induced cardiac dysfunction. We show that activation of VDAC2 through overexpression or efsevin treatment potently restores rhythmic contractions in NCX1h deficient zebrafish hearts and effectively suppresses $Ca^{2+}$ overload-induced arrhythmogenic $Ca^{2+}$ events and irregular contractions in mouse and human cardiomyocytes. We provide evidence that potentiating VDAC2 activity enhances mitochondrial $Ca^{2+}$ uptake, accelerates $Ca^{2+}$ transfer from intracellular stores into mitochondria and spatially and temporally restricts single $Ca^{2+}$ sparks in cardiomyocytes. The crucial role of mitochondria in the regulation of cardiac rhythmicity is further supported by the findings that VDAC2 functions in concert with MCU; these genes have a strong synergistic effect on suppressing cardiac fibrillation and loss of function of either gene abrogates the rescue effect of the other in tre.

The regulatory roles of mitochondrial $Ca^{2+}$ in cardiac metabolism, cell survival and fate have been studied extensively (Brown et al., 2010; Dorn et al., 2010; Doenst et al., 2013, Circ Res 113, 709-724; Kasahara et al., 2013, Science 342, 734-737; Kohlhaas et al., 2013; Luo et al., 2013, Circ Res 113, 690-708). Our study provides genetic and physiologic evidence supporting an additional role for mitochondria in regulating cardiac rhythmicity and reveals VDAC2 as a modulator of $Ca^{2+}$ handling in cardiomyocytes. Our findings, together with recent reports of the physical interaction between VDAC2 and RyR2 (Min et al., 2012, Biochem J 447, 371-379) and the close proximity of outer and inner mitochondrial membranes at the contact sites between the mitochondria and the SR (Garcia-Perez et al., 2011, Am J Physiol Heart Circ Physiol 301, H1907-1915), suggest an intriguing model. We propose that mitochondria facilitate an efficient clearance mechanism in the $Ca^{2+}$ microdomain, which modulates $Ca^{2+}$ handling without affecting global $Ca^{2+}$ signals in cardiomyocytes. In this model, VDAC facilitates mitochondrial $Ca^{2+}$ uptake via MCU complex and thereby controls the duration and the diffusion of cytosolic $Ca^{2+}$ near the $Ca^{2+}$ release sites to ensure rhythmic cardiac contractions. This model is consistent with our observation that efsevin treatment induces faster inactivation kinetics of cytosolic $Ca^{2+}$ transients without affecting the amplitude or the time to peak in cardiomyocytes and the reports that blocking mitochondrial $Ca^{2+}$ uptake has little impact on cytosolic $Ca^{2+}$ transients (Maack et al., 2006; Kohlhaas et al., 2010, Circulation 121, 1606-1613). Further support for this model comes from the observation of the $Ca^{2+}$ peaks on the OMM (Drago et al., 2012, Proc Natl Acad Sci USA 109, 12986-12991) and the finding that downregulating VDAC2 extends $Ca^{2+}$ sparks (Subedi et al., 2011, Cell Calcium 49, 136-143; Min et al., 2012) and that blocking mitochondrial $Ca^{2+}$ uptake by Ru360 leads to an increased number of spontaneous propagating Ca²⁺ waves (Seguchi et al., 2005, Cell Calcium 38, 1-9). Future studies on the kinetics of VDAC2-dependent mitochondrial Ca²⁺ uptake and exploring potential regulatory molecules for VDAC2 activity will provide insights into how the crosstalk between SR and mitochondria contributes to Ca²⁺ handling and cardiac rhythmicity.

Aberrant Ca²⁺ handling is associated with many cardiac dysfunctions including arrhythmia. Establishing animal models to study molecular mechanisms and develop new therapeutic strategies are therefore major preclinical needs. Our chemical suppressor screen identified a potent effect of efsevin and its biological target VDAC2 on manipulating cardiac Ca²⁺ handling and restoring regular cardiac contractions in fish and mouse and human cardiomyocytes. This success indicates that fundamental mechanisms regulating cardiac function are conserved among vertebrates despite the existence of species-specific features and suggests a new paradigm of using zebrafish cardiac disease models for the dissection of critical genetic pathways and the discovery of new therapeutic approaches. Future studies examining the effects of efsevin on other arrhythmia models would further elucidate the potential for efsevin as a pharmacological tool to treat cardiac arrhythmia associated with aberrant Ca²⁺ handling.

Examples 2-4

Synthesis of Efsevin: Synthesis of (R)-Efsevin and (S)-Efsevin & Identification of (R)-Efsevin as the Active Antipode for the Previously Reported Defibrillator Activity of Efsevin Example 2

(Resolution of (R)- and (S)-Efsevin Through HPLC Separation on Chiral Stationary Phase)

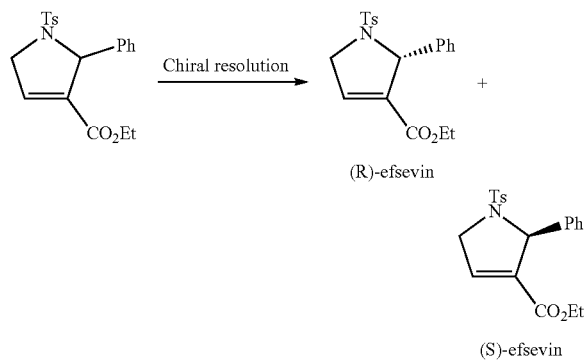

Racemic-efsevin (50 mg, 0.13 mmol) was dissolved in DCM (0.2 mL) and injected into a Shimadzu CBM Lite system using a REGIS (R, R)-DACH DNB 5/100 preparatory column (25 cm×30 mm) with DCM/hexanes (70:30) as eluent at a flow rate of 10.0 mL/min. (R)-efsevin eluted at 75.78 min and (S)-efsevin at 102.72 min (FIGS. 10-13). Fractions were collected and concentrated in vacuo. The protocol was repeated six more times to give (R)-efsevin (158 mg) which was recrystallized with hexanes/EtOAc to give (R)-efsevin crystals (112 mg, >99% ee). Enantiomeric excess were determined by a REGIS (R, R)-DACH DNB 5/100 analytical column (25 cm×4.6 mm) with DCM/hexanes (60:40) as eluent at a flow rate of 2.0 mL/min.

Example 3

(Resolution of (R)-Efsevin and (S)-Efsevin Through Derivatization Using Menthol)

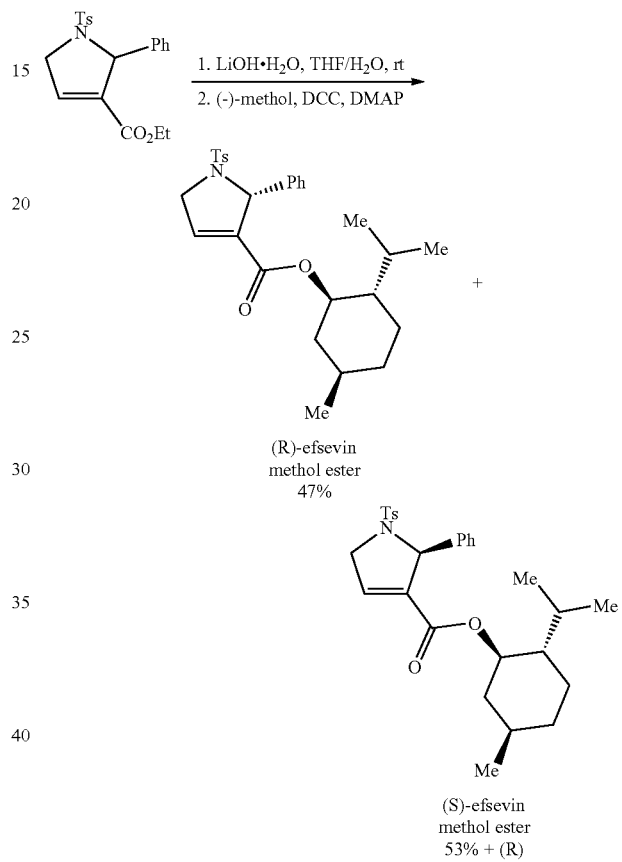

Racemic-efsevin (500 mg, 1.35 mmol) was dissolved in 1:1 H₂O/THF (34.0 mL) at room temperature. Lithium hydroxide monohydrate (141.2 mg, 3.37 mmol) was added to the reaction mixture. The reaction was allowed to stir overnight at room temperature. The reaction was monitored by TLC. Upon completion, mixture was cooled to 0° C. using an ice bath and acidified to pH 1 with aq. 1N HCl. The mixture was extracted with DCM (30 mL×3). The combined organic layer was dried with Na₂SO₄ and concentrated in vacuo. The resulting efsevin carboxylic acid was used in the next step without further purification.

Racemic-efsevin carboxylic acid (1.35 mmol) and (−)-menthol (317.0 mg, 2.0 mmol) were dissolved in DCM (1.0 mL) and cooled to 0° C. using an ice bath. DCC (279.0 mg, 1.35 mmol) and DMAP (1.6 mg, 0.014 mmol) were dissolved in DCM (1.0 mL) and added to the reaction mixture over 1 h using a syringe pump. After addition, the reaction mixture was allowed to warm to room temperature by removing the cooling bath. Upon completion, the mixture was filtered through a short pad of celite and concentrated in vacuo. The crude product was purified using FCC on silica gel (20% EtOAc in hexanes) to yield two diastereoisomeric efsevin menthol esters (385.0 mg, 58%). Selective crystallization in 9:1 hexanes/EtOAc yielded (R)-efsevin menthol ester (180 mg) and (S)-efsevin menthol ester [200 mg with trace (R)-ester]. Both (R)- and (S)-efsevin menthol esters can be hydrolyzed and esterified to give enantiomerically pure (R)- and (S)-efsevin. See (a) Jonas, R.; Wurziger, H. *Tetrahedron* 1987, 43, 4539-4547. (b) Ito, Y.; Miyake, T.; Hatano, S.; Shima, R.; Ohara, T.; Suginome, M. *J. Org. Chem.* 1998, 120, 11880-11893. (d) Yang, D.; Ye, X.-Y.; Xu, M. *J. Org. Chem.* 2000, 65, 2208-2217. (e) Holý, R.; Kováč, M.; Tichý, M.; Závada, J.; Buděšinský, M.; Císařová, I. *Tetrahedron: Asymmetry* 2005, 16, 2031-2038.

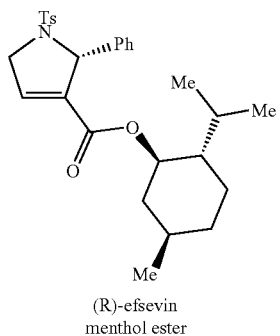 [SMILES: Cc1ccc(S(=O)(=O)N2CC=C(C(=O)O[C@@H]3C[C@H](C)CC[C@H]3C(C)C)[C@H]2c2ccccc2)cc1]

(R)-efsevin menthol ester (R)-Efsevin Menthol Ester $^1$H NMR (500 MHz, CDCl3) (FIG. 14 top) δ 7.34 (d, J=8.3 Hz, 2H), 7.22-7.16 (m, 5H), 7.09 (d, J=8.0 Hz, 2H), 6.86 (q, J=2.0 Hz, 1H), 5.74 (dt, J=5.9, 1.9 Hz, 1H), 4.55 (td, J=10.5, 3.9 Hz, 1H), 4.51 (dt, J=16.9, 2.4 Hz, 2H), 2.35 (s, 3H), 1.87-1.82 (m, 1H), 1.63-1.59 (m, 1H), 1.54-1.51 (m, 2H), 1.41-1.35 (m, 1H), 1.05 (tt, J=5.4, 3.1 Hz, 1H), 0.93-0.84 (m, 5H), 0.82-0.71 (m, 2H), 0.54 (d, J=7.0 Hz, 3H), 0.40 (d, J=7.0 Hz, 3H)

$^{13}$C NMR (125 MHz, CDCl3) (FIG. 14 bottom) δ 161.6, 143.1, 139.2, 136.2, 136.1, 135.9, 129.4, 128.2, 128.01, 127.96, 127.0, 74.8, 68.8, 54.6, 46.8, 40.8, 34.1, 31.4, 25.0, 22.7, 22.0, 21.5, 21.0, 15.4.

Example 4

(Catalytic Asymmetric Synthesis of (S)-Efsevin)

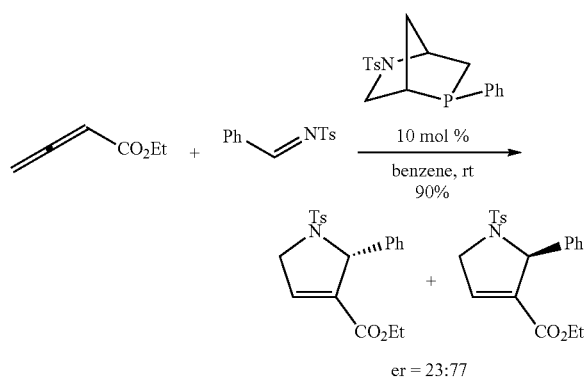

N-Tosyl benzaldimine (5.67 g, 21.9 mmol) was dissolved in benzene (175.0 mL) at room temperature. Exo-phenyl Kwonphos (756.0 mg, 2.19 mmol) was added to the reaction mixture. Ethyl allenoate (2.94 g, 26.3 mmol) was then added into the reaction mixture dropwise. The reaction was allowed to stir at room temperature and monitored by TLC. Upon completion, the mixture was concentrated in vacuo. The resulting mixture was purified using FCC on silica gel (20% EtOAc in hexanes) to yield a 23:77 mixture of (R)- and (S)-efsevin (6.78 g, 90%). Selective crystallization in 4:1 hexanes/EtOAc gave racemic-efsevin (3.12 g), leaving (S)-efsevin (3.66 g) in the mother liquor. The mother liquor was recrystallized in 4:1 hexanes/EtOAc to give (S)-efsevin (2.1 g, >99% ee)

A. Synthesis of (S)-Efsevin Menthol Ester

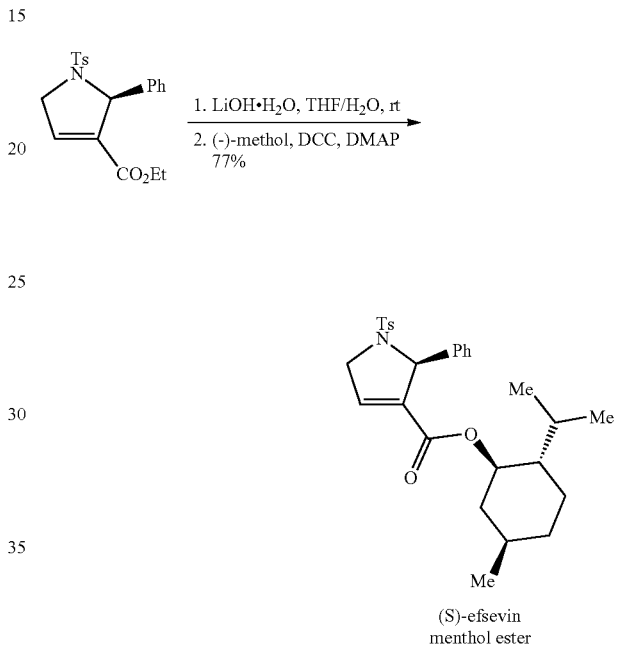

(S)-efsevin menthol ester (S)-Efsevin (50 mg, 0.135 mmol) was dissolved in 1:1 H$_2$O/THF (3.4 mL) at room temperature. Lithium hydroxide monohydrate (14.1 mg, 0.34 mmol) was added into the reaction mixture. The reaction was allowed to stir overnight at room temperature. The reaction was monitored by TLC. Upon completion, mixture was cooled to 0° C. using an ice bath and acidified to pH 1 with aq. 1N HCl. The mixture was extracted with DCM (10 mL×3). The combined organic layer was dried with Na$_2$SO$_4$ and concentrated in vacuo. The resulting carboxylic acid was used in the next step without further purification. (S)-Efsevin carboxylic acid (0.135 mmol) and (−)-menthol (31.7 mg, 0.2 mmol) were dissolved in DCM (1.0 mL) and cooled to 0° C. using an ice bath. DCC (27.9 mg, 0.135 mmol) and DMAP (0.2 mg, 0.0014 mmol) were dissolved in DCM (1.0 mL) and added to the reaction mixture over 1 h using a syringe pump. After addition, the reaction mixture was allowed to warm to room temperature by removing the cooling bath. Upon completion, the mixture was filtered through a short pad of celite and concentrated in vacuo. The crude product was purified using FCC on silica gel (20% EtOAc in hexanes) to yield (S)-efsevin menthol ester (50.0 mg, 77%).

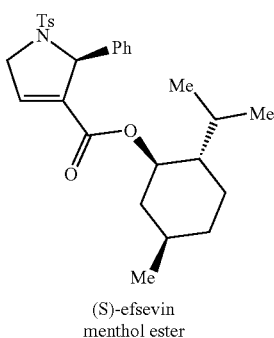 [SMILES: Cc1ccc(S(=O)(=O)N2CC=C(C(=O)O[C@@H]3C[C@H](C)CC[C@H]3C(C)C)[C@@H]2c2ccccc2)cc1]

(S)-efsevin menthol ester (S)-Efsevin Menthol Ester $^1$H NMR (500 MHz, CDCl3) (FIG. 15 top) δ 7.39 (d, J=8.3 Hz, 2H), 7.22-7.17 (m, 5H), 7.12 (d, J=8.0 Hz, 2H), 6.74 (q, J=2.0 Hz, 1H), 5.72 (dt, J=5.8, 2.0 Hz, 1H), 4.54-4.49 (m, 2H), 4.35 (ddd, J=16.9, 5.9, 2.0 Hz, 1H), 2.36 (s, 3H), 1.69-1.63 (m, 1H), 1.61-1.58 (m, 3H), 1.35-1.20 (m, 3H), 0.99-0.90 (m, 1H), 0.83 (d, J=7.1 Hz, 3H), 0.80-0.71 (m, 4H), 0.61 (d, J=7.0 Hz, 3H), 0.51 (q, J=11.8 Hz, 1H)

$^{13}$C NMR (125 MHz, CDCl3) (FIG. 15 bottom) δ 161.5, 143.2, 139.4, 136.5, 135.7, 134.9, 129.4, 128.2, 127.93, 127.86, 127.1, 75.0, 69.1, 54.9, 46.9, 40.2, 34.1, 31.2, 26.5, 23.6, 21.9, 21.5, 20.6, 16.5.

Examples 5-7

Synthesis of Screening Library & Zebrafish Screening

A. Introduction

We generation a large number of diverse small molecules to screen zebrafish tremblor mutants, defective in a cardiac-specific sodium calcium exchanger gene, NCX1h, to study cardiac arrhythmia induced by abnormal calcium ion handling. To achieve this, our group build up a diverse library by constructing diverse scaffolds such as dihydropyrroles (Zhu, et al., 2005, *Tetrahedron.*, 61, 6276-6282), tetrahydropyridines (Zhu, et al., 2003, *J. Am. Chem. Soc.*, 125, 4716-4717), cyclohexenes (Tran, et al., 2007, *J. Am. Chem. Soc.*, 129, 12632-12633), bicyclic succinimides, coumarins (Henry, et al., 2007, *Org. Lett.*, 9, 3069-3072), dioxanyidenes (Zhu, et al., 2005, *Org. Lett.*, 7, 1387-1390.), dihydropyrones (Creech, et al., 2008, *Org. Lett.*, 10, 429-432), and pyrenes (Zhu, et al., 2005, *Org. Lett.*, 7, 2977-2980) using phosphine-catalyzed reactions, phosphine-catalyzed reactions combined with Michael addition, or the sequence of phosphine-catalyzed reactions/Tebbe reactions/Diels-Alder reactions (see non-limiting examples in FIG. 18A-E). The library included a large number of efsevin analogs, including: analogs with ethyl ester motif by using different imines as one of the annulation coupling partners; and analogs with meta-, para-methyl substitutes, halogen substitutes, and unsubstituted benzaldehyde to react with orth-, para-methyl substitutes and halogen substituted benzenesulfonamide for imine synthesis.

B. General Information

Benzene and dichloromethane were distilled fresh from CaH$_2$. THF was distilled fresh from sodium. All other reagents were used as received from commercial sources. Reactions were monitored using thin layer chromatography (TLC) performed on 0.25-mm E. Merck silica gel plates (60F-254) and visualized under UV light or through permanganate staining. Flash column chromatography was performed using E. Merck silica gel 60 (230-400 mesh) and compressed air. NMR spectra were obtained on Bruker ARX-400, or Bruker AXR-300 instruments (as indicated), calibrated using residual undeuterated chloroform as an internal reference (7.26 and 77.0 ppm for $^1$H and $^{13}$C NMR spectra, respectively). $^1$H NMR spectral data are reported as follows: chemical shift (δ, ppm), multiplicity, coupling constant (Hz), and integration. $^{13}$C spectral data are reported in terms of the chemical shift. The following abbreviations are used to indicate multiplicities: s=singlet; d=doublet; t=triplet; q=quartet; m=multiplet; br=broad. Affi-gel-10 was purchased from BioRad. EDTA, EGTA, Glycine, NaF, phenylmethylsulfonylfluoride (PMSF) and Trizma base were purchased from Sigma Chemicals. Silver Stain Kit and pre-casted tris-glycine gel were obtained from Invitrogen. Protein inhibitor cocktail was purchased from Roche. Nonidet P-40 was from Fluka. Resin filtration procedures were carried out using a 70μ PE frit cartridges from Applied Separations (cat. #2449).

Example 5

Synthesis of N-Sulfonyimines and Allenoates

N-sulfonylimines for the screening library were synthesized from corresponding aldehydes and sulfonamides through the use of TiCl$_4$, according to the procedure in McKay, et al. (McKay, et al., 1981, *J. Chem. Soc., Perkin Trans.* 1, 2435). The rest of the imine were synthesized through the condensation of the corresponding aldehydes with the sulfonamides catalyzed by BF$_3$·OEt$_2$ with azeotropic water removal (Dean-Stark), according to the procedure in Jennings, et al. (Jennings, et al., 1991, *Tetrahedron*, 47, 5561). Ethyl buta-2,3-dienoate was synthesis according to the procedure in Lang, et al. (Lang, et al., 1984, *Organic Syntheses.*, 62, 202).

Example 6

Synthesis of Dihydropyrroles

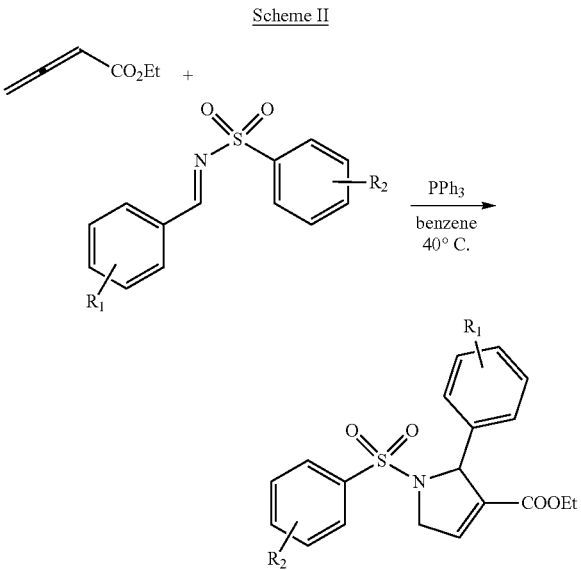

Scheme II

Dihydropyrroles for the screening library were synthesized according to the following general procedure. PPh$_3$ (1 mmol) and imine (1 mmol) were dissolved in dry benzene. Ethyl buta-2,3-dienoate (1.2 mmol) was added dropwised. The mixture was heated to 40° C. and stirred overnight (Scheme II). Solvent was removed under vacuum and the residue was purified by flash chromatography. (Ethyl acetate:Hexane=1:6-1:4).

Example 7

Zebrafish Screening

We screened our above mention library by using tremblor mutants Zebrafish embryos. The heart cells of tremblor mutant embryos do not establish rhythmic synchronized contraction but rather contract independently and create a chaotic contraction pattern. Compounds were screened for their ability to suppress cardiac fibrillation and/or restore rhythmic synchronized contraction. Briefly, we treated the embryo by soaking in 20 μM solution or injecting compounds after 24 hours fertilization and observed the phenotype after 48 hours. Further, we determined the structure-activity relationship (SAR) between the active compound's structures and the ability to suppress cardiac fibrillation and/or restore rhythmic synchronized contraction.

C. Methods

Soaking

Zebrafish tremblor mutant eggs were collected after fertilization, and arrayed in 24-well plates (20 twenty embryos/well) in 500 μL buffer. After 24 hour fertilization in 29° C., 20 μM testing compound was added and using E3 buffer as background control. After 48 hour fertilization in 29° C., phenotypic changes were observed using a high magnification dissecting microscope.

Injection with Morpholino

Zebrafish eggs were collected at 1 cell stages. 1 nL of compound in Daneu's buffer and 1 nL of morpholino (1 mM) to NCX1h was injected into the embryo. After 24 hours the embryo was arrayed in 24-well plates (20 twenty embryos/well) in 500 μL buffer. After 48 hour fertilization in 29° C., phenotypic changes were observed using a high magnification dissecting microscope.

Injection into Tremblor Mutants

Zebrafish tremblor mutant eggs were collected at 1 cell stages. 1 nL of compound in Daneu's buffer were injected into the embryo. After 24 hours the embryo was arrayed in 24-well plates (20 twenty embryos/well) in 500 μL buffer. After 48 hour fertilization in 29° C., phenotypic changes were observed using a high magnification dissecting microscope.

D. Results

Activity Analysis

We identified multiple active compounds from the library with similar or greater activity than efseven (see non-limiting examples in FIGS. 0A and 0B). Table 1 shows some of the most active compounds found in the screens.

TABLE 1

| Chemical | Soaking: Number of tremblor Mutants/ % Rescued | Injection with Morpholino: Number of Fish/ % Rescued | Injection into tremblor Mutants: Number of fish/ % Rescued |
| --- | --- | --- | --- |
| Formula Id | 18/80% | | |
| Formula Ie | 8/75% | | |

TABLE 1-continued

| Chemical | Soaking: Number of tremblor Mutants/ % Rescued | Injection with Morpholino: Number of Fish/ % Rescued | Injection into tremblor Mutants: Number of fish/ % Rescued |
| --- | --- | --- | --- |
| Formula If | 19/78% | | |
| Formula Ig | 17/88% | | |
| Formula Ih | | 14/50% | 10/80% |
| Formula Ii | | 8/75% | 15/87% |
| Formula Ij | | 8/88% | 28/79% |
| Formula Ik | | 8/75% | 26/85% |
| Formula Il | | 8/63% | 12/83% |
| Formula Im | | 8/88% | |
| Formula In | | 8/88% | |
| Formula Io | | 8/75% | |
| Formula Ip | | 8/38% | 27/74% |
| Formula Iq | | 6/67% | 21/81% |
| Formula Ir | | | 21/76% |
| Formula Is | | 6/67% | 23/87% |
| Formula It | | 6/0% | 30/73% |
| Formula Iu | | 8/88% | 43/74% |

Tables 2, 3, and 4 show additional screening results (see FIG. 18A-D for structures). Table 2 shows screening results using tremblor mutant soaked in 20 μM test compounds.

TABLE 2

| Chemical | Number of fish | Rescue percent |
| --- | --- | --- |
| F7 | 89 | 72% |
| F7-I-A02 | 12 | 33% |
| F7-I-A03 | 21 | 38% |
| F7-I-A04 | 27 | 31% |
| F7-I-A05 | 10 | 40% |
| F7-I-A06 | 17 | 88% |
| F7-I-A07 | 0 | Dead |
| F7-I-A08 | 14 | 57% |
| F7-I-A09 | 19 | 42% |
| F7-I-A10 | 14 | 50% |
| F7-I-A11 | 17 | 50% |
| F7-I-A12 | 14 | 60% |
| F7-I-B01 | 20 | 11% |
| F7-I-B02 | 15 | 40% |
| F7-I-B03 | 23 | 0% |
| F7-I-B04 | 8 | 75% |
| F7-I-B05 | 15 | 29% |
| F7-I-B06 | 13 | 0% |
| F7-I-B07 | 18 | 80% |
| F7-I-B08 | 13 | 43% |
| F7-I-B09 | 16 | 67% |
| F7 ketone | 51 | 26% |
| F7-I-B10 | 15 | 63% |
| F7-I-B11 | 19 | 30% |
| F7-I-B12 | 19 | 78% |
| F7-I-C01 | 15 | 33% |
| F7-I-C02 | 14 | 86% * |
| F7-I-C03 | 17 | 29% |
| F7-I-C04 | 26 | 62% |
| F7-I-C05 | 26 | 23% |
| F7-I-C06 | 15 | 11% |
| F7-I-C07 | 16 | 25% |
| F7-I-C08 | 9 | 11% |
| F7-I-C09 | 0 | Dead |
| F7-I-C10 | 0 | Dead |
| F7-I-C11 | 0 | Dead |
| F7-I-C12 | 15 | 100% ** |
| F7-I-D01 | 1 | Dead |
| F7-I-D02 | 9 | 0.0% |
| F7-I-D03 | 0 | Dead |
| F7-I-D04 | 19 | 15.8% |
| F7 acid | 47 | 21% |
| F7 methyl ester | 46 | 44% |
| F7 isopropyl ester | 42 | 41% |

Table 3 shows screening results using morpholino mutants.

TABLE 3

| Chemical | Number of fish | Rescue percent |
|---|---|---|
| F7-I-D05 | 8 | 0% |
| F7-I-D06 | 8 | 38% |
| F7-I-D07 | 8 | 38% |
| F7-I-D08 | 15 | 73% |
| F7-I-D09 | 8 | 13% |
| F7-I-D10 | 8 | 0% |
| F7-I-D11 | 8 | 0% |
| F7-I-D12 | 8 | 50% |
| F7-I-E01 | 16 | 63% |
| F7-I-E02 | 8 | 13% |
| F7-I-E03 | 8 | 0% |
| F7-I-E04 | 8 | 0% |
| F7-I-E05 | 16 | 75% |
| F7-I-E06 | 8 | 13% |
| F7-I-E07 | 16 | 50% |
| F7-I-E08 | 14 | 71% |
| F7-I-E09 | 8 | 50% |
| F7-I-E10 | 8 | 25% |
| F7-I-E11 | 8 | 0% |
| F7-I-E12 | 8 | 25% |
| F7-I-F01 | 16 | 81% |
| F7-I-F02 | 14 | 79% |
| F7-I-F03 | 8 | 0% |
| F7-I-F04 | 8 | 0% |
| F7-I-F05 | 14 | 50% |
| F7-I-F06 | 8 | 100% |
| F7-I-F07 | 8 | 0% |
| F7-I-F08 | 8 | 75% |
| F7-I-F09 | 8 | 75% |
| F7-I-F10 | 8 | 88% |
| F7-I-F11 | 8 | 88% |
| F7-I-F12 | 8 | 63% |
| F7-I-G01 | 8 | 100% |
| F7-I-G02 | 8 | 75% |
| F7-I-G03 | 8 | 100% |
| F7-I-G04 | 8 | 75% |
| F7-I-G05 | 8 | 100% |
| F7-I-G06 | 8 | 75% |
| F7-I-G07 | 8 | 88% |
| F7-I-G08 | 8 | 38% |
| F7-I-G09 | 6 | 67% |
| F7-I-G10 | 6 | 67% |
| F7-I-G11 | 7 | 86% |
| F7-I-G12 | 8 | 38% |
| F7-I-H01 | 8 | 63% |
| F7-I-H02 | 8 | 88% |
| F7-I-H03 | 8 | 88% |
| F7-I-H04 | 8 | 75% |
| F7-I-H05 | 8 | 88% |
| F7-I-H06 | 8 | 63% |
| F7-I-H07 | 8 | 63% |
| F7-I-H08 | 7 | 100% |
| F7-I-H09 | 10 | 10% |
| F7-I-H10 | 8 | 25% |
| F7-I-H11 | 8 | 88% |
| F7-I-H12 | 8 | 100% |
| F7-II-A01 | 8 | 38% |
| F7-II-A02 | 8 | 0% |
| F7-II-A03 | 8 | 88% |
| F7-II-A04 | 8 | 100% |
| F7-II-A05 | 8 | 13% |
| F7-II-A06 | 7 | 86% |
| F7-II-A07 | 6 | 17% |
| F7-II-A08 | 7 | 86% |
| F7-II-A09 | 6 | 17% |
| F7-II-A10 | 5 | 80% |
| F7-II-A11 | 6 | 0% |
| F7-II-A12 | 8 | 0% |
| F7-II-B01 | 6 | 67% |
| F7-II-B02 | 8 | 38% |

Table 4 shows screening results using injection into tremblor mutants.

TABLE 4

| Chemical | Screen 1 Number of fish | Screen 1 Rescue percent | Screen 2 Number of fish | Screen 2 Rescue percent | Screen 3 Number of fish | Screen 3 Rescue percent | Total of fish number | Average ratio rescue |
|---|---|---|---|---|---|---|---|---|
| F7-I-D08 | 13 | 23% | | | | | 13 | 23% |
| F7-I-E01 | 8 | 0% | | | | | 8 | 0% |
| F7-I-E05 | 8 | 50% | | | | | 8 | 50% |
| F7-I-E07 | 8 | 50% | | | | | 8 | 50% |
| F7-I-E08 | 12 | 42% | | | | | 12 | 42% |
| F7-I-F01 | 7 | 14% | | | | | 7 | 14% |
| F7-I-F02 | 12 | 58% | | | | | 12 | 58% |
| F7-I-F05 | 10 | 80% | | | | | 10 | 80% |
| F7-I-F06 | 10 | 40% | | | | | 10 | 40% |
| F7-I-F08 | 10 | 20% | | | | | 10 | 20% |
| F7-I-F09 | 15 | 87% | | | | | 15 | 87% |
| F7-I-F10 | 8 | 50% | | | | | 8 | 50% |
| F7-I-F11 | 10 | 80% | 18 | 78% | | | 28 | 79% |
| F7-I-F12 | 5 | 60% | | | | | 5 | 60% |
| F7-I-G01 | 11 | 73% | 12 | 50% | | | 23 | 61% |
| F7-I-G02 | 7 | 57% | | | | | 7 | 57% |
| F7-I-G03 | 10 | 20% | | | | | 10 | 20% |
| F7-I-G04 | 9 | 78% | 17 | 88% | | | 26 | 85% |
| F7-I-G05 | 11 | 73% | 14 | 50% | | | 25 | 60% |
| F7-I-G06 | 11 | 55% | | | | | 11 | 55% |
| F7-I-G07 | 10 | 40% | | | | | 10 | 40% |
| F7-I-G09 | 23 | 78% | | | | | 23 | 78% |
| F7-I-G10 | 28 | 66% | | | | | 28 | 66% |
| F7-I-G11 | 31 | 62% | | | | | 31 | 62% |
| F7-I-G12 | 42 | 61% | | | | | 42 | 61% |
| F7-I-H01 | 12 | 83% | | | | | 12 | 83% |
| F7-I-H02 | 5 | 100% | 19 | 74% | | | 24 | 79% |
| F7-I-H03 | 7 | 86% | 9 | 78% | | | 16 | 81% |
| F7-I-H04 | 6 | 100% | 6 | 67% | | | 12 | 83% |
| F7-I-H05 | 7 | 86% | 16 | 69% | 20 | 75% | 43 | 74% |
| F7-I-H06 | 9 | 44% | | | | | 9 | 44% |

TABLE 4-continued

| Chemical | Screen 1 | | Screen 2 | | Screen 3 | | Total of fish number | Average ratio rescue |
|---|---|---|---|---|---|---|---|---|
| | Number of fish | Rescue percent | Number of fish | Rescue percent | Number of fish | Rescue percent | | |
| F7-I-H07 | 10 | 90% | 21 | 52% | | | 31 | 65% |
| F7-I-H08 | 9 | 44% | | | | | 9 | 44% |
| F7-I-H09 | 8 | 88% | 15 | 46% | | | 23 | 61% |
| F7-I-H10 | 5 | 60% | | | | | 5 | 60% |
| F7-I-H11 | 9 | 56% | | | | | 9 | 56% |
| F7-I-H12 | 13 | 54% | | | | | 13 | 54% |
| F7-II-A01 | 27 | 74% | | | | | 27 | 74% |
| F7-II-A02 | 18 | 62% | | | | | 18 | 62% |
| F7-II-A03 | 17 | 60% | | | | | 17 | 60% |
| F7-II-A04 | 22 | 48% | | | | | 22 | 48% |
| F7-II-A05 | 7 | 29% | | | | | 7 | 29% |
| F7-II-A06 | 36 | 64% | | | | | 36 | 64% |
| F7-II-A07 | 15 | 33% | | | | | 15 | 33% |
| F7-II-A08 | 20 | 26% | | | | | 20 | 26% |
| F7-II-A09 | 16 | 22% | | | | | 16 | 22% |
| F7-II-A10 | 33 | 40% | | | | | 33 | 40% |
| F7-II-A11 | 30 | 73% | | | | | 30 | 73% |
| F7-II-A12 | 14 | 5% | | | | | 14 | 5% |
| F7-II-B01 | 7 | 91% | 14 | 79% | | | 21 | 81% |
| F7-II-B02 | 13 | 7% | | | | | 13 | 7% |
| F7-II-B10 | 33 | 58% | | | | | 33 | 58% |
| F7-II-B11 | 35 | 37% | | | | | 35 | 37% |
| F7-II-B12 | 21 | 76% | | | | | 21 | 76% |
| F7-II-C01 | 25 | 60% | | | | | 25 | 60% |
| F7-II-C02 | 17 | 65% | | | | | 17 | 65% |
| F7-II-C03 | 22 | 55% | | | | | 22 | 55% |

E. SAR Analysis

Further, SAR analysis showed that para-halogen, especially para-fluoro substituted benzaldehyde has good structure-function correlation. For benznensulfonamide the orth-fluoro and para-fluoro substituted groups also showed good structure-function correlation.

Those skilled in the art will know, or be able to ascertain, using no more than routine experimentation, many equivalents to the specific embodiments of the invention described herein. These and all other equivalents are intended to be encompassed by the following claims.

The invention claimed is:

1. A method of regulating cardiac rhythmicity in a subject having cardiac rhythmicity, comprising potentiating mitochondrial Ca²⁺ uptake by administering to the subject having cardiac rhythmicity a composition comprising a compound of Formula Ic

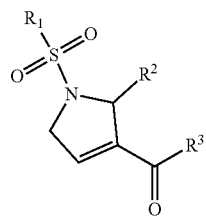

Formula Ic wherein:

R₁ is phenyl, heteroaryl, or substituted phenyl group; R₂ is a phenyl, heteroaryl, substituted phenyl, or hydrocarbyl group with or without a heteroatom; and R₃ is an alkoxy, the compound being administered in an effective amount to potentiate mitochondrial Ca²⁺ uptake so as to modulate cardiac rhythmicity in a subject; and the composition comprises at least 95% enantiomeric excess of the (R) form of the compound.

2. The method of claim 1, wherein R₁ is para-tolyl, R₂ is phenyl, and R₃ is ethoxy.

3. The method of claim 1, wherein R₁ is orth-fluoro substituted phenyl, a meta-fluoro substituted phenyl, or para-fluoro substituted phenyl.

4. The method of claim 1, wherein R₃ is menthyloxy.

5. The method of claim 1, wherein R₂ is para-fluoro substituted phenyl or a meta-fluoro substituted phenyl.

6. The method of claim 1, wherein the composition comprises the compound of Formula Ic as an enantiomerically pure form of Formula Ia

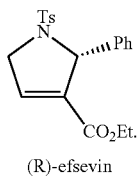

Formula Ia (R)-efsevin

7. The method of claim 1, wherein the compound of Formula Ic is efsevin or a compound having the structure of

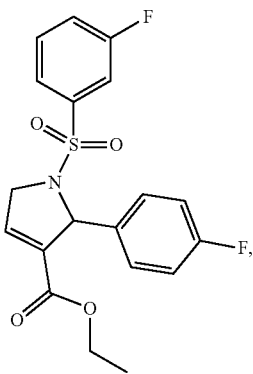

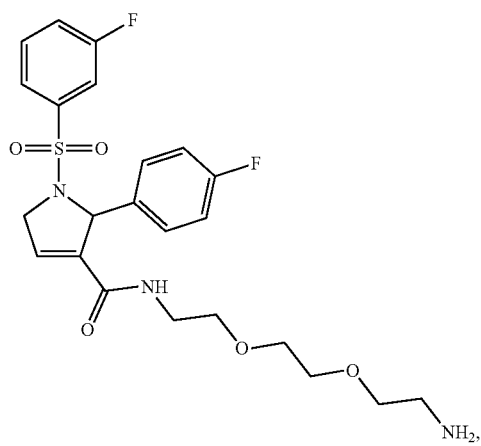

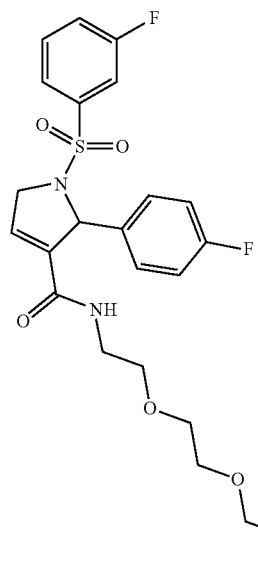

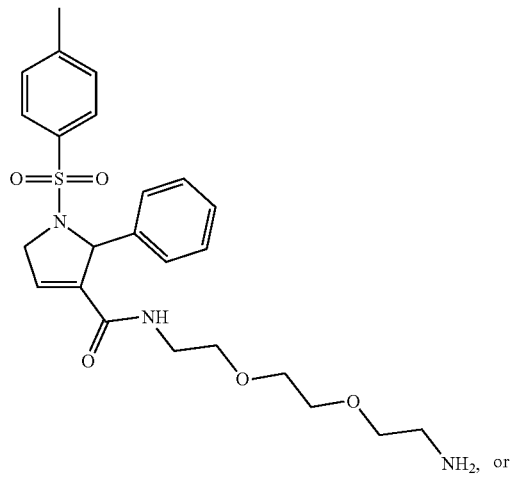
or
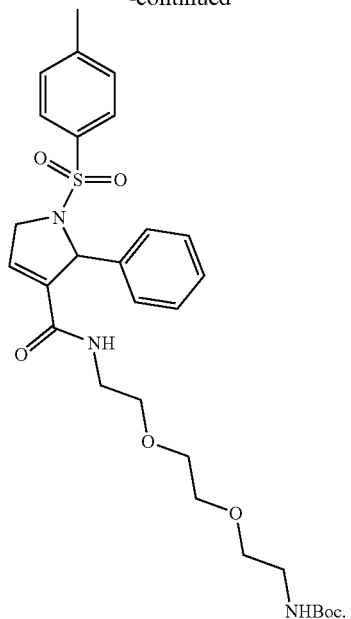
8. The method of claim 1, wherein the compound of Formula Ic is in an enantiomerically pure form.
* * * * *